US009815793B2

(12) United States Patent
Johnson et al.

(10) Patent No.: US 9,815,793 B2
(45) Date of Patent: Nov. 14, 2017

(54) ARTICLES AND METHODS COMPRISING PERSISTENT CARBENES AND RELATED COMPOSITIONS

(71) Applicant: Massachusetts Institute of Technology, Cambridge, MA (US)

(72) Inventors: Jeremiah A. Johnson, Boston, MA (US); Aleksandr V. Zhukhovitskiy, El Cerrito, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/171,998

(22) Filed: Jun. 2, 2016

(65) Prior Publication Data

US 2016/0355484 A1    Dec. 8, 2016

Related U.S. Application Data

(62) Division of application No. 14/210,187, filed on Mar. 13, 2014, now Pat. No. 9,382,210.

(60) Provisional application No. 61/817,529, filed on Apr. 30, 2013, provisional application No. 61/779,251, filed on Mar. 13, 2013.

(51) Int. Cl.
| | | |
|---|---|---|
| *C07D 233/20* | (2006.01) | |
| *C07D 233/06* | (2006.01) | |
| *C07D 403/10* | (2006.01) | |
| *C08F 292/00* | (2006.01) | |
| *C07D 403/14* | (2006.01) | |

(52) U.S. Cl.
CPC ......... *C07D 233/20* (2013.01); *C07D 233/06* (2013.01); *C07D 403/10* (2013.01); *C07D 403/14* (2013.01); *C08F 292/00* (2013.01)

(58) Field of Classification Search
None
See application file for complete search history.

(56) References Cited

U.S. PATENT DOCUMENTS

| | | |
|---|---|---|
| 6,699,527 B1 | 3/2004 | Moloney et al. |
| 7,632,777 B2 | 12/2009 | Teshigahara et al. |
| 8,278,456 B2 | 10/2012 | Robinson et al. |
| 9,382,210 B2 | 7/2016 | Johnson et al. |
| 2007/0043180 A1 | 2/2007 | Zhan |
| 2010/0130763 A1 | 5/2010 | Gao |
| 2014/0275555 A1 | 9/2014 | Johnson et al. |
| 2016/0199875 A1 | 7/2016 | Crudden et al. |
| 2016/0289248 A1 | 10/2016 | Johnson et al. |

FOREIGN PATENT DOCUMENTS

| | | |
|---|---|---|
| CN | 1907992 A | 2/2007 |
| WO | WO 00/26180 A1 | 5/2000 |
| WO | WO 2013/012905 A2 | 1/2013 |
| WO | WO 2015/024120 A1 | 2/2015 |

OTHER PUBLICATIONS

Vignolle et al., ChemCommun (Camb). Dec. 14, 2009;(46):7230-2.*
Invitation to Pay Additional Fees for PCT/US2014/026752 dated Jun. 18, 2014.
International Search Report and Written Opinion for PCT/US2014/026752 dated Sep. 23, 2014.
International Preliminary Report on Patentability for PCT/US2014/026752 dated Mar. 18, 2015.
Extended European Search Report for EP 14775147.3 dated Jun. 28, 2016.
Aksin et al., Effect of immobilization on catalytic characteristics of saturated Pd-N-heterocyclic carbenes in Mizoroki-Heck reactions. Journal of Organometallic Chemistry. Jun. 15, 2006; 691(13):3027-36.
Alcarazo et al., 1,3-Bis(N,N-dialkylamino)imidazolin-2-ylidenes: synthesis and reactivity of a new family of stable N-heterocyclic carbenes. J Am Chem Soc. Oct. 20, 2004;126(41):13242-3.
Angelici et al., Isocyanide ligands adsorbed on metal surfaces: applications in catalysis, nanochemistry, and molecular electronics. Inorg Chem. Oct. 20, 2008;47(20):9155-65. doi: 10.1021/ic800513t. Epub Aug. 26, 2008.
Angelici, Organometallic chemistry and catalysis on gold metal surfaces. Journal of Organometallic Chemistry. Mar. 2008;693(5):847-56.
Aslanov et al., Stabilization of silicon nanoparticles by carbenes. Russian Journal of Coordination Chemistry. May 2010;36(5):330-2.
Boydston et al., Modular fluorescent benzobis(imidazolium) salts: syntheses, photophysical analyses, and applications. J Am Chem Soc. Mar. 12, 2008;130(10):3143-56. doi: 10.1021/ja7102247. Epub Feb. 14, 2008.
Burzlaff, Tripodal N,N,O-Ligands for Metalloenzyme Models and Organometallics. Excerpt from Advances in Inorganic Chemistry. Academic Press. 2008; 60:139-40.
Chardon et al., Direct functionalisation of group 10 N-heterocyclic carbene complexes for diversity enhancement. Chem. Commun. 2011;47:5864-6.

(Continued)

*Primary Examiner* — Kamal Saeed
(74) *Attorney, Agent, or Firm* — Wolf, Greenfield & Sacks, P.C.

(57) ABSTRACT

Articles and methods comprising persistent carbenes are provided, as well as related compositions. In some embodiments, a persistent carbene may be associated with a portion of a substrate (e.g., at least a portion of a surface on the substrate). In certain embodiments, the association of persistent carbene with the substrate may be used to affect certain properties of substrate (e.g., surface chemistry, stability). In some cases, a persistent carbene may be functionalized after association with a portion of a substrate. In some embodiments, a persistent carbene and at least one secondary compound may be associated with a portion of a substrate. Articles and methods of the present invention may be useful for applications involving electronics, sensing, microfabrication, nanotechnology, biomimetic, and drug delivery, amongst others.

8 Claims, 20 Drawing Sheets

(56) References Cited

OTHER PUBLICATIONS

Chardon et al., Easy Derivatisation of Gropu 10 N-Heterocyclic Carbene Complexes and In Vitro Evaluation of an Anticancer Oestradiol Conjugate. ChemPlusChem. 2012;77:1028-38.

Crudden et al., Ultra stable self-assembled monolayers of N-heterocyclic carbenes on gold. Nat Chem. May 2014;6(5):409-14. doi: 10.1038/nchem.1891. Epub Mar. 23, 2014. Erratum in: Nat Chem. Jun. 2014;6(6):553.

Gonzalez-Galvez et al., NHC-stabilized ruthenium nanoparticles as new catalysts for the hydrogenation of aromatics. Catalysis Science & Technology. 2013;3:99-105.

Herrmann et al., N-Heterocyclic Carbenes. Angewandte Chemie International Edition in English. Nov. 3, 1997;36(20):2163-87.

Hirano et al., A modular synthesis of highly substituted imidazolium salts. Org Lett. Feb. 19, 2009;11(4):1019-22. doi: 10.1021/o18029609.

Hurst et al., N-Heterocyclic carbine coated metal nanoparticles. New Journal of Chemistry. Jul. 2009;33(9):1837-40.

Jacobsen et al., Understanding the M—(NHC) (NHC=N-heterocyclic carbine) bond. Coordination Chemistry Reviews. Mar. 2009;253(5-6):687-703.

Kuhn et al., A facile preparation of imidazolinium chlorides. Org Lett. May 15, 2008;10(10):2075-7. doi: 10.1021/o1800628a. Epub Apr. 16, 2008.

Lara et al., Ruthenium nanoparticles stabilized by N-heterocyclic carbenes: ligand location and influence on reactivity. Angew Chem Int Ed Engl. Dec. 9, 2011;50(50):12080-4. doi: 10.1002/anie.201106348. Epub Oct. 28, 2011.

Lee et al., Silver(I) N-Heterocyclic Carbenes with Long N-Alkyl Chains. Organometallics Jun. 2006;25(15):3768-75.

Melaiye et al., Silver(I)-imidazole cyclophane gem-diol complexes encapsulated by electrospun tecophilic nanofibers: formation of nanosilver particles and antimicrobial activity. J Am Chem Soc. Feb. 23, 2005;127(7):2285-91.

Mercs et al., Beyond catlysis; N-heterocyclic carbine complexes as components for medicinal, luminescent, and functional materials applications. Chemical Society Reviews. 2010;39:1903-12.

Moloney, Functionalized polymers by chemical surface modification. J. Phys. D: Appl Phys. 2008;41:174006. 9 pages.

Nativo et al., Uptake and intracellular fate of surface-modified gold nanoparticles. ACS Nano. Aug. 2008;2(8):1639-44. doi: 10.1021/nn800330a.

Osteraas et al., Incorporation of Functional Groups onto the Surface of Polyethylene. Nature. Mar. 22, 1969;221:1140-1.

Ott et al., Nanoclusters in ionic liquids: evidence for N-heterocyclic carbene formation from imidazolium-based ionic liquids detected by (2)H NMR. J Am Chem Soc. Apr. 27, 2005;127(16):5758-9.

Prades et al., Pyracenebis(imidazolylidene): A New Janus-Type Biscarbene and Its Coordination to Rhodium and Iridium. Organometallics. 2012; 31(12):4623-6.

Ranganath et al., Asymmetric nanocatalysis: N-heterocyclic carbenes as chiral modifiers of Fe3O4/Pd nanoparticles. Angew Chem Int Ed Engl. Oct. 11, 2010;49(42):7786-9. doi: 10.1002/anie.201002782.

Ranganath et al., Comparison of Superparamagnetic $Fe_3O_4$-Supported N-Heterocyclic Carbene-Based Catalysts for Enantioselective Allylation. ChemCatChem. 2011;3:1889-91.

Thibaudau, Ultrafast Photothermal Release of DNA from Gold Nanoparticles. J Phys Chem Lett. Apr. 5, 2012;3(7):902-7. doi: 10.1021/jz3001213. Epub Mar. 16, 2012.

Vignolle et al., N-heterocyclic carbene-stabilized gold nanoparticles and their assembly into 3D superlattices. Chem Commun (Camb). Dec. 14, 2009;(46):7230-2. doi: 10.1039/b913884f.

Von Wrochem et al., Efficient electronic coupling and improved stability with dithiocarbamate-based molecular junctions. Nat Nanotechnol. Aug. 2010;5(8):618-24. doi: 10.1038/nnano.2010.119. Epub Jun. 20, 2010.

Weidner et al., NHC-Based Self-Assembled Monolayers on Solid Gold Substrates. Aust J Chem. Aug. 19, 2011;64(8):1177-1179.

Zheng et al., One-step one-phase synthesis of monodisperse noble-metallic nanoparticles and their colloidal crystals. J Am Chem Soc. May 24, 2006;128(20):6550-1.

Zhou et al., Catalytic reactions of carbine precursors on bulk gold metal. J Am Chem Soc. Aug. 26, 2009;131(33):11734-43. doi: 10.1021/ja900653s.

Zhukhovitskiy et al., Addressable carbine anchors for gold surfaces. J Am Chem Soc. May 22, 2013;135(20):7418-21. doi: 10.1021/ja401965d. Epub May 13, 2013.

Zhukhovitskiy et al., Click-o-mers with n-heterocyclic carbenes for sensing metal ions and stabilizing gold nanoparticles. Polymer Preprints. Aug. 2012;53(2):450-1.

Zhukhovitskiy et al., Functionalizable (F-)NHCs and poly(NHC)s: a novel modular ligand platform for gold nanoparticles and surfaces. PowerPoint Presentation. ACS National Meeting & Exposition. Philadelphia, PA. Aug. 20, 2012.

Zlatogorsky et al., Synthesis, Structures, and Reactivity of Chelating Bis-N-Heterocyclic-Carbene Complexes of Iron(II). Organometallics. 2011;30(18):4974-82.

\* cited by examiner

FIG. 1A
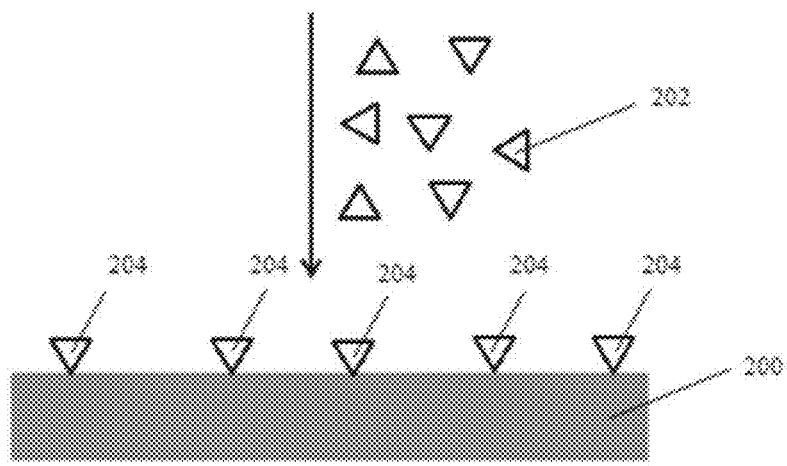
FIG. 1B
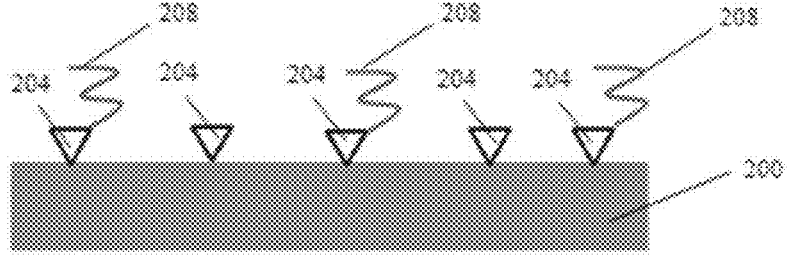
FIG. 1C

FIG. 7A    FIG. 7B
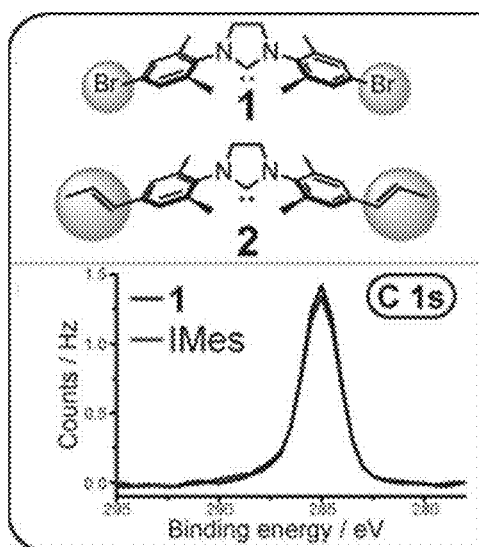
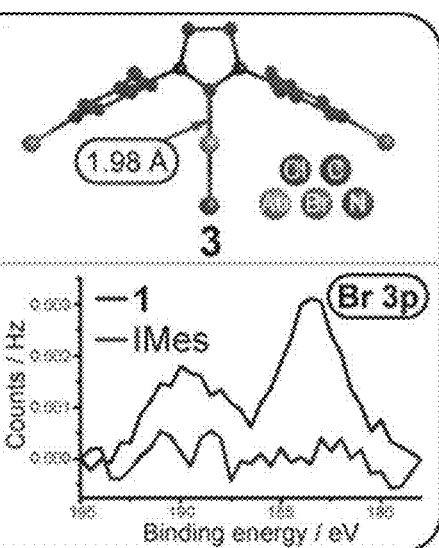
FIG. 7C    FIG. 7D

ARTICLES AND METHODS COMPRISING PERSISTENT CARBENES AND RELATED COMPOSITIONS

RELATED APPLICATIONS

This application is a divisional of U.S. patent application Ser. No. 14/210,187, filed Mar. 13, 2014, entitled "Articles and Methods Comprising Persistent Carbenes and Related Compositions" by Johnson, et al. which claims the benefit of U.S. Provisional Patent Application Ser. No. 61/779,251, filed Mar. 13, 2013, entitled "Articles and Methods Comprising Persistent Carbenes and Related Compositions," by Johnson, et al. and U.S. Provisional Patent Application Ser. No. 61/817,529, filed Apr. 30, 2013, entitled "Articles and Methods Comprising Persistent Carbenes and Related Compositions," by Johnson, et al., each of which are incorporated herein by reference in their entirety.

TECHNICAL FIELD

Articles and methods comprising persistent carbenes are provided, as well as related compositions.

BACKGROUND

While the modification of substrates using chemical structures has been widely employed, many conventional substrate modifiers have limited utility. One example is the modification of gold surfaces with thiols to form monolayers. The relatively weak binding energy, ill-defined binding geometry, and non-conductive nature of S—Au bonds limits the applications of gold surfaces modified with thiols. For example, the relatively weak S—Au bond (~45 kcal/mol) can lead to monolayer desorption at moderate temperatures (~100-150° C.). In addition, the S—Au bonds are typically non-conductive, which can limit their use in molecular electronics applications. The association of persistent carbenes with substrates has received little attention.

Accordingly, improved compositions, articles, and methods are needed.

SUMMARY

Articles and methods comprising persistent carbenes are provided, as well as compositions comprising the persistent carbenes and related precursors. The subject matter of the present invention involves, in some cases, interrelated products, alternative solutions to a particular problem, and/or a plurality of different uses of one or more systems and/or articles.

In one aspect, the present invention is generally directed to a method. In accordance with one set of embodiments, a method comprises associating a persistent carbene with a portion of a substrate. In some cases, the persistent carbene comprises at least one functionalizable group. In some instances, the method further comprises functionalizing the at least one functionalizable group of the persistent carbene associated with the substrate.

In another set of embodiments, a method comprise associating a first substrate with a first persistent carbene, wherein the first persistent carbene is associated with a second persistent carbene via a linker, and associating the second persistent carbene with a second substrate.

In one set of embodiments, a method comprises providing a first compound having the structure:

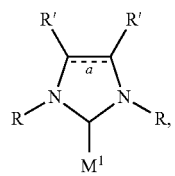

and exposing the structure to reaction conditions to form a second compound having the structure:

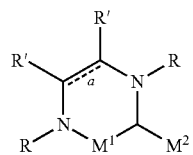

wherein each R is independently hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile; when present, each R' is independently hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile; optionally, any two R may be joined to form a ring; optionally, any R may be substituted with a group forming a bond to a second persistent carbene; $\overline{a}$ is a single or double bond, provided when $\overline{a}$ is a double bond each R' is absent; and $M^1$ and $M^2$ are independently a metal or metalloid comprised in the substrate.

The present invention, in another aspect, is generally directed to an article. In one set of embodiments, an article comprises a substrate having a surface. In some instances, at least a portion of the surface is associated with a plurality of persistent carbenes and a plurality of secondary compounds. In some cases, each of the plurality of the persistent carbenes and each of the plurality of the secondary compounds comprise at least one functionalizable group.

In another set of embodiments, an article comprises a carbene compound comprising a first persistent carbene and a second persistent carbene, a first substrate associated with the first persistent carbene, and a second substrate associated with the second persistent carbene.

In one set of embodiments, an article comprises the structure:

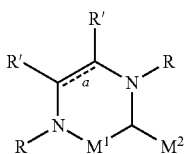

wherein each R is independently hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile; when present, each R' is independently hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile; optionally, any two R may be joined to form a ring; optionally, any R may be substituted with a group forming a bond to a second persistent carbene; <u>a</u> is a single or double bond, provided when <u>a</u> is a double bond each R' is absent; and $M^1$ and $M^2$ are independently a metal or metalloid comprised in the substrate.

In another aspect, the present invention is generally directed to a set of compounds. In one set of embodiments, a compound having the structure:

wherein each X is independently selected from the group consisting of —NR—, —N=, —N$^+$R=, —C—, —CR=, —CR$_2$—, —C$^-$R—, —S—, and —O—; each R is independently hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile, provided at least one R comprises a functionalizable group;

optionally, any two R may be joined to form a ring; and optionally, any R may be substituted with a group forming a bond to a second persistent carbene.

In another set of embodiments, the compound has the structure:

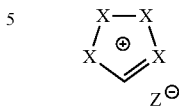

wherein each X is independently selected from the group consisting of —NR—, —N=, —N$^+$R=, —C—, —CR=, —CR$_2$—, —C$^-$R—, —S—, and —O—; each R is independently hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile, provided at least one R comprises a functionalizable group;

optionally, any two R may be joined to form a ring; optionally, any R may be substituted with a group forming a bond to a second persistent carbene; and $Z^-$ is a counter anion.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 1A-FIG. 1C show the functionalization of persistent carbenes associated with a substrate, according to certain embodiments.

FIG. 7A shows non-limiting persistent carbene structures, according to one set of embodiments.

FIG. 7B shows a crystal structure of a persistent carbene-gold complex, according to one set of embodiments.

FIG. 7C shows the C 1s region of X-ray photoelectron spectra for persistent carbenes bound to planar gold surfaces, according to one set of embodiments.

FIG. 7D shows the Br 3p regions of the same X-ray photoelectron spectra from FIG. 7C, according to one set of embodiments.

DETAILED DESCRIPTION

Articles and methods comprising persistent carbenes are generally described, as well as compositions comprising the persistent carbenes and related carbene precursors. In some embodiments, methods are provided for associating a persistent carbene with a portion of a substrate (e.g., at least a portion of a surface on the substrate). In certain embodiments, the association of one or more persistent carbenes with the substrate may alter certain properties of substrate, for example, the surface chemistry and/or the stability of the substrate. Further, in some embodiments, after association with the substrate, the persistent carbene may be functionalized, associated with a second substrate, and undergo additional reactions. Articles and methods of the present invention may be useful for applications involving monolayers, nanoparticles, microparticles, electronics, sensing, microfabrication, nanotechnology, biomimetic, and drug delivery, amongst others, as described herein.

In some embodiments, methods are provided for associating a substrate with a persistent carbene. In some cases, the method comprising associating a persistent carbene with a portion of a substrate, wherein the persistent carbene comprises at least one functionalizable group. The at least one functionalizable group of the persistent carbene associated with the substrate may then be functionalized.

In some embodiments, association of a persistent carbene, optionally followed by functionalization of the persistent carbene, may affect the surface chemistry of a substrate. For example, in some cases, the association of the persistent carbene with the substrate provides for different chemical entities present on the substrate. As another example, in some cases, association of a persistent carbene with a substrate may aid in the stabilization of the substrate. In some embodiments, the substrate is a particle and the association of the persistent carbene with the particle may lead to the stabilization of the particle in its environment.

A non-limiting method is illustrated in FIG. 1. In FIG. 1A, substrate 200 is provided. Substrate 200 is exposed to plurality of persistent carbenes 202, at least a portion of which (e.g., 204) associate with a portion of the substrate, as shown in FIG. 1B. At least a portion of the persistent carbenes associated with the surface may then be functionalized with functional groups 208, as shown in FIG. 1C, for example, by exposing the substrate associated with the persistent carbenes to a plurality of molecules comprising the functional group 206.

Figure 2A:
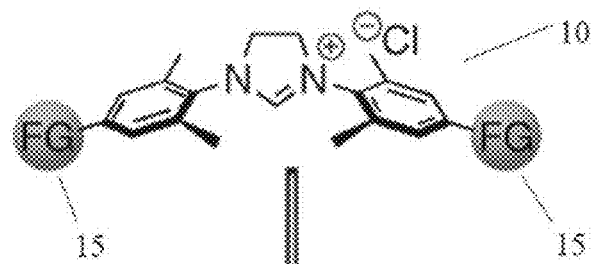
FIG. 2A-FIG. 2C show the functionalization of persistent carbenes associated with a substrate, according to one set of embodiments.
Figure 2B:
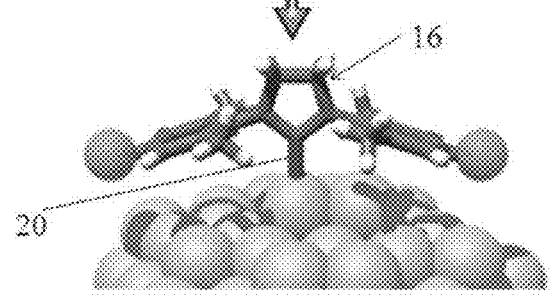
Figure 2C:
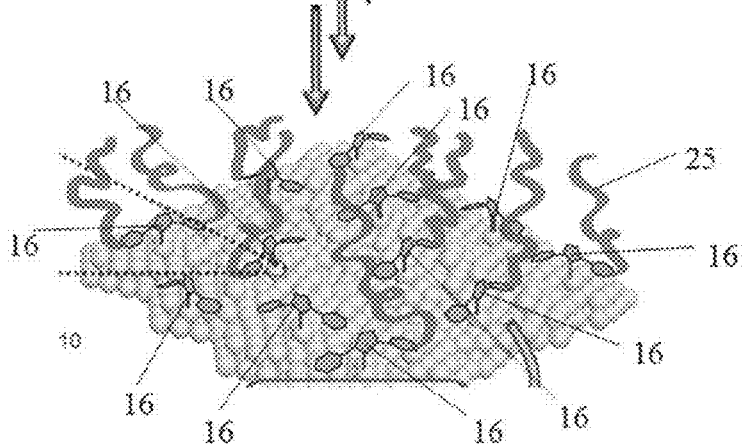

FIG. 2 illustrates an additional non-limiting embodiment of a method of the present invention. In FIG. 2A, a persistent carbene precursor 10 is provided comprising functionalizable groups 15. The persistent carbene precursor is converted to a persistent carbene 16 via a chemical or physical treatment (not shown; e.g., via exposure to a base, via exposure to heat). After conversion, the persistent carbene is associated with a substrate via a chemical interaction 20, as shown in FIG. 2B. For example, the persistent carbene may form a covalent bond with a portion of the surface (e.g., an atom on the surface). As another example, the persistent carbene may be associated with the substrate due to a physical interaction. Generally, a plurality of persistent carbene is associated with at least a portion of a substrate as shown in FIG. 2C (e.g., 16). Following association of the persistent carbenes with the surface, at least a portion of the persistent carbenes may be functionalized. For example, as shown in FIG. 2C, at least one of the functionalizable groups of a portion of the persistent carbenes may be functionalized after association with the substrate. Methods for functionalizing the persistent carbenes (e.g., via the functionalizable group) are described herein.

In some embodiments, the surface may be associated with a persistent carbene and a secondary compound, each of which may comprises a functionalizable group. For example, a persistent carbene and a secondary compound comprising a thiol may each be associated with a portion of the substrate via the carbene and the thiol, respectively. In certain instances, each of the persistent carbene and the secondary compound may be functionalized following association with the substrate. In some embodiments, one class of compounds (e.g., persistent carbenes) may be functionalized without functionalizing another class of compounds (secondary compound). In some embodiments, the secondary compound may be functionalized without functionalizing the persistent carbenes. For instance, in certain embodiments, the at least one functionalizable group on the persistent carbene may be structurally different from the at least one functionalizable group on the secondary compounds. The structural difference may cause the functionalizable groups to have differing reactivities towards certain molecules. The different reactivities may allow one class of compounds to be selectively functionalized. For example, the functionalizable groups of the persistent carbenes may be functionalized with a first type of functional group via a first type of chemical reaction, and the functionalizable groups of the secondary compounds may be associated with a second type of functional group via a second type of chemical reaction. In other embodiments, the persistent carbene and the secondary compounds may be functionalized at substantially the same time. In embodiments in which the reactivity of the functionalizable group on the persistent carbene and the secondary compound differ, the persistent carbene and the secondary compound may be selectively functionalized at substantially the same time.

In some embodiments, more than one type of secondary compound (e.g., a first type of secondary compound and a second type of secondary compound) may be associated with the surface along with the persistent carbene. Any suitable number of types of secondary compounds may be associated with the substrate (e.g., one type, two types, three types, four types, etc.).

A non-limiting method comprising associating a persistent carbene and at least one secondary compound is illustrated in FIG. 3. In FIG. 3A, substrate 220 is provided. Substrate 220 is exposed to plurality of persistent carbenes 222, at least a portion of which (e.g., 224) associate with a portion of the substrate, as shown in FIG. 3B. Substrate 220 is also exposed to plurality of secondary compounds 226, at least a portion of which (e.g., 228) associate with a portion of the substrate, as shown in FIG. 3C. Steps B and C may occur sequentially (e.g., B then C, or C then B) or substantially simultaneously (e.g., substrate 220 is exposed to plurality of persistent carbenes 222 and plurality of secondary compounds 226 substantially simultaneously). In some embodiments, at least a portion of the persistent carbenes associated with the surface may then be functionalized with functional group 232, as shown in FIG. 1D, for example, by exposing the substrate associated with the persistent carbenes to a plurality of molecules comprising the functional group 230. Additionally or alternatively, at least a portion of secondary compounds associated with the surface may be functionalized with functional group 236, as shown in FIG. 1E, for example, by exposing the substrate associated with the persistent carbenes to a plurality of molecules comprising the functional group 234. Steps D and E may occur sequentially (e.g., D then E, or E then D) or substantially simultaneously (e.g., substrate 220 associated with a plurality of secondary compounds and persistent carbene is exposed to plurality of molecules 230 and 234 substantially simultaneously). Those of ordinary skill in the art will be aware of other suitable combinations of methods steps to result in the final product. For example, A-B-D-C-E, A-B-D-C, A-B-D-E, etc. In some embodiments, more than one type of secondary compound may be associated with the substrate, as described in more detail herein.

In some embodiments, modifying a substrate with a persistent carbene (and/or a secondary compound) may allow certain properties of the substrate to be finely controlled or tuned. In some cases, the surface chemistry of the substrate may be controlled. It has been discovered within the context of the present invention that persistent carbenes may overcome certain limitations of conventional surface modifiers and serve as a versatile class of reagents for substrate modification. In some embodiments, persistent carbenes may offer a combination of exceptional σ-donating and moderate π-backbonding ability, which may allow the persistent carbenes to form strong associations with substrates. Furthermore, the synthetic flexibility of persistent carbenes and the nature of their association with substrates may facilitate the general use of persistent carbenes for substrate modification. For example, the persistent carbene and/or secondary compound may be used to alter the surface chemistry of the substrate by associating the persistent carbene and/or secondary compounds with the substrate at selected portion, optionally followed by functionalization of the persistent carbenes and/or secondary compounds. In embodiments where the persistent carbenes and/or secondary carbenes are functionalized, the ability to functionalize the persistent carbenes and/or secondary compounds with a wide variety of functional groups (e.g., via reaction between a functionalizable group and a functional group) can also be used to control the surface chemistry of the substrate. Additional details are provided herein.

A persistent carbene and/or secondary compound may be associated with a portion of a substrate via formation of a chemical interaction between the persistent carbene and a portion of the substrate. In some embodiments, the persistent carbene and/or secondary compound may be associated with the substrate via formation of at least one chemical bond, such as an ionic bond, a covalent bond (e.g., carbon-carbon, carbon-oxygen, oxygen-silicon, sulfur-sulfur, phosphorus-nitrogen, carbon-nitrogen, metal-oxygen, or other covalent bonds), a hydrogen bond (e.g., between hydroxyl, amine, carboxyl, thiol, and/or similar functional groups), a dative bond (e.g., complexation or chelation between metal ions and monodentate or multidentate ligands), Van der Waals interactions, and the like. "Association" of the compound (e.g., persistent carbene, secondary compound) with the substrate would be understood by those of ordinary skill in the art based on this description. In some embodiments, the association may comprise the formation of a covalent bond.

In some embodiments, the association of a persistent carbene and a portion of the substrate may be via the carbene moiety (i.e., two unpaired electrons) of the persistent carbene. In some such embodiments, the carbene moiety may form a bond (e.g., covalent bond, dative bond) with the substrate, such that the previously unshared electrons of the carbene moiety are shared with the substrate. It should be understood that, in some cases, a persistent carbene associated with a substrate refers to a persistent carbene bonded to the substrate via the carbene moiety. In certain embodiments, the chemical interaction between the carbene moiety of the persistent carbene and the portion of a substrate may be relatively strong such that the association is relatively stable under a variety of conditions (e.g., temperatures greater than 150° C.). In other embodiments, the persistent carbene may be associated with a portion of a substrate due to a spatial orientation that allows for a persistent carbene to be in close proximity to the substrate. For example, the persistent carbene may be associated via a chemical interaction that is not via the carbene moiety.

In some embodiments, the persistent carbene may be associated with the substrate via more than one chemical bond. In certain embodiments, the persistent carbene may be associated with the substrate via the carbene moiety and a non-carbene atom or moiety (e.g., nitrogen, amine) in the persistent carbene. For example, a heterocyclic carbene may be associated with a substrate (e.g., silicon) via the carbene moiety and a heteroatom (e.g., nitrogen). In certain embodiments, the persistent carbene may first associate with the substrate via the carbene moiety and undergo a process (e.g., ring expansion) that allows the persistent carbene to also associate with the substrate via the non-carbene moiety (e.g., heteroatom). In some instances, the persistent carbene may be exposed to certain conditions (e.g., heat) to cause the process (e.g., rearrangement, ring expansion). In some embodiments, the carbene moiety and the non-carbene moiety in the persistent carbene associate with the same atom in the substrate. In other embodiments, the carbene moiety and the non-carbene moiety in the persistent carbene associate with the different atoms in the substrate. Regardless of whether the moieties are associated with the same or different atoms in the substrate, the association between the non-carbene moiety and the substrate may be labile. In some such cases, the labile bond may be used to functionalize the atom of the substrate associated with the non-carbene moiety. For instance, in embodiments in which the carbene moiety and the non-carbene moiety are associated with same atom (e.g., Si), the labile bond may be used to associate the atom with the carbene moiety and another compound (e.g., a secondary compound).

In some embodiments, a compound comprising a plurality of persistent carbenes may be anchored to a substrate via at least one chemical bond between at least one of the persistent carbenes comprised in the compound and the substrate, whereas at least one other persistent carbene may not form a chemical bond with the substrate, however may be in physical proximity to the substrate. The at least one persistent carbene in physical proximity to the substrate but not chemically bound may be referred to as a free carbene moiety. The free carbene moiety may be used in chemical reactions, bound to another substrate, used as a seeding layer, or in certain applications (e.g., sensing, wherein the free carbene moiety may associate with a chemical to be sensed, e.g., see FIG. 6B), as described herein.

Those of ordinary skill in the art will be aware of methods for associating a persistent carbene with a substrate. In some embodiments, an association may be formed when the substrate is exposed to the persistent carbene. In some cases, the substrate may be exposed to a solution of the persistent carbene. For instance, the substrate may be immersed and optionally incubated in a solution or composition comprising the persistent carbene. In some instances, after immersion the substrate is washed with one or more solvents. In one example, a substrate may be immersed in a solution comprising persistent carbene (e.g., 10 mM persistent carbene in anhydrous tetrahydrofuran solution) for 24 h at room temperature in an inert environment. The substrate may then be washed with one or more organic solvent (e.g., tetrahydrofuran, dichloromethane, methanol, and hexane). In some embodiments, a solution or composition comprising a persistent carbene may be flowed over the substrate. In other instances, an association may be formed by spray or spin coating the solution or composition comprising a persistent carbene on the substrate. For example, a solution comprising persistent carbene (e.g., 0.21 mM persistent carbene in anhydrous tetrahydrofuran solution) may be flowed over a substrate for 15 min in an inert environment. The substrate may then be washed with one or more organic solvent. In some embodiments, the substrate may be exposed to a gas comprising the persistent carbene. For instance, gas phase deposition may be carried out by thermolysis of a persistent carbene precursor in a thermal evaporator.

In other cases, the substrate may be exposed to a persistent carbene precursor, wherein the persistent carbene precursor is a carbene associated with a protecting group. Physical or chemical treatment of the persistent carbene precursor comprising the protecting group can result in disassociation of the protecting group (e.g., the disassociated protecting group) and the persistent carbene. In some embodiments, at least a portion of the substrate may be exposed to a solution or composition comprising the persistent carbene precursor comprising a protecting group. The portion of the substrate exposed to the persistent carbene precursor may then be chemically or physically treated, thereby generating the persistent carbene, which can then associate with the substrate. In a non-limiting example, a substrate may be exposed to a solution comprising a persistent carbene precursor (e.g., carbon dioxide protected persistent carbene) and at least one solvent. The solvent may be removed prior to, subsequent with, or following the physical or chemical treatment. As another non-limiting example, a film comprising the persistent carbene precursor may be formed on the surface using techniques known in the art (e.g., spin-coating). In yet another example, a substrate may be exposed to a persistent carbene precursor (e.g., persistent carbene comprising a carbon dioxide protecting group) in the gas phase and the persistent carbene may be deposited on the surface using thermolysis in a thermal evaporator. Any suitable chemical or physical treatment may be employed. In some embodiments, the physical treatment comprises heating the substrate and/or persistent carbene precursor to an elevated temperature for a suitable period of time (e.g., as described herein). In certain embodiments, the physical treatment comprises an electrochemical, photochemical, and/or mechanical treatment. In some embodiments, the physical treatment may be performed in an inert environment (e.g., nitrogen gas, argon gas) and/or under reduced pressure. In some embodiments, the chemical treatment comprises exposing the substrate and/or persistent carbene precursor to a solution (e.g., comprising a silver(I) salt). In certain embodiments, chemical or physical treatment of a persistent carbene precursor (e.g., comprising a protecting group) may produce a persistent carbene and a non-associated species (e.g., the protecting group). In some instances, the protecting group associated with the persistent carbene precursor may be selected such that the disassociated protecting group does not substantially associate with the substrate and/or does not substantially interfere with the ability of the persistent carbene to associate with the substrate. Non-limiting examples of such species include carbon dioxide, alcohols, silver (I) salts, and chloroform.

Those of ordinary skill in the art will be able to determine suitable conditions under which to associate a substrate with a plurality of persistent carbenes and/or secondary compounds and/or for functionalizing the persistent carbenes and/or secondary compounds with a functional group. Conditions which may be varied include, but are not limited to, time of exposure, solvent, additives, temperature, and pressure.

In some embodiments, the temperature of conditions at which the associating or functionalizing step is conducted may be varied. As will be understood by those of ordinary skill in the art, generally, at lower temperatures, a reaction proceeds at a slower rate as compared to a higher temperature, however, the amount of side products produced generally increases at higher temperatures. Using simple screening tests, those of ordinary skill in the art will be able to select an appropriate temperature for associating a persistent carbene and/or a secondary compound with a substrate and functionalizing a persistent carbene and/or a secondary compound. In some embodiments, the associating or functionalizing steps may be conducted at room temperature, that is, between about 15° C. and about 25° C., between about 18° C. and about 22° C., or at about 20° C. In some cases, the associating or functionalizing steps may be conducted at temperatures greater than room temperature. For example, the temperature may be at least about 30° C., at least about 40° C., at least about 50° C., at least about 60° C., at least about 70° C., at least about 80° C., at least about 90° C., at least about 100° C., at least about 110° C., at least about 120° C., at least about 130° C., at least about 140° C., at least about 150° C., or greater. In some embodiments, the temperature is between about 60° C. and about 80° C., or between about 65° C. and about 75° C., or at about 70° C. In other embodiment, the temperature is between about 60° C. and about 150° C., or between about 65° C. and about 150° C.

The associating or functionalizing steps may be carried out for any suitable period of time. In some embodiments, the length of the associating step or functionalizing steps is determined by whether a substantial portion of the starting material has been transformed into the desired product, for example, by using simple screening tests known to those of ordinary skill in the art. For example, a small amount of the reaction mixture may be analyzed using liquid chromatography mass spectrometry. In some instances, a portion of the surface of a substrate may be analyzed by a surface sensitive microbalance or spectroscopic technique. In some cases, the associating or functionalizing steps are carried out for about 1 minute, about 2 minutes, about 3 minutes, about 5 minutes, about 10 minutes, about 15 minutes, about 20 minutes, about 30 minutes, about 45 minutes, about 60 minutes, about 2 hours, about 4 hours, about 8 hours, about 12 hours, about 18 hours, about 24 hours, or greater. In some cases, the period of time is between about 1 minute and about 24 hours, between about 1 minute and about 12 hours, between about 1 minute and about 6 hours, between about 1 minute and about 2 hours, between about 1 minute and about 15 minutes, between about 5 minutes and about 30 minutes, between about 5 minutes and about 15 minutes, or the like.

In some embodiments, the associating and functionalizing steps may employ one or more solvents. In some embodiments, the solvent is chosen such that the persistent carbene, secondary compounds, and/or compounds used for functionalization are at least partially soluble. Non-limiting examples of possible solvents include tetrahydrofuran, dimethylformamide, toluene, hexanes, xylene, diethyl ether, dioxane, dimethylsulfoxide, ethyl acetate, pyridine, triethylamine, or combinations thereof (e.g., 10:1 tetrahydrofuran:diethyl ether). In some embodiments, the solvent is an anhydrous solvent. In some embodiments, the methods may comprise at least one washing step. In some embodiments, the methods may be carried out in an inert atmosphere (e.g., in the absence of water and/or oxygen, and/or under an atmosphere or nitrogen or argon).

The substrate may be associated with any suitable number of persistent carbenes and/or secondary compounds. In some embodiments, the areal mass density of the persistent carbenes and/or secondary compounds on the surface may be determined using quartz crystal microbalance-dissipation (QCM-D) and converting the change in frequency to areal mass using a model (e.g., Sauerbrey equation, viscoelastic modeling, Voigt model). In some embodiments, the areal mass density of a monolayer of persistent carbenes on a flat surface may be greater than or equal to 50 $ng/cm^2$, greater than or equal to 100 $ng/cm^2$, greater than or equal to 200 $ng/cm^2$, greater than or equal to 400 $ng/cm^2$, greater than or equal to 700 $ng/cm^2$, greater than or equal to 1,000 $ng/cm^2$, or greater than or equal to 1,500 $ng/cm^2$. In some instances, the areal mass density of a monolayer of persistent carbenes on a flat surface may be less than about 2,000 $ng/cm^2$, less than about 1,500 $ng/cm^2$, less than about 1,000 $ng/cm^2$, less than about 700 $ng/cm^2$, less than about 400 $ng/cm^2$, less than about 200 $ng/cm^2$, or less than about 100 $ng/cm^2$. Combinations of the above-referenced ranges are also possible (e.g., greater than or equal to 50 $ng/cm^2$ and less than about 2,000 $ng/cm^2$). Other values of areal mass density are also possible.

Appropriate substrates and substrate materials for use with the methods and articles described herein are generally known and commercially available. Generally, the portion of the substrate to be associated with the at least one carbene comprises a material capable of associating with persistent carbenes. Non-limiting examples of suitable materials include metals (e.g., transition metals, lanthanides, actinides), metalloids (e.g., boron, silicon, germanium), organic material (e.g., graphite), binary compounds (e.g., metal halides, metal oxides, metal nitrides, metal selenides, metal sulfides), and combinations thereof. In certain cases, the substrate may comprise a carbon-based material (e.g., carbon nanotubes, graphite). In some embodiments, the substrate and/or the portion of the substrate to be associated with the at least one carbene comprises a metal (e.g., nickel, copper). In some embodiments, the portion of the substrate to be associated with the at least one carbene comprises a precious metal. In some embodiments, the substrate comprises gold. In some embodiments, the portion of the substrate to be associated with the at least one carbene comprises gold. In some embodiments, the substrate comprises a metal oxide. In some embodiments, the portion of the substrate to be associated with the at least one carbene comprises a metal oxide. In certain embodiments, the portion of the substrate to be associated with the at least one carbene comprises a metalloid. In certain embodiments, the portion of the substrate to be associated with the at least one carbene comprises silicon. In some embodiments, the portion of the substrate to be associated with the at least one carbene comprises an organic material. In some embodiments, the substrate comprises carbon nanotubes and/or graphite. In certain embodiments, the portion of the substrate to be associated with the at least one carbene comprises a non-metal. In certain embodiments, the portion of the substrate to be associated with the at least one carbene comprises cadmium selenide.

The substrate may have any suitable shape and size. For example, the substrate may be macroscopic (e.g., silicon wafer) or microscopic (e.g., nanoparticles, gold nanoparticles, cadmium selenide quantum dots, graphene, carbon nanotubes, atomic clusters, molecular clusters). In some embodiments, the substrate comprises a plurality of particles (e.g., microparticles, nanoparticles). Non-limiting examples of shapes include sheets, cubes, cylinders, hollow tubes, spheres, and the like. In some embodiments, the substrate is planar. In other embodiments, the substrate might not be planar. In some embodiments, the substrate may have a dimension (e.g., length, width, height, diameter) between about 0.001 µm and about 1,000,000 µm, between about 0.001 µm and about 1000 µm, between about 0.001 µm and about 10 µm, between about 0.001 µm and about 1 µm. In some instances, the substrate may have a dimension between about 1 µm and about 1,000,000 µm, between about 100 µm and about 1,000,000 µm, between about 1,000 µm and about 1,000,000 µm, between about 10,000 µm and about 1,000,000 µm, between about 100,000 µm and about 1,000,000 µm, or between about 10,000 µm and about 100,000 micrometers. In some cases, the maximum dimension of the substrate in one dimension may be at least about 0.01 µm, at least about 1 µm, at least about 10 µm, at least about 1 mm, at least about 5 cm, at least about 10 cm, or at least about 1 m, or greater. In some cases, the minimum dimension of the substrate in one dimension may be less than about 50 cm, less than about 10 cm, less than about 5 cm, less than about 1 cm, less than about 10 mm, less than about 1 mm, less than about 1 um, less than about 100 nm, or less than about 10 nm.

The substrate may comprise one or more materials. In some cases, the substrate may comprise a core material, wherein at least a portion of the core material comprises a material which is to be associated with the persistent carbene. In some embodiments, the core material may not be associated with the persistent carbene but may be substantially or partially coated with the secondary material that is to be associated with the persistent carbene. As a non-limiting example, in some cases, a secondary material may substantially cover a core material, and the carbenes may be associated with a portion of the secondary material.

Figure 4A:
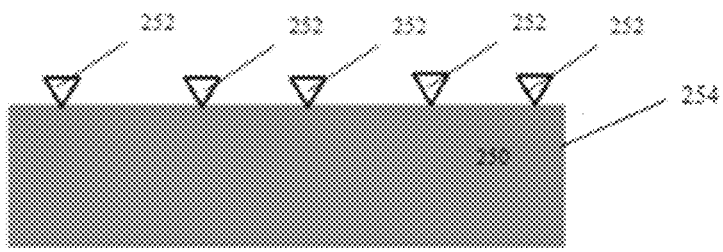
FIG. 4A-FIG. 4C show the association of persistent carbenes with various sides of a substrate, according to certain embodiments.
Figure 4B:
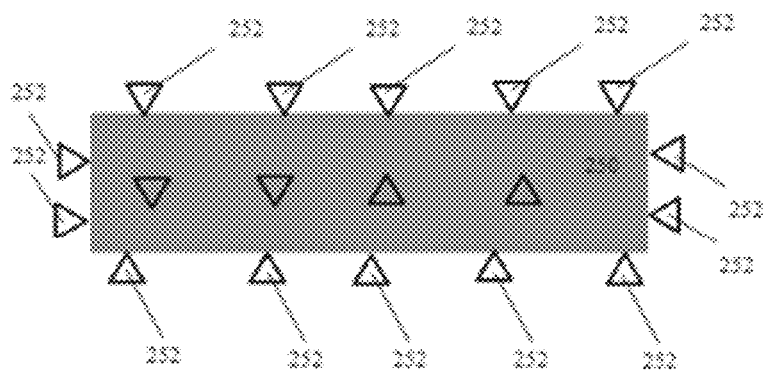
Figure 4C:
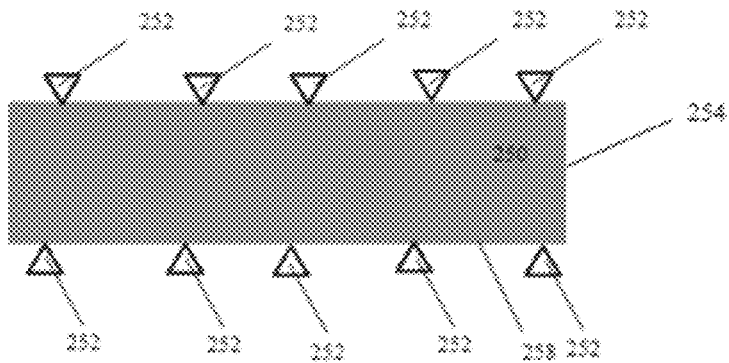

The persistent carbenes (and/or secondary compounds) may be associated with any portion of the substrate. In some embodiments, the portion of the substrate comprises substantially all of one side of the substrate. In some embodiments, the portion of the substrate comprises a portion of one side of the substrate. For example, FIG. 4A shows substrate 250 is associated with a plurality of persistent carbenes 252 on one side 254 of substrate 250. In some embodiments, the portion of the substrate comprises more than one side of the substrate. For example, FIG. 4B shows substrate 250 associated with a plurality of persistent carbenes 252 on two sides (e.g., 256 and 258) of substrate 250. In some embodiments, the portion of the substrate comprises substantially all of the sides the substrate. For example, FIG. 4C shows substrate 250 associated with a plurality of persistent carbenes 252 on all of the sides of substrate 250. In some embodiments, the persistent carbenes (and/or secondary compounds) may be associated with a portion of the substrate which is not an outer surface of the substrate (e.g., within a pore).

In some embodiments, a persistent carbene or other secondary materials associated with the substrate may each comprise at least one functionalizable group. The functionalizable group may be functionalized after association with a substrate, for example, by exposure to a compound comprising a functional group. The term "functionalizable group," as used herein, refers to a group or moiety which is capable of being chemically modified (e.g., via chemical reaction with a compound comprising a functional group). In some embodiments, the functionalizable group is a group or moiety which is capable of being chemically modified with a functional group via formation of a bond (e.g., covalent bond, non-covalent bond, etc.) or interaction (e.g., chemical or biological interaction) between the functionalizable group and the functional group. Functionalizable groups will be selected readily, by those of ordinary skill in the art, based upon the description provided herein and knowledge in the art.

Figure 5A:
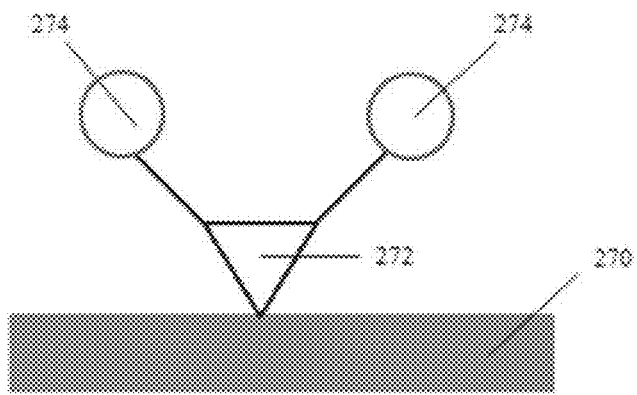
FIG. 5A and FIG. 5B show the functionalization of persistent carbenes associated with a substrate, according to one set of embodiments.
Figure 5B:
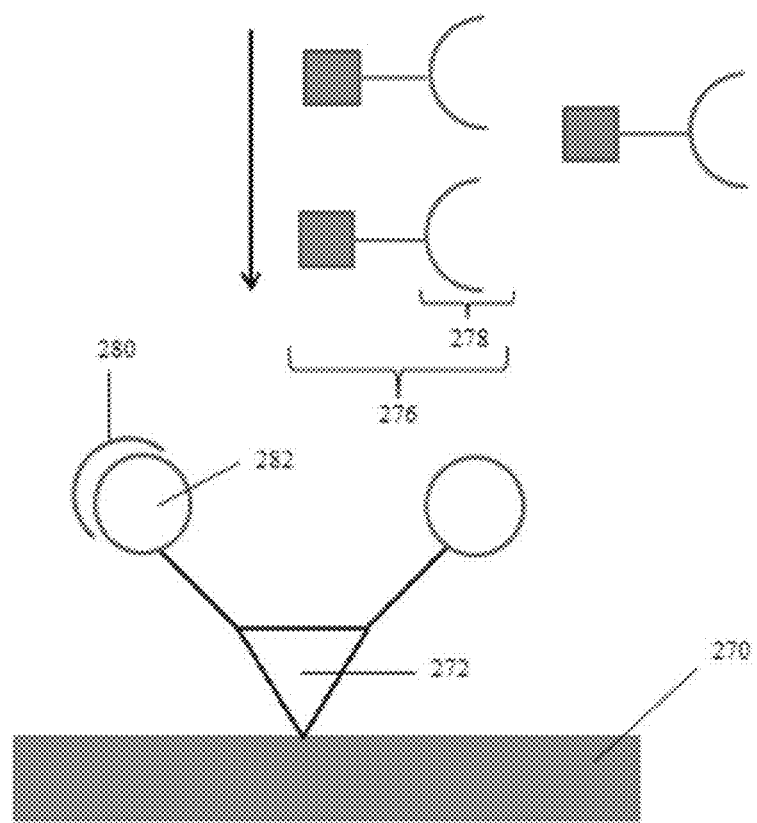

For example, as shown in FIG. 5A, substrate 270 is provided associated with persistent carbene 272 comprising two functionalizable groups 274. Upon exposure to a plurality of compounds 276 each comprising a functional group 278, a chemical reaction can occur between at least a portion of the functionalizable groups and the compounds comprising the functional groups, which results in that portion of functionalizable groups being associated with a functional group, as shown in FIG. 5B (e.g., functional group 280 is associated with functionalizable group 282). In some embodiments, only a portion of the functionalizable groups are functionalized. In other embodiments, all or substantially all of the functionalizable groups are functionalized.

In some embodiments, functionalizing the persistent carbene may comprise forming a covalent bond between the functionalizable group and the functional group (e.g., provided via a compound comprising the functional group) via a chemical reaction. For instance, in certain embodiments, the chemical reaction may be a coupling reaction, a polymerization reaction, or a click chemistry reaction. Those of ordinary skill in the art will be aware of suitable chemical reactions between a functionalizable group and the functional group. Non-limiting examples of chemical reactions include addition reactions (including cycloaddition), oxidation reactions, reduction reactions, elimination reactions, substitution reactions, rearrangement reactions, polymerization reactions, transition-metal catalyzed coupling or cross-coupling reactions, and olefin metathesis. In some embodiments, the reaction is not a click chemistry reaction. It should be understood that covalent bonds may be formed by other types of reactions, as known to those of ordinary skill in the art, using functionalizable groups described herein.

In some cases, functionalizing the functionalizable group comprises performing ring-opening metathesis. For instance, in some embodiments, a substrate associated with persistent carbene comprising an alkenyl functionalizable group may be exposed to a catalyst precursor (e.g., a precursor to a transition metal carbene complex, Grubbs' catalyst, Schrock catalyst). In some instances, the catalyst precursor may be a precursor to a $3^{rd}$ generation Grubb's catalyst comprising ruthenium. The catalyst precursor may reaction with the alkyenyl functionalizable group, thereby forming a catalytic complex associated with the persistent carbene. The catalytic complex may be used to initiate a chemical reaction such a polymerization reaction. In some such cases, the catalytic complex may be used to form a polymer associated with the persistent carbene via a ring-open metathesis polymerization reaction.

In some embodiments, functionalizing the functionalizable group comprises performing click chemistry (i.e., copper-catalyzed cycloaddition of azides and alkynes). For instance, in certain embodiments, a substrate associated with persistent carbene comprising an alkynyl or azide functionalizable group may be exposed to a compound comprising an azide or alkyne, respectively. The alkyne and azide may undergo copper-catalyzed cycloaddition of azides and alkynes to form a triazole ring (e.g., via reaction of the persistent carbene to the compound). In some instances, the compound may also comprise groups, which affect the solubility of the compound. For example, the compound may comprise ethylene glycol groups, which allow the compound to be water soluble. In some embodiments, forming a covalent bond between the persistent carbene and a compound may change the solubility of the compound. In one example, functionalizing a persistent carbene with a group comprising water soluble groups (e.g., ethylene glycol) may increase the water solubility of the compound.

In some cases, functionalizing the functionalizable group may comprise forming a non-covalent bond with another molecule (e.g., via hydrogen-bonds, ionic bonds, dative bonds, Van der Waals interactions, or the like). In some embodiments, the functionalizable group may form a hydrogen-bond with another molecule. Functionalizable groups capable of forming hydrogen-bonds include hydrogen-bond donors and acceptors. Those of ordinary skill in the art will be able to identify hydrogen-bond donors and acceptors suitable for use in the present invention. For example, a hydrogen-bond donor may comprise at least one hydrogen atom capable of associating with a pair of electrons on a hydrogen-bond acceptor to form the hydrogen bond. In some cases, the functionalizable groups may comprise one or more hydrogen-bond donor/acceptor moieties. Other examples of functionalizable groups which may form hydrogen bonds include carbonyl groups, amines, hydroxyls, and the like.

In some cases, the functionalizable groups may comprise an electron-rich or electron-poor moiety, wherein functionalizing the functionalizable group may comprise forming an electrostatic interaction with another molecule.

In some embodiments, at least one functionalizable group may be functionalized via a biological binding event (e.g., between complementary pairs of biological molecules). For example, a functionalizable group may comprise an entity such as biotin that specifically binds to a complementary entity, such as avidin or streptavidin, on another molecule. Other examples of interactions that occur between pairs of biological molecules including proteins, nucleic acids, glycoproteins, carbohydrates, hormones, and the like. Specific examples include an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair. Biological interactions between structure comprising a persistent carbene and the substrate suitable for use in the embodiments described herein can be selected readily, by those of ordinary skill in the art, based upon the description herein as their function, examples of such biological interactions, and knowledge herein and in the art as to simple techniques for identifying suitable chemical interactions.

It should be understood that while much of the discussion herein focuses on functionalizing the persistent carbenes and/or secondary compounds following association of the persistent carbenes and/or secondary compounds with the substrate, this is by no means limiting, and in some embodiments, the functionalization may occur prior to associating the persistent carbenes and/or secondary compounds with the substrate.

In general, a secondary compound may be any compound that comprises a moiety capable to associate with the substrate. For example a secondary compound may comprise a thiol. Non-limiting examples of moieties that a secondary compound may comprise include thiol, thioether, selenol, dithiocarbamate, dithioate, dithiophosphinate, phosphonate, carboxylic acid and carboxylate group, amine and amide group, pyridine, phosphine, alcohol and alkoxide, nitrile, isocyanide, alkyl, alkenyl, aryl, and alkynyl groups.

In some embodiments, the association of a plurality of compounds with a substrate via different association methods (e.g., via a persistent carbene, a thiol, a biological interaction) may be advantageous. In some embodiments, the different association methods may be manipulated to control certain properties of the substrate (e.g., surface chemistry). For instance, in some embodiments, different association methods may allow the surface chemistry of a substrate to be controlled. For instance, in certain embodiments, the use of different association methods may allow the placement of compounds on the substrate to be controlled. For example, a substrate may comprise regions that may not associate with a thiol and may associate with the persistent carbene. In some instances, the use of different association methods may allow controlled placement of compounds anchored to the surface through functionalization of the persistent carbene and secondary compound. In some embodiments, the use of different association methods may allow the concentration of compounds associated with the substrate to be controlled.

In some embodiments, the methods described herein may be utilized to prepare articles. In some embodiments, an article comprises a substrate having a surface, wherein at least a portion of the surface is associated with a plurality of persistent carbenes and a plurality of secondary compounds, wherein the plurality of the persistent carbenes and the plurality of the secondary compounds are functionalizable. Articles described herein and/or made by the methods described herein may find use in various applications including, but not limited to, electronics, sensing, microfabrication, nanotechnology, biomimetic, and drug delivery. It should be understood that the following exemplary applications are non-limiting.

Figure 6A:
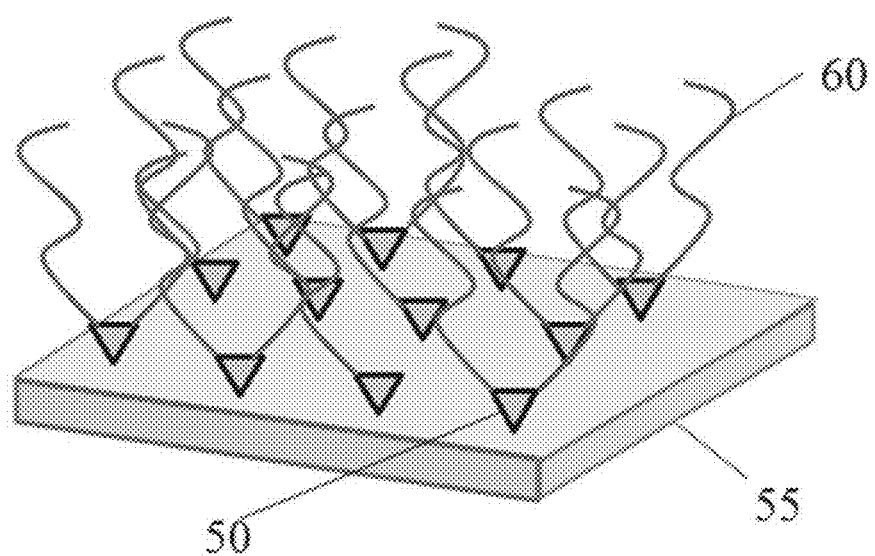
FIG. 6A-FIG. 6C show various applications of functionalized persistent carbenes associated with a substrate, according to certain embodiments.
Figure 6B:
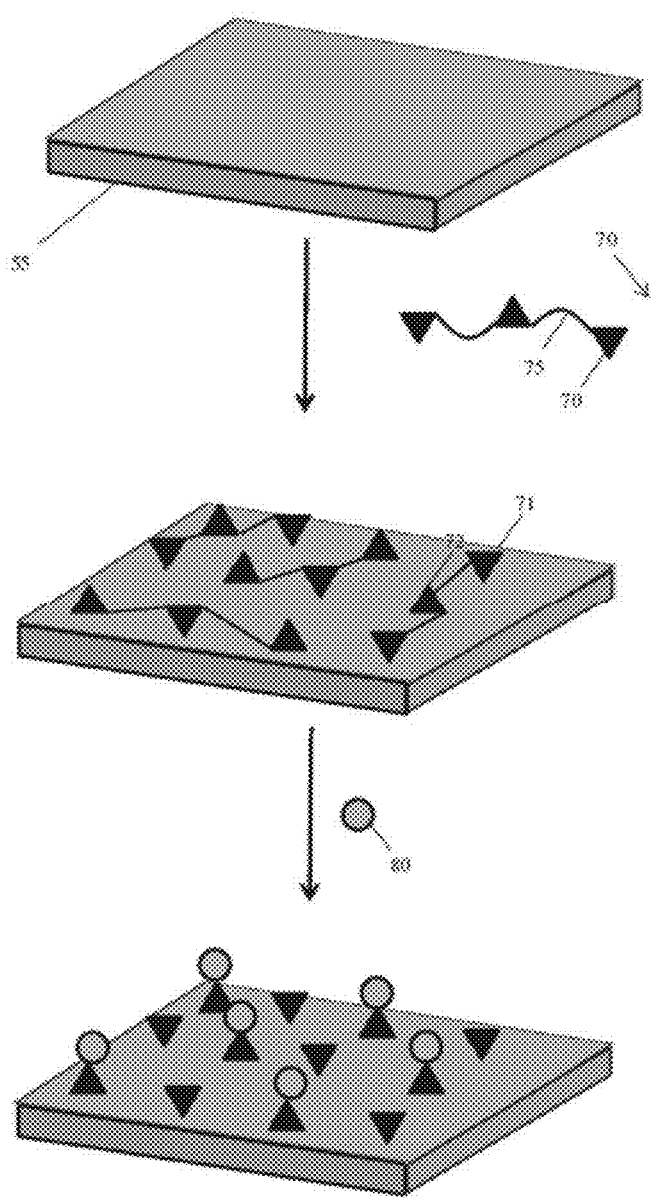
Figure 6C:
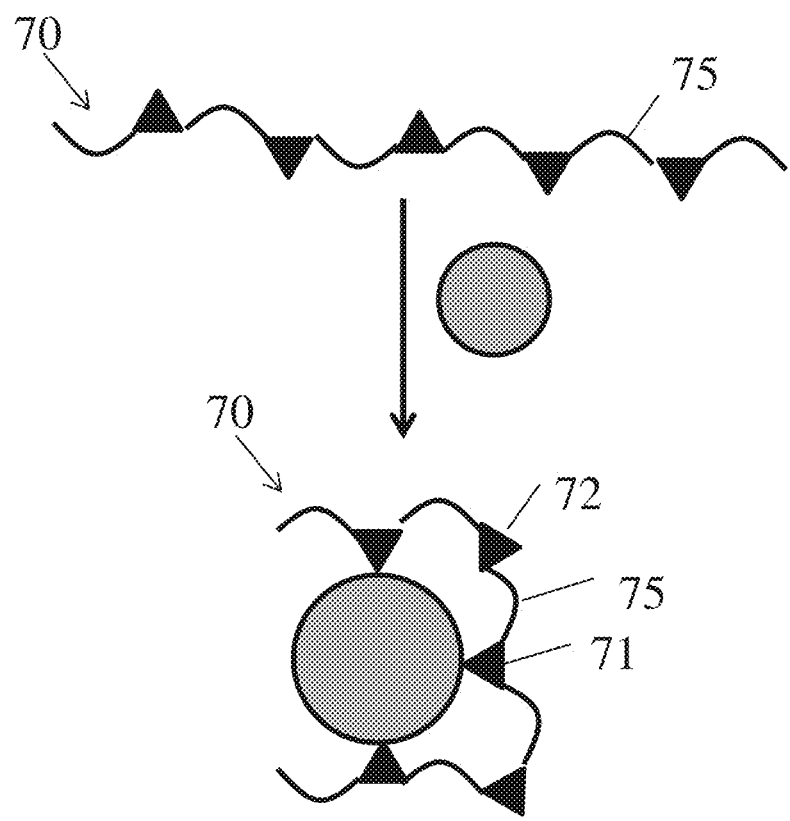

FIG. 6 shows non-limiting examples of articles. In one example, as shown in FIG. 6A, a plurality of persistent carbenes may be associated with substrate 55. The plurality of persistent carbenes may form a monolayer on the surface of the substrate. At least a portion of the at least one functionalizable group of the persistent carbene may be functionalized with polymer 60. In some embodiments, the persistent carbene serve to anchor polymer 60 to the surface of the substrate. In some cases, anchoring the polymers to the substrate may serve to stabilize the substrate in its environment. In certain embodiments, as shown in FIG. 6C, the substrate may be particle 65 (e.g., gold nanoparticles). Structure 70 may comprise a plurality of persistent carbene connected by linker 75. In certain embodiments, structure 70 may partially (or substantially completely) surround the surface of the substrate. In some instances, at least portion of the persistent carbenes 71 may be associated with the nanoparticles by chemical bond, thereby increasing the stability of the nanoparticle in its environment. In some cases at least a portion of the persistent carbenes 72 in structure 70 may not be associated with the nanoparticles. These free carbene may associate with other molecules in the environment. In some embodiments, the particle (e.g., nanoparticle, microparticle) may be formed in the presence of a functionalized persistent carbenes, which acts to stabilize the particle during the formation process.

In another example, a substrate associated with persistent carbenes may be used as a sensor, e.g., for metal ions. As shown in FIG. 6B, structure 70 may comprise a plurality of persistent carbene connected via linker 75. Structure 70 may be associated with substrate 55, such that a monolayer is formed. In some instances, a portion of the plurality of persistent carbenes 71 (represented by triangles) may be associated with the substrate via chemical bonds. Another portion of the plurality of carbenes 72 may be free carbenes associated with the substrate due to physical proximity. The free carbenes may interact with molecules 80 in the environment (e.g., metal ions). In some instances, the substrate may be connected to or comprise electrical components such that the interaction of free carbenes with molecules in the environment may be detected. In certain embodiments, the free carbene may be used to sequester certain molecules in the environment.

In yet another example, a compound comprising a first and a second persistent carbene may be used to physically separate a first substrate from a second substrate. In some such embodiments, the compound may be used to prevent diffusion of atoms or molecules in the first (or second) substrate into the second (or first) substrate. For instance, the compound may be used to prevent the co-diffusion of metals (e.g., between gold or copper and nickel). In some embodiments, the first persistent carbene and second persistent carbene may be connected via a linker, as described herein. For example, the first substrate may be associated with the first persistent carbene and the second substrate may be associated with the second persistent carbene, wherein the first carbene and the second carbene are joined by a linker. In some cases, the first substrate comprises a first type of material and the second substrate comprises a second type of material, wherein the first type of material and the second type of material are different. For instance, the first substrate may comprise a first metal and/or the second substrate may comprise a second metal. In general, the first and second substrate may be any substrate described herein and may be the same or different. In other embodiments, the first type of material and the second type of material are the same. In some instances, the first persistent carbene is associated with the first substrate via a first chemical interaction (e.g., covalent bond) and/or the second persistent carbene is associated with the second substrate via a second chemical interaction (e.g., covalent bond). In some such embodiments, the first persistent carbene is associate with the first substrate via its carbene moiety and/or the second persistent carbene is associate with the second substrate via its carbene moiety.

In some embodiments, a method of connecting the two substrates comprises associating a first persistent carbene with a first substrate, and associating a second persistent carbene with a second substrate, wherein the first persistent carbene and the second persistent carbene are associated via a linker. The compound comprises the first persistent carbene and the second persistent carbene, connected via the linker, may have any suitable structure, including the structures described below. In certain embodiments, the method comprises associating a plurality of compounds comprising a first persistent carbene and a second persistent carbene with the first substrate to form a layer (e.g., monolayer) of the compound on the first substrate (e.g., via association of the first persistent carbenes with the substrate) and then associating a second substrate with the second persistent carbenes. The second substrate may be associated with the second persistent carbenes by any suitable means known to those of skill of the art. For example, the second substrate may be applied by forming (e.g., via deposition) the second substrate on the layer of the compound, such that at least a portion of the atoms of the second substrate associate with the second persistent carbenes.

In some embodiments, the persistent carbenes and/or secondary compounds form a monolayer on a portion of the surface of the substrate. The term monolayer is given its ordinary meaning in the art and refers to a layer that is substantially one molecule or one atom thick (e.g., one molecule of persistent carbene thick). Although substantially one layer thick, some variation on the order of zero to two molecules is within the scope of the disclosed embodiments.

The persistent carbenes for use with the methods and articles described herein will now be described in more detail. In addition, in some embodiments, compositions comprising the persistent carbenes or precursors thereof are provided. In addition, in some embodiments, solutions comprising the persistent carbenes or precursors thereof and at as least one solvent are also provided.

As used herein, the term "persistent carbene" is given its ordinary meaning in the art and refers to a stable carbene (e.g., demonstrating certain stability despite being a reactive intermediate. In some embodiments, the persistent carbene and/or persistent carbene precursor is cyclic. In some embodiments, the persistent carbene and/or persistent carbene precursor is acyclic. In some embodiments, the persistent carbene is an N-heterocyclic carbene ("NHC"). Non-limiting examples of persistent carbenes include diaminocarbenes (e.g., imidazol-2-ylidenes, benzimidazol-2-ylidenes, imidazolidin-2-ylidenes, triazol-5-ylidenes, diaminocarbene incorporated into a n-membered ring, where n is not five), heteroaminocarbenes (e.g., thiazol-2-ylidenes and oxazol-2-ylidenes), and mesoionic carbenes (e.g., imidazol-4-ylidenes, 1,2,3-triazol-4(or-5)-ylidenes, pyrazol-3 (or -4)-ylidenes, isoxazol-4-ylidenes, and thiazol-5-ylidenes).

As described herein, a persistent carbene or persistent carbene precursor may comprise at least one functionalizable group. In some embodiments, the functionalizable group comprises halo, optionally substituted alkenyl, optionally substituted alkynyl, epoxy, aryl, heteroaryl (e.g., pyridine), alkoxy, alcohol, acyl, oxyacyl, acyloxy (e.g., carboxylic acid, carboxylate), thio (e.g., thiol, thioether, dithiocarbamate, dithioate, dithiophosphinate), aminoacyl (e.g., amide), azide, phosphine (e.g., phosphonate), cyanate, isocyanate (e.g., isocyanide), isonitrile, amino, selenol, or nitrile. Functionalizable groups are described in more detail herein.

In some embodiments, a persistent carbene has a structure according to Formula (I):

(I)

wherein:
each X is independently selected from the group consisting of —NR—, —N=, —N⁺R=, —C—, —CR=, —CR$_2$—, —C⁻R—, —S—, and —O—;
each R is independently hydrogen, optionally substituted alkyl, optionally substituted alkylene, alcohol, halo, optionally substituted heteroalkyl, optionally substituted heteroalkylene, optionally substituted cycloheteroalkyl, optionally substituted cycloheteroalkylene, optionally substituted alkenyl, optionally substituted alkenylene, optionally substituted alkynyl, optionally substituted alkynylene, optionally substituted aryl, optionally substituted arylene, optionally substituted heteroaryl, optionally substituted heteroarylene, optionally substituted alkenyloxy, optionally substituted alkenyleneoxy, optionally substituted alkoxy, optionally substituted alkeneoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile, provided at least one R comprises a functionalizable group;
optionally, any two R may be joined to form a ring; and
optionally, any R may be substituted with a group forming a bond to a second persistent carbene.

In some embodiments, for a compound of formula (I):
each X is independently selected from the group consisting of —NR—, —N=, —N⁺R=, —C—, —CR=, —CR$_2$—, —C⁻R—, —S—, and —O—;
each R is independently hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile, provided at least one R comprises a functionalizable group;

optionally, any two R may be joined to form a ring; and
optionally, any R may be substituted with a group forming a bond to a second persistent carbene.

In some embodiments, the compound of Formula (I) has the structure:

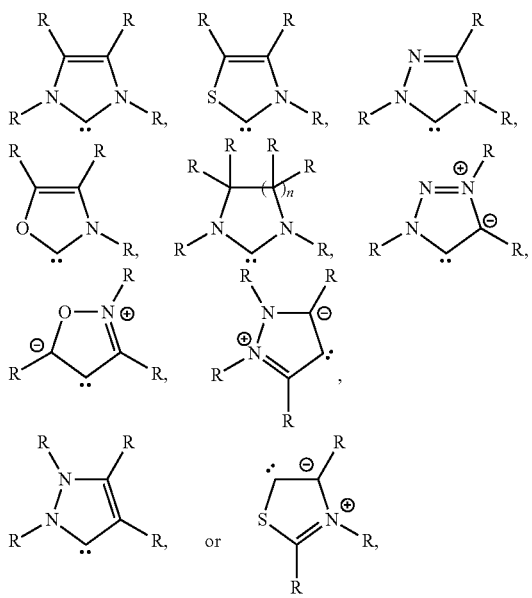

wherein n is 0, 1, 2, 3, 4, 5, or 6. In some embodiments at least one R is hydrogen. In some embodiments, at least one R is comprises a functionalizable group and each other R is hydrogen. In some embodiments, two R groups comprise a functionalizable group and each other R is hydrogen. In some embodiments, at least one R is aryl substituted with a functionalizable group (e.g., halo, —C≡CH, —CH═CH—CH$_3$, etc.).

In certain embodiments, any two R may be joined to form a ring. In some embodiments, the ring is a cycloalkyl or a heterocycle. In certain embodiments, the compound of Formula (I) has a structure:

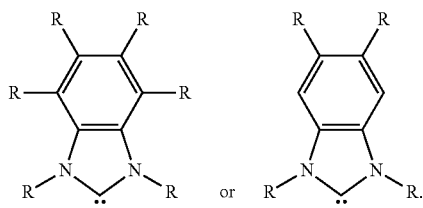

wherein R is as defined herein.

In certain embodiments, the at least one functionalizable group is halo (e.g., bromo, fluoro). In some instances, the at least one functionalizable group is substituted or unsubstituted alkynyl (e.g., —(CH$_2$)$_m$C≡CH, each H being optionally substituted, wherein m is 1, 2, 3, 4, etc.). In some cases, the at least one functionalizable group is —(CH$_2$)$_m$C≡C(CH$_2$)$_m$CH$_3$, each H being optionally substituted, wherein m is 1, 2, 3, 4, etc. In certain instances, the at least one functionalizable group is substituted or unsubstituted alkenyl (e.g., —(CH$_2$)$_m$CH═CH$_2$, each H being optionally substituted, wherein m is 1, 2, 3, 4, etc.). In some cases, the at least one functionalizable group is —(CH$_2$)$_m$CH═CH(CH$_2$)$_m$CH$_3$, each H being optionally substituted, wherein m is 1, 2, 3, 4, etc. In some embodiments, the at least one functionalizable group is substituted or unsubstituted heteroaryl (e.g., triazole). In some instances, the at least one functionalizable group is substituted or unsubstituted aryl (e.g., optionally substituted benzyl, optionally substituted phenyl). In some embodiments, more than one R may comprise a functionalizable group (e.g., any two R, any three R, any four R, any five R, any six R).

In some embodiments, the compound of Formula (I) has a structure:

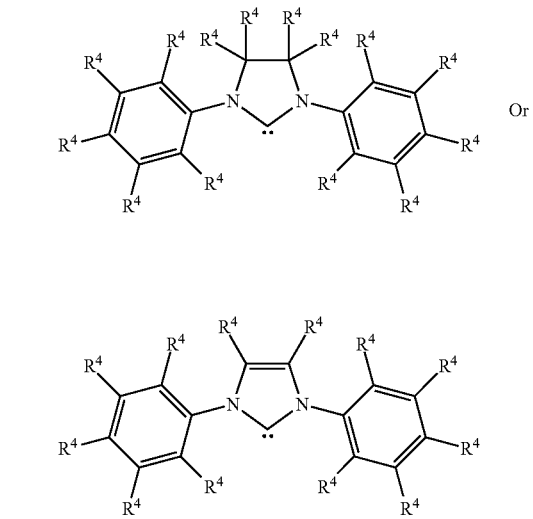

wherein each R$^4$ is independently hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile, provided at least one R$^4$ comprises a functionalizable group. In some embodiments, any two R$^4$ may be joined to form a ring. In some embodiments, any R$^4$ may be substituted with a group forming a bond to a second persistent carbene.

As described herein, in some embodiments, a compound of Formula (I) may be optionally bound to another persistent carbene. For example, in some embodiments, at least one R is associated with another persistent carbene via a linker or formation of a bond. In some cases, the compound of Formula (I) has a structure:

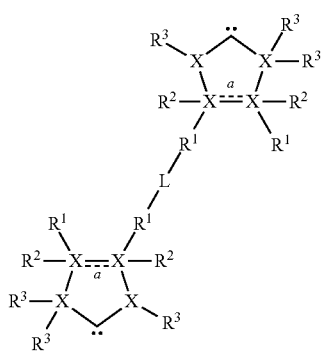

wherein each X is independently selected from the group consisting of —NR—, —N═, N⁺R═, —C—, —CR═, —CR₂—, —C⁻R—, —S—, and —O—, as described herein, wherein each R¹, R², and R³ are independently hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile, provided at least one R¹, R² or R³ comprises a functionalizable group;

optionally, wherein any two R¹ or R² may be joined to form a ring;

wherein $\overline{\overline{a}}$ a is a single or double bond, provided when $\overline{\overline{a}}$ a is a double bond each R² is absent; and wherein L is a linker.

In some cases, the compound of Formula (I) has a structure:

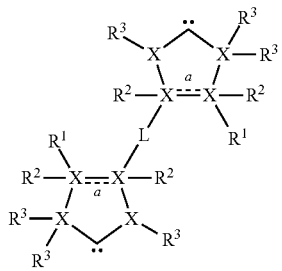

wherein each X is independently selected from the group consisting of —NR—, —N═, N⁺R═, —C—, —CR═, —CR₂—, —C⁻R—, —S—, and —O—, as described herein, wherein each R¹, R², and R³ are independently hydrogen, optionally substituted alkyl, optionally substituted alkylene, alcohol, halo, optionally substituted heteroalkyl, optionally substituted heteroalkylene, optionally substituted cycloheteroalkyl, optionally substituted cycloheteroalkylene, optionally substituted alkenyl, optionally substituted alkenylene, optionally substituted alkynyl, optionally substituted alky- nylene, optionally substituted aryl, optionally substituted arylene, optionally substituted heteroaryl, optionally substituted heteroarylene, optionally substituted alkenyloxy, optionally substituted alkenyleneoxy, optionally substituted alkoxy, optionally substituted alkeneoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile, provided at least one R¹, R² or R³ comprises a functionalizable group;

optionally, wherein any two R¹ or R² may be joined to form a ring;

wherein $\overline{\overline{a}}$ a is a single or double bond, provided when $\overline{\overline{a}}$ a is a double bond each R² is absent; and wherein L is a linker.

In some embodiments, L comprises one or more of alkylene, alkenylene, alkynylene, arylene, heteroalkylene, heteroalkenylene, heteroalkynlene, heterocycle, cycloalkylene, or heteroarylene. In some embodiments, L comprises one or more of alkylene, alkenylene, alkynylene, arylene, heteroalkylene, or heteroarylene. In some embodiments, L comprises at least one alkynylene. In some embodiments, L comprises alkynylene, alkylene, alkylene-arylene-alkylene, alkynylene-arylene-alkynylene, alkylene-arylene-arylene-alkylene, or arylene. In some embodiments, L comprises —CH═CH-phenylene-CH═CH—. In some embodiments, L comprises phenylene. In some embodiments, L comprises —CH═CH—. In some embodiments, L comprises alkylene. In some embodiments, L comprises —(CH₂)ₘ—, wherein m is 1, 2, 3, 4, 5, 6, 7, 8, etc.

In some embodiments, a compound of Formula (I) bound to another persistent carbene precursor, e.g., via a linker or a bond, may be used to associate a first and second substrate.

In some embodiments, the compound of Formula (I) has a structure:

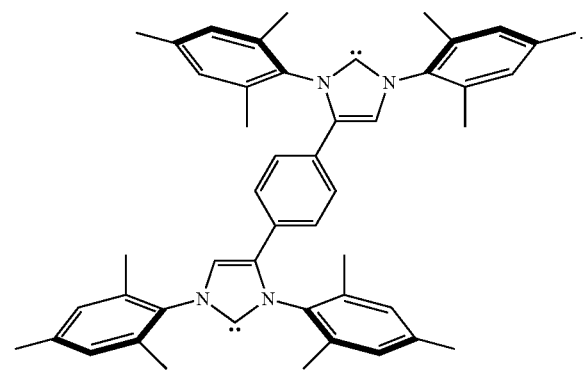

In some embodiments, a compound of Formula (I) may be selected from the group consisting of:

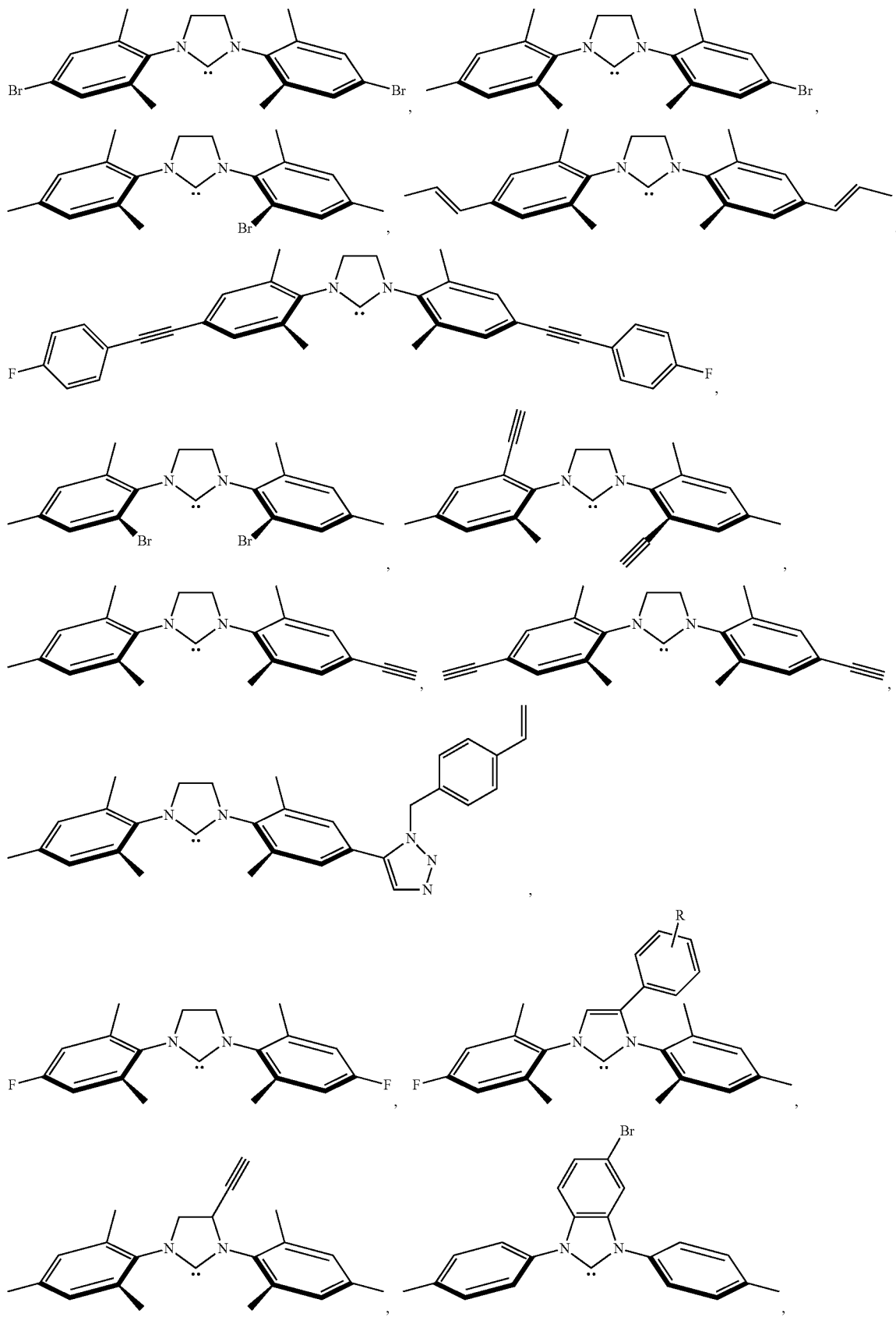

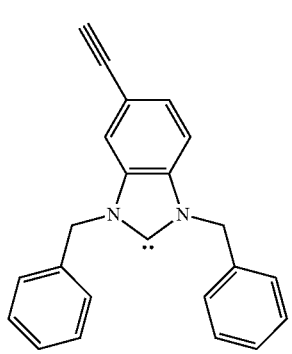
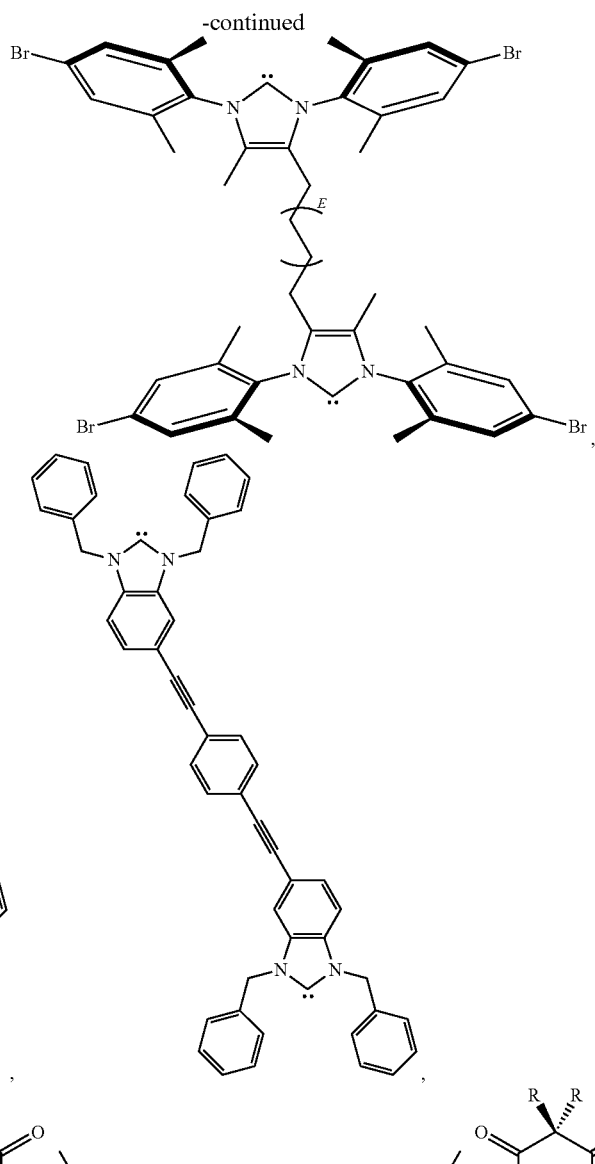
,
wherein m is 0, 1, or 2.
In some embodiments, the persistent carbene is acyclic. Non-limiting examples of acyclic persistent carbenes include the following:
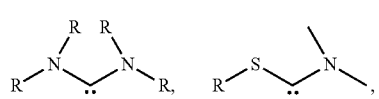
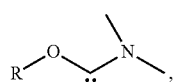
,
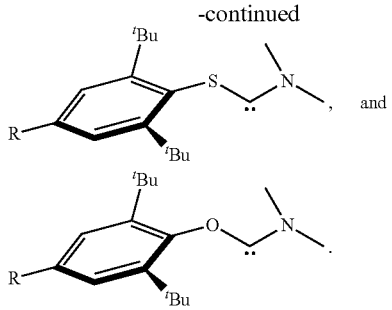
In some embodiments, at least one R comprises a functionalizable group. Examples of suitable R groups and functionalizable groups are described herein in connection with a compound of Formula (I). Those of ordinary skill in the art will be able to apply the teachings and description herein with respect to cyclic persistent carbenes to the acyclic persistent carbenes described herein.

In some embodiments, the persistent carbene may be derived from a persistent carbene precursor. In some embodiments, compositions or solutions comprising a persistent carbene precursor are provided. The precursor may be converted into a carbene by chemical reaction, such as deprotonation, decarboxylation, dehydration, etc. (e.g., by exposure to a base, by exposure to heat, etc., as described herein).

In some embodiments, the precursor to the persistent carbene of formula (I) comprises a compound of Formula (II):

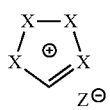

(II)

wherein:

each X is independently selected from the group consisting of —NR—, —N=, N$^+$R=, —C—, —CR=, —CR$_2$—, —C$^-$R—, —S—, and —O—;

each R is independently hydrogen, optionally substituted alkyl, optionally substituted alkylene, alcohol, halo, optionally substituted heteroalkyl, optionally substituted heteroalkylene, optionally substituted cycloheteroalkyl, optionally substituted cycloheteroalkylene, optionally substituted alkenyl, optionally substituted alkenylene, optionally substituted alkynyl, optionally substituted alkynylene, optionally substituted aryl, optionally substituted arylene, optionally substituted heteroaryl, optionally substituted heteroarylene, optionally substituted alkenyloxy, optionally substituted alkenyleneoxy, optionally substituted alkoxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile, provided at least one R comprises a functionalizable group;

optionally, any two R may be joined to form a ring; and optionally, any R may be substituted with a group forming a bond to a second persistent carbene precursor; and Z$^-$ is a counter anion. Examples of suitable R groups and functionalizable groups are described herein in connection with a compound of Formula (I).

In some embodiments, for a compound of Formula (II):

each X is independently selected from the group consisting of —NR—, —N=, —N$^+$R=, —C—, —CR=, —CR$_2$—, —C$^-$R—, —S—, and —O—;

each R is independently hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile, provided at least one R comprises a functionalizable group;

optionally, any two R may be joined to form a ring; and optionally, any R may be substituted with a group forming a bond to a second persistent carbene precursor; and Z$^-$ is a counter anion. Examples of suitable R groups and functionalizable groups are described herein in connection with a compound of Formula (I).

In some embodiments, the compound of Formula (II) has the structure:

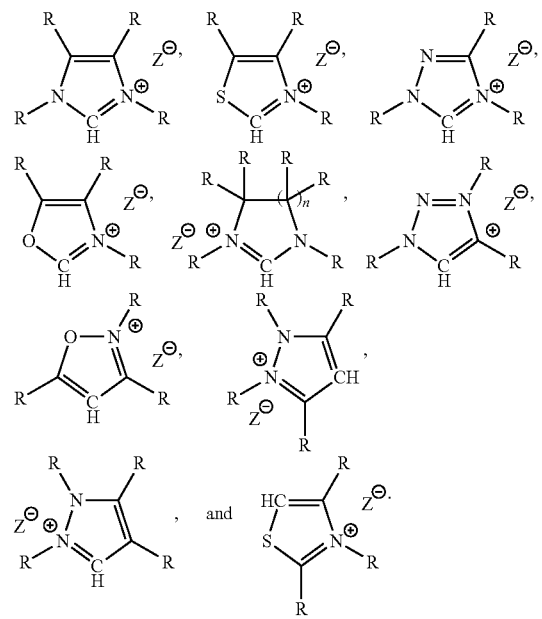

In certain embodiments, for a compound of Formula (II) any two R may be joined to form a ring. In some embodiments, the ring is a cycloalkyl or a heterocycle. In certain embodiments, the compound of Formula (II) has a structure:

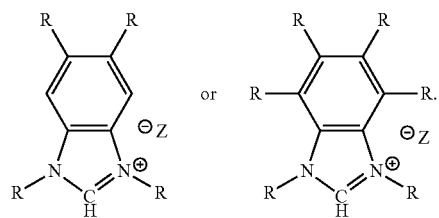

In some embodiments, the compound of Formula (II) has a structure:

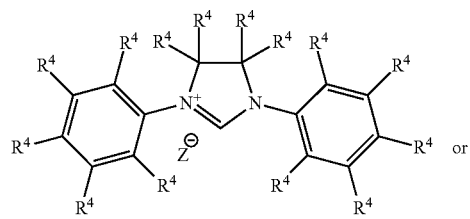

-continued

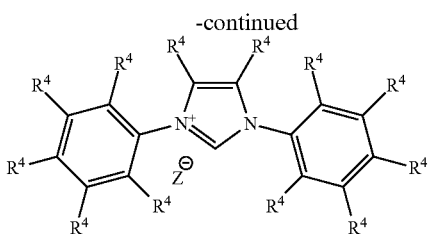

wherein each R⁴ and Z⁻ is as described herein.

As described herein, in some embodiments, a compound of Formula (II) may be bound to another persistent carbene precursor. For example, at least one R may be associated with another persistent carbene precursor via a linker or a bond.

In some such cases, the compound of Formula (II) has a structure:

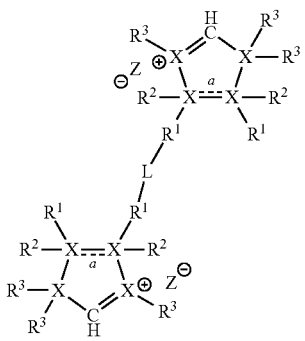

wherein each X is independently of —NR—, —N═, N⁺R═, —C—, —CR═, —CR₂—, —C⁻R—, —S—, and —O—, as described herein, wherein each $R^1$, $R^2$, and $R^3$ are independently hydrogen, optionally substituted alkyl, optionally substituted alkylene, alcohol, halo, optionally substituted heteroalkyl, optionally substituted heteroalkylene, optionally substituted cycloheteroalkyl, optionally substituted cycloheteroalkylene, optionally substituted alkenyl, optionally substituted alkenylene, optionally substituted alkynyl, optionally substituted alkynylene, optionally substituted aryl, optionally substituted arylene, optionally substituted heteroaryl, optionally substituted heteroarylene, optionally substituted alkenyloxy, optionally substituted alkenyleneoxy, optionally substituted alkoxy, optionally substituted alkyleneoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile, provided at least one $R^1$, $R^2$ or $R^3$ comprises a functionalizable group;

optionally, wherein any two $R^1$ or $R^2$ may be joined to form a ring;

wherein a̿ is a single or double bond, provided when a̿ is a double bond each $R^2$ is absent; and wherein L is a linker.

In some such cases, the compound of Formula (II) has a structure:

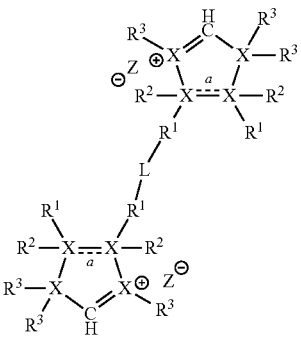

wherein each X is independently of —NR—, —N═, N⁺R═, —C—, —CR═, —CR₂—, —C⁻R—, —S—, and —O—, as described herein, wherein each $R^1$, $R^2$, and $R^3$ are independently hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile, provided at least one $R^1$, $R^2$ or $R^3$ comprises a functionalizable group;

optionally, wherein any two $R^1$ or $R^2$ may be joined to form a ring;

wherein a̿ is a single or double bond, provided when a̿ is a double bond each $R^2$ is absent; and wherein L is a linker.

In some cases, the compound of Formula (II) has a structure:

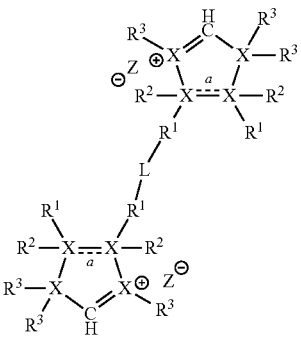

wherein each X is independently of —NR—, —N═, N⁺R═, —C—, —CR═, —CR₂—, —C⁻R—, —S—, and —O—, as described herein, wherein each $R^1$, $R^2$, and $R^3$ are independently hydrogen, optionally substituted alkyl, optionally substituted alkylene, alcohol, halo, optionally substituted heteroalkyl, optionally substituted heteroalkylene, optionally substituted cycloheteroalkyl, optionally substituted cycloheteroalkylene, optionally substituted alkenyl, optionally substituted alkenylene, optionally substituted alkynyl, optionally substituted alkynylene, optionally substituted aryl, optionally substituted arylene, optionally substituted heteroaryl, optionally substituted heteroarylene, optionally substituted alkenyloxy, optionally substituted alkenyleneoxy, optionally substituted alkoxy, optionally substituted alkeneoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile, provided at least one $R^1$, $R^2$ or $R^3$ comprises a functionalizable group;

optionally, wherein any two $R^1$ or $R^2$ may be joined to form a ring;

wherein a is a single or double bond, provided when a is a double bond each $R^2$ is absent; and wherein L is a linker.

In some embodiments, L comprises one or more of alkylene, alkenylene, alkynylene, arylene, heteroalkylene, heteroalkenylene, heteroalkynlene, heterocycle, cycloalkylene, or heteroarylene. In some embodiments, L comprises one or more of alkylene, alkenylene, alkynylene, arylene, heteroalkylene, or heteroarylene. In some embodiments, L comprises at least one alkynylene. In some embodiments, L comprises alkynylene, alkylene, alkylene-arylene-alkylene, alkynylene-arylene-alkynylene, alkylene-arylene-arylene-alkylene, or arylene. In some embodiments, L comprises —CH=CH-phenylene-CH=CH—. In some embodiments, L comprises phenylene. In some embodiments, L comprises —CH=CH—. In some embodiments, L comprises alkylene. In some embodiments, L comprises —$(CH_2)_m$—, wherein m is 1, 2, 3, 4, 5, 6, 7, 8, etc.

In some embodiments, a compound of Formula (II) bound to another persistent carbene precursor, e.g., via a linker or a bond, may be used to associate a first and second substrate.

In some embodiments, the compound of Formula (II) has a structure:

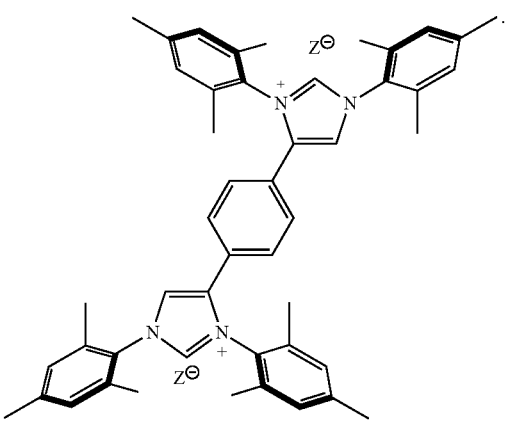

Those of ordinary skill in the art will be aware of suitable counter anions. In addition, those of ordinary skill in the art will be aware that the counter anion $Z^-$ may have a charge of less than −1 (e.g., −2, −3), and in such embodiments, each counter anion $Z^-$ may be associated with more than one molecule of persistent carbene precursors (e.g., a counter anion having a charge of −2 may be associated with two persistent carbene precursors). In some embodiments, the counter ion is a halide, tetrafluoroborate, tetraarylborate (e.g., tetrakis[3,5-bis(trifluoromethyl)phenyl]borate, tetraphenylborate, tetrakis(pentafluorophenyl)borate), perchlorate, chlorate, hexafluorophosphate, phosphate, hydrogen phosphate, dihydrogen phosphate, hydrogen sulfate, sulfate, sulfite, trifluoroacetate, toluenesulfonate, acetate, formate, citrate, ascorbate, mesylate (e.g., methanesulfonate), triflate (e.g., trifluoromethanesulfonate), tartrate, lactate, or benzoate.

In some embodiments, a compound of Formula (II) may be selected from a group consisting of:

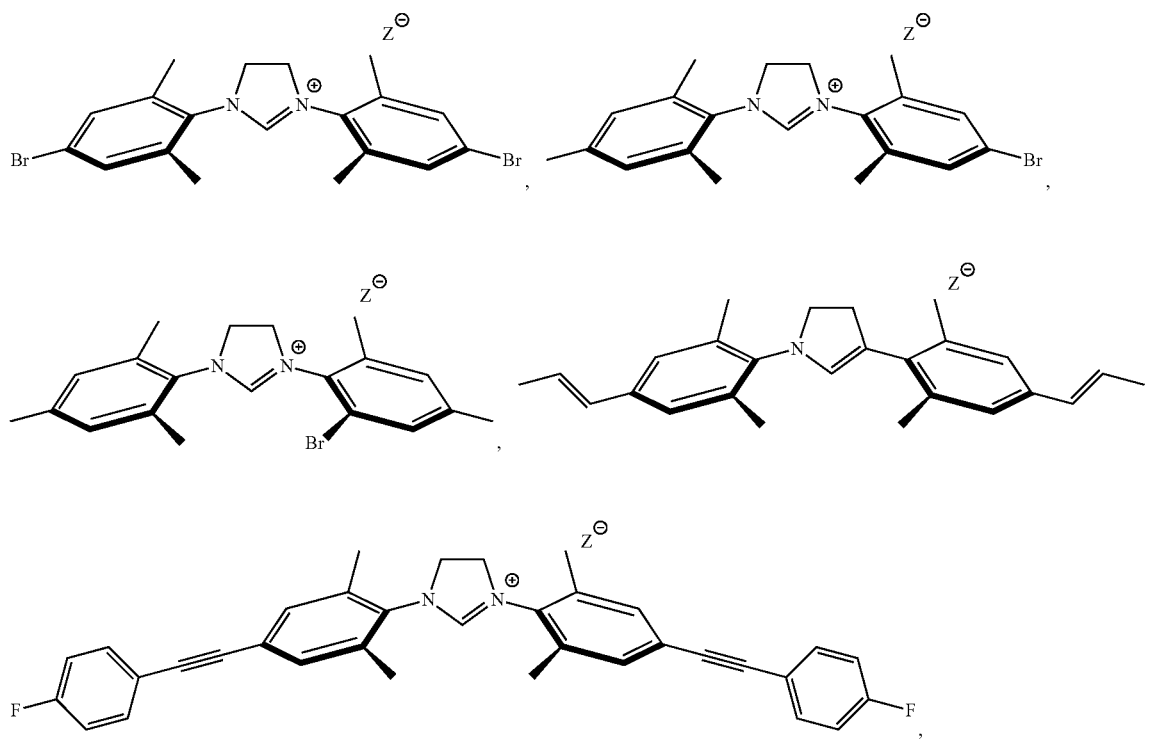

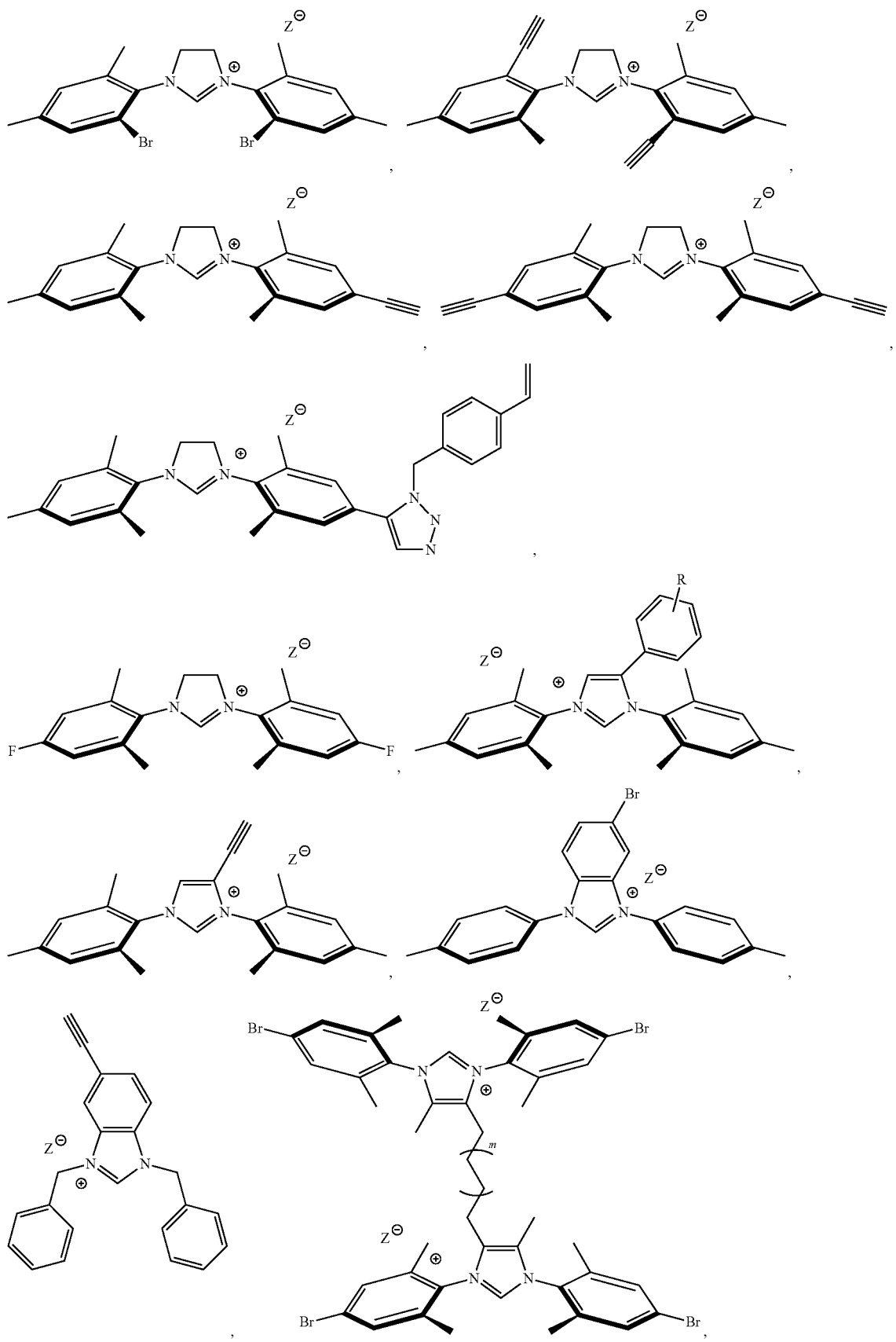

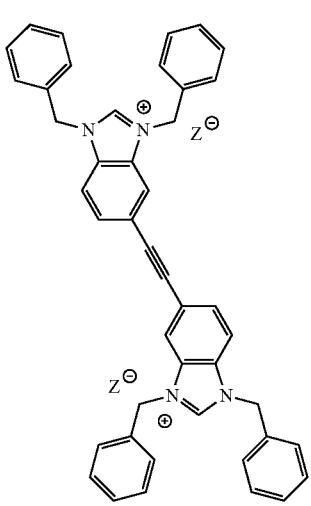
,

-continued

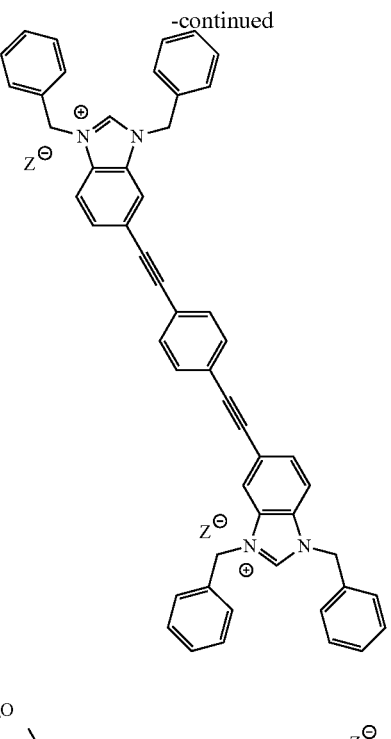
,

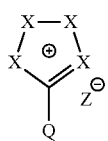

wherein m is 0, 1, or 2, R, and Z⁻ is as described herein.

In some embodiments, the precursor to the persistent carbene of Formula (I) comprises a compound of Formula (III):

$$\underset{Q}{\underset{|}{\overset{X-X}{\underset{X}{\overset{|}{\underset{\oplus}{X}}}\underset{Z^\ominus}{X}}}}\quad\text{(III)}$$

wherein:

each X is independently selected from the group consisting of —NR—, —N═, —N⁺R═, —C—, —CR═, —CR$_2$—, —C⁻R—, —S—, and —O—;

each R is independently hydrogen, optionally substituted alkyl, optionally substituted alkylene, alcohol, halo, optionally substituted heteroalkyl, optionally substituted heteroalkylene, optionally substituted cycloheteroalkyl, optionally substituted cycloheteroalkylene, optionally substituted alkenyl, optionally substituted alkenylene, optionally substituted alkynyl, optionally substituted alkynylene, optionally substituted aryl, optionally substituted arylene, optionally substituted heteroaryl, optionally substituted heteroarylene, optionally substituted alkenyloxy, optionally substituted alkenyleneoxy, optionally substituted alkoxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile, provided at least one R comprises a functionalizable group;

optionally, any two R may be joined to form a ring; and
optionally, any R may be substituted with a group forming a bond to a second persistent carbene precursor;

Q is a protecting group; and

Z⁻ is a counter anion. Examples of suitable R groups and functionalizable groups are described herein in connection with a compound of Formula (I).

In some embodiments, for a compound of Formula (III):

each X is independently selected from the group consisting of —NR—, —N═, —N⁺R═, —C—, —CR═, —CR$_2$—, —C⁻R—, —S—, and —O—;

each R is independently hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile, provided at least one R comprises a functionalizable group;

optionally, any two R may be joined to form a ring; and
optionally, any R may be substituted with a group forming a bond to a second persistent carbene precursor;

Q is a protecting group; and

Z⁻ is a counter anion. Examples of suitable R groups and functionalizable groups are described herein in connection with a compound of Formula (I).

In some embodiments, Q is hydrogen, —CO$_2$, —CCl$_3$, halide, Ag(I) salt (e.g., AgX', wherein X' is a halide, nitrate, etc.), or alcohol (e.g., —OR', wherein R' is optionally substituted alkyl, optionally substituted aryl) Examples of suitable R groups and functionalizable groups are described herein in connection with a compound of Formula (I).

In some embodiments, the compound of Formula (III) has the structure:

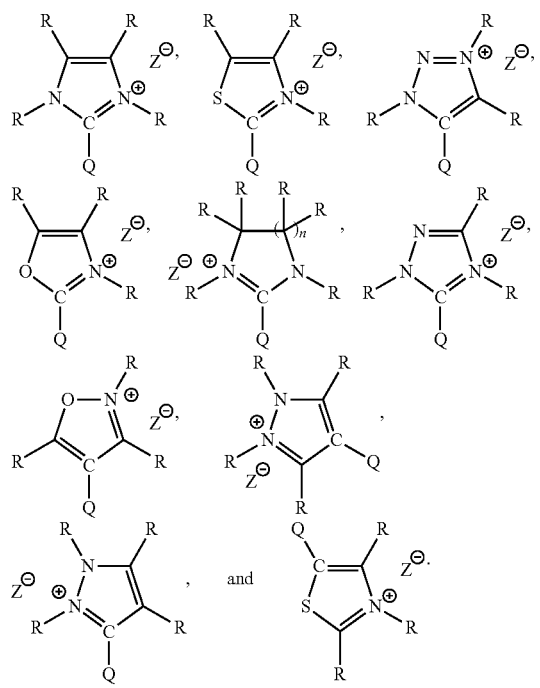

In certain embodiments, for a compound of Formula (III) any two R may be joined to form a ring. In some embodiments, the ring is a cycloalkyl or a heterocycle. In certain embodiments, the compound of Formula (III) has a structure:

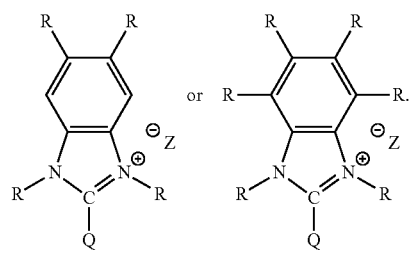

In some embodiments, the compound of Formula (III) has a structure:

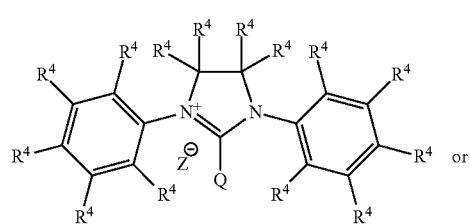

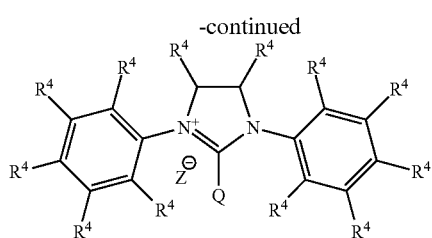

wherein each R$^4$ and Z$^-$ is as described herein.

As described herein, in some embodiments, a compound of Formula (III) may be bound to another persistent carbene precursor. For example, at least one R may be associated with another persistent carbene precursor via a linker or a bond. In some such cases, the compound of Formula (III) has a structure:

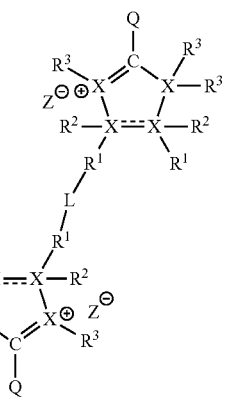

wherein each X is independently selected from a group consisting of —NR—, —N=, N$^+$R=, —C—, —CR=, —CR$_2$—, —C$^-$R—, —S—, and —O—, as described herein, wherein each Q is independently hydrogen, —CO$_2$, —CCl$_3$, halide, or —OR', as described herein;

wherein each R$^1$, R$^2$, and R$^3$ are independently hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocyanate, or nitrile, provided at least one R$^1$, R$^2$ or R$^3$ comprises a functionalizable group;

optionally, wherein any two R$^1$ or R$^2$ may be joined to form a ring;

wherein $\overline{\overline{a}}$ is a single or double bond, provided when $\overline{\overline{a}}$ is a double bond each R$^2$ is absent;

wherein L is a linker;

Q is a protecting group; and

Z$^-$ is a counter anion.

In some cases, the compound of Formula (III) has a structure:

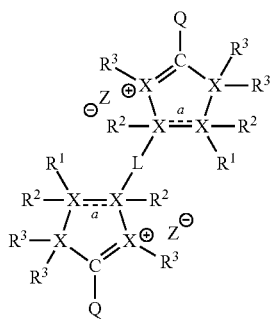

wherein each X is independently selected from a group consisting of —NR—, —N═, N⁺R═, —C—, —CR═, —CR₂—, —C⁻R—, —S—, and —O—, as described herein, wherein each Q is independently hydrogen, —CO₂, —CCl₃, halide, or —OR', as described herein;

wherein each $R^1$, $R^2$, and $R^3$ are independently hydrogen, optionally substituted alkyl, optionally substituted alkylene, alcohol, halo, optionally substituted heteroalkyl, optionally substituted heteroalkylene, optionally substituted cycloheteroalkyl, optionally substituted cycloheteroalkylene, optionally substituted alkenyl, optionally substituted alkenylene, optionally substituted alkynyl, optionally substituted alkynylene, optionally substituted aryl, optionally substituted arylene, optionally substituted heteroaryl, optionally substituted heteroarylene, optionally substituted alkenyloxy, optionally substituted alkenyleneoxy, optionally substituted alkoxy, optionally substituted alkeneoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile, provided at least one $R^1$, $R^2$ or $R^3$ comprises a functionalizable group;

optionally, wherein any two $R^1$ or $R^2$ may be joined to form a ring;

wherein $\overline{\overline{a}}$ is a single or double bond, provided when $\overline{\overline{a}}$ is a double bond each $R^2$ is absent;

wherein L is a linker; and wherein Z⁻ is a counter anion.

In some embodiments, L comprises one or more of alkylene, alkenylene, alkynylene, arylene, heteroalkylene, heteroalkenylene, heteroalkynlene, heterocycle, cycloalkylene, or heteroarylene. In some embodiments, L comprises one or more of alkylene, alkenylene, alkynylene, arylene, heteroalkylene, or heteroarylene. In some embodiments, L comprises at least one alkynylene. In some embodiments, L comprises alkynylene, alkylene, alkylene-arylene-alkylene, alkynylene-arylene-alkynylene, alkylene-arylene-arylene-alkylene, or arylene. In some embodiments, L comprises —CH═CH-phenylene-CH═CH—. In some embodiments, L comprises phenylene. In some embodiments, L comprises —CH═CH—. In some embodiments, L comprises alkylene. In some embodiments, L comprises —(CH₂)$_m$—, wherein m is 1, 2, 3, 4, 5, 6, 7, 8, etc.

In some embodiments, the compound of Formula (III) has a structure:

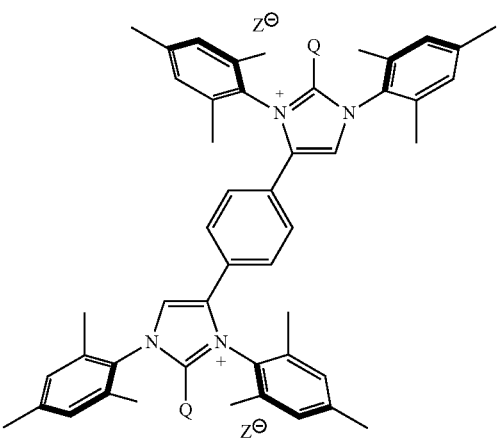

In some embodiments, a compound of Formula (III) bound to another persistent carbene precursor, e.g., via a linker or a bond, may be used to associate a first substrate and a second substrate. In some embodiments, regardless of whether the compound use to associate the first substrate and the second substrate is a compound of Formula (I), (II), or (III), the compound associated with a first substrate and the second substrate (e.g., via covalent bond) may have the structure:

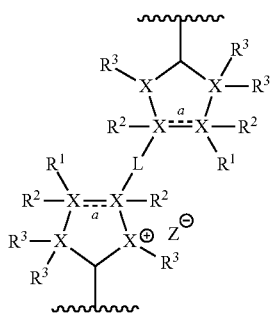

wherein each X is independently selected from a group consisting of —NR—, —N═, N⁺R═, —C—, —CR═, —CR₂—, —C⁻R—, —S—, and —O—, wherein each $R^1$, $R^2$, and $R^3$ are independently hydrogen, optionally substituted alkyl, optionally substituted alkylene, alcohol, halo, optionally substituted heteroalkyl, optionally substituted heteroalkylene, optionally substituted cycloheteroalkyl, optionally substituted cycloheteroalkylene, optionally substituted alkenyl, optionally substituted alkenylene, optionally substituted alkynyl, optionally substituted alkynylene, optionally substituted aryl, optionally substituted arylene, optionally substituted heteroaryl, optionally substituted heteroarylene, optionally substituted alkenyloxy, optionally substituted alkenyleneoxy, optionally substituted alkoxy, optionally substituted alkyleneoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile;

wherein $\overline{\overline{a}}$ is a single or double bond, provided when $\overline{\overline{a}}$ is a double bond each $R^2$ is absent;

wherein L is a linker; and wherein each 〰️ represent a bonds (e.g., covalent bond) to the first substrate or the second substrate. For the above compound, each of X, $R^1$, $R^2$, $R^3$, and L, may be as described herein.

Those of ordinary skill in the art will be aware of suitable counter anions. In addition, those of ordinary skill in the art will be aware that the counter anion $Z^-$ may have a charge of less than −1 (e.g., −2, −3), and in such embodiments, each counter anion $Z^-$ may be associated with more than one molecule of persistent carbene precursors (e.g., a counter anion having a charge of −2 may be associated with two persistent carbene precursors). In some embodiments, the counter ion is a halide, tetrafluoroborate, tetraarylborate (e.g., tetrakis[3,5-bis(trifluoromethyl)phenyl]borate, tetraphenylborate, tetrakis(pentafluorophenyl)borate), perchlorate, chlorate, hexafluorophosphate, phosphate, hydrogen phosphate, dihydrogen phosphate, hydrogen sulfate, sulfate, sulfite, trifluoroacetate, toluenesulfonate, acetate, formate, citrate, ascorbate, mesylate (e.g., methanesulfonate), triflate (e.g., trifluoromethanesulfonate), tartrate, lactate, or benzoate.

In some embodiments, a compound of Formula (III) may be selected from a group consisting of:

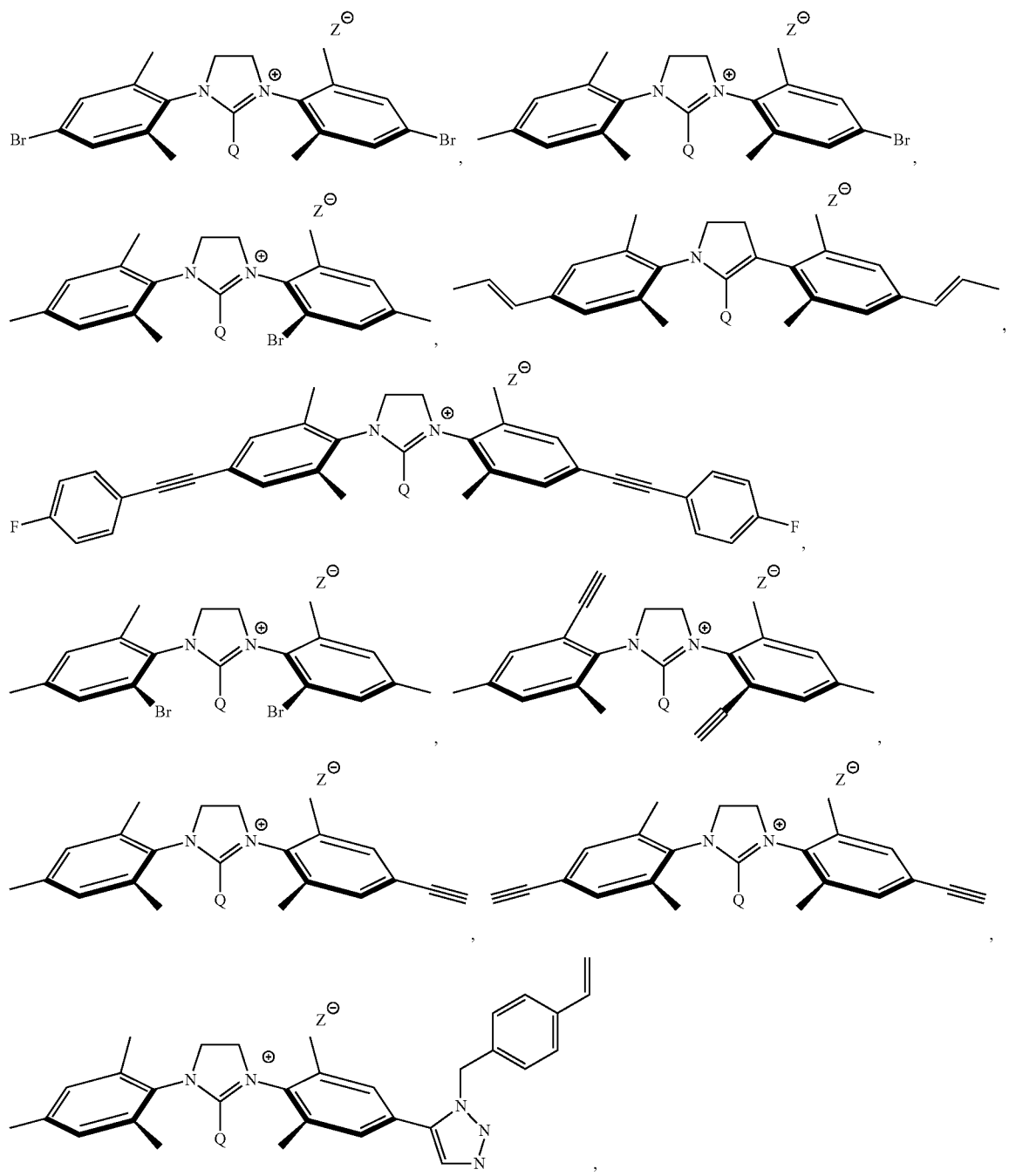

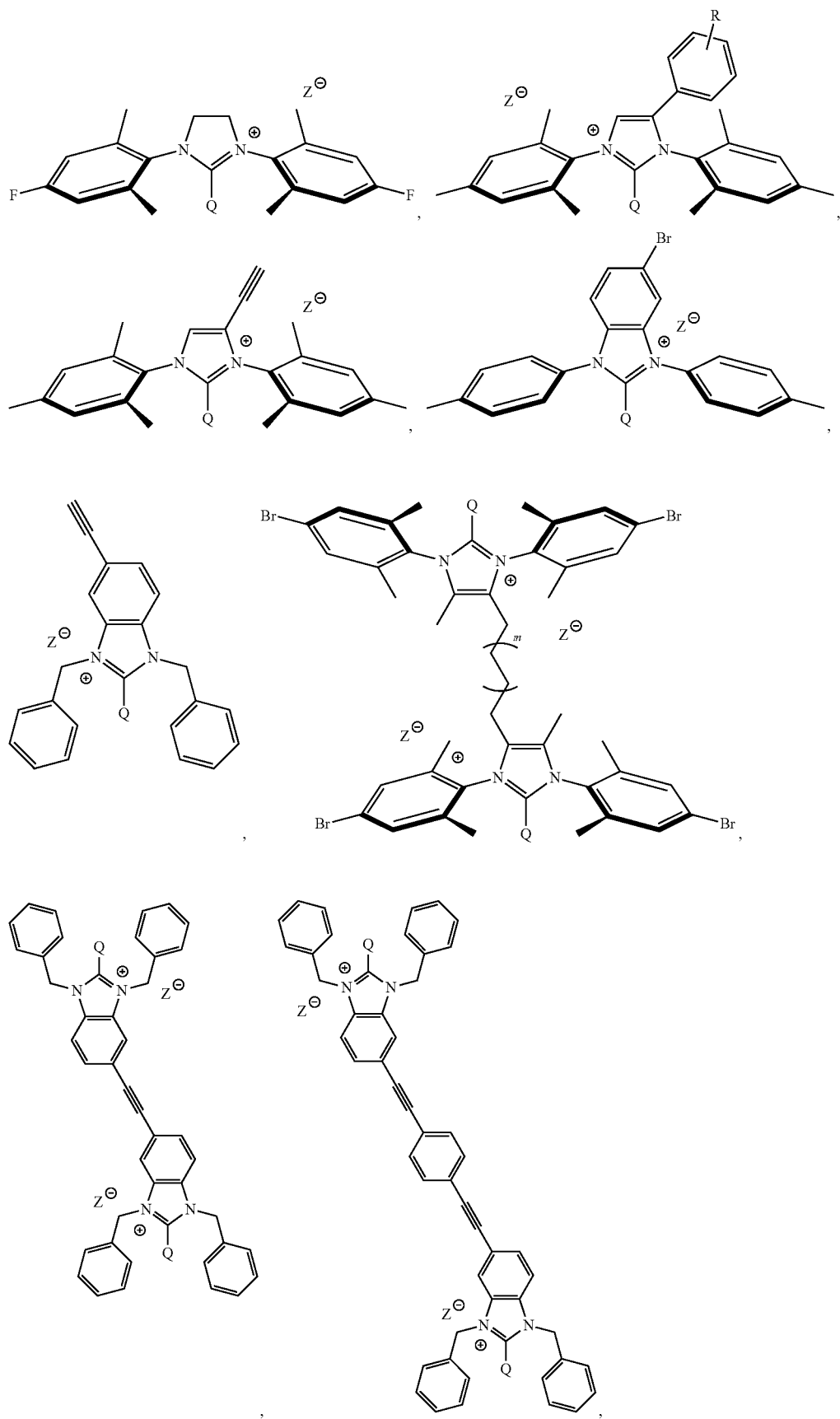

-continued

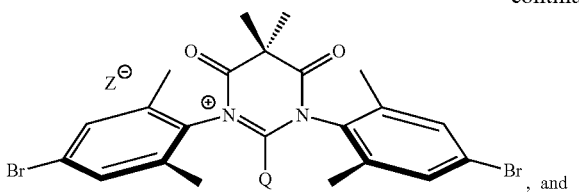, and 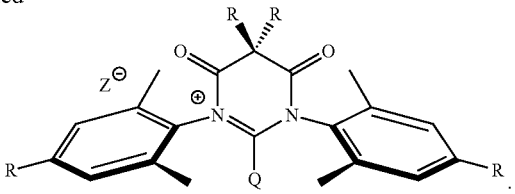.

wherein m is 0, 1, or 2 and $Z^-$ is as described herein.

In some embodiments, for a compound of Formula (III), Q is $CO_2$. In certain embodiments, Q is a halide (e.g., Cl).

In some embodiments, the persistent carbene precursor is acyclic. Non-limiting examples of acyclic persistent carbenes precursors include the following:

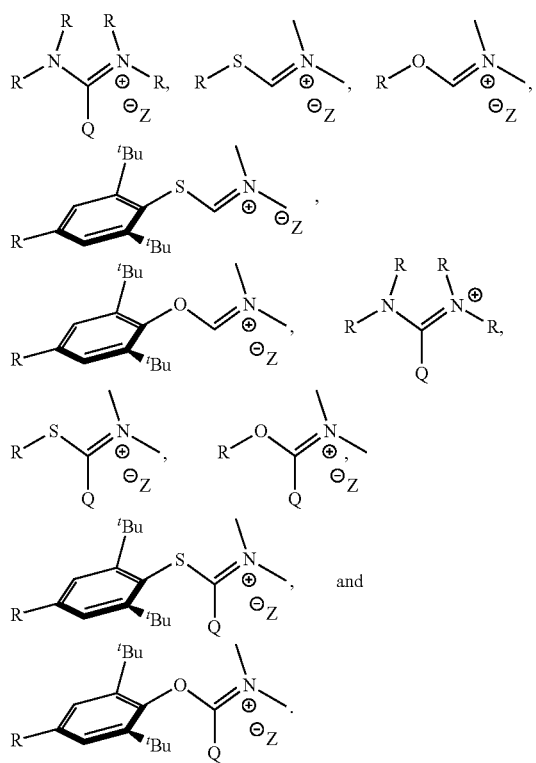

In some embodiments, at least one R comprises a functionalizable group. Examples of suitable R groups, Q groups, and functionalizable groups are described herein in connection with a compound of Formula (I).

In some embodiments, an article comprising a persistent carbene associated with a substrate has the structure:

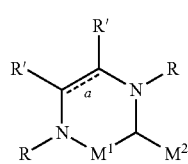

wherein each R is independently hydrogen, optionally substituted alkyl, optionally substituted alkylene, alcohol, halo, optionally substituted heteroalkyl, optionally substituted heteroalkylene, optionally substituted cycloheteroalkyl, optionally substituted cycloheteroalkylene, optionally substituted alkenyl, optionally substituted alkenylene, optionally substituted alkynyl, optionally substituted alkynylene, optionally substituted aryl, optionally substituted arylene, optionally substituted heteroaryl, optionally substituted heteroarylene, optionally substituted alkenyloxy, optionally substituted alkenyleneoxy, optionally substituted alkoxy, optionally substituted alkyleneoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile;

when present, each R' is independently hydrogen, optionally substituted alkyl, optionally substituted alkylene, alcohol, halo, optionally substituted heteroalkyl, optionally substituted heteroalkylene, optionally substituted cycloheteroalkyl, optionally substituted cycloheteroalkylene, optionally substituted alkenyl, optionally substituted alkenylene, optionally substituted alkynyl, optionally substituted alkynylene, optionally substituted aryl, optionally substituted arylene, optionally substituted heteroaryl, optionally substituted heteroarylene, optionally substituted alkenyloxy, optionally substituted alkenyleneoxy, optionally substituted alkoxy, optionally substituted alkyleneoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile;

optionally, any two R may be joined to form a ring;

optionally, any R may be substituted with a group forming a bond to a second persistent carbene;

$\underline{\overline{a}}$ is a single or double bond, provided when $\underline{\overline{a}}$ is a double bond each R' is absent; and $M^1$ and $M^2$ are independently a metal or metalloid comprised in the substrate.

In some embodiments, at least one R comprises a functionalizable group. In some embodiments, $M^1$ and/or $M^2$ may be a metalloid (e.g., Si), wherein the substrate comprises the metalloid. In some instances, $M^1$ and/or $M^2$ may be a metal, wherein the substrate comprises the metal. For example, in some embodiments, $M^1$ and/or $M^2$ are silicon.

In some embodiments, a method comprises associating a persistent carbene with a substrate to form a first structure (or providing the first structure):

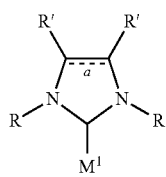

and exposing the first structure to reaction conditions (e.g., heat) to form a second structure:

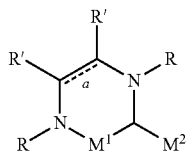

wherein each R is independently hydrogen, optionally substituted alkyl, optionally substituted alkylene, alcohol, halo, optionally substituted heteroalkyl, optionally substituted heteroalkylene, optionally substituted cycloheteroalkyl, optionally substituted cycloheteroalkylene, optionally substituted alkenyl, optionally substituted alkenylene, optionally substituted alkynyl, optionally substituted alkynylene, optionally substituted aryl, optionally substituted arylene, optionally substituted heteroaryl, optionally substituted heteroarylene, optionally substituted alkenyloxy, optionally substituted alkenyleneoxy, optionally substituted alkoxy, optionally substituted alkyleneoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile;

when present, each R' is independently hydrogen, optionally substituted alkyl, optionally substituted alkylene, alcohol, halo, optionally substituted heteroalkyl, optionally substituted heteroalkylene, optionally substituted cycloheteroalkyl, optionally substituted cycloheteroalkylene, optionally substituted alkenyl, optionally substituted alkenylene, optionally substituted alkynyl, optionally substituted alkynylene, optionally substituted aryl, optionally substituted arylene, optionally substituted heteroaryl, optionally substituted heteroarylene, optionally substituted alkenyloxy, optionally substituted alkenyleneoxy, optionally substituted alkoxy, optionally substituted alkyleneoxy, optionally substituted thio, epoxy, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile; optionally, any two R may be joined to form a ring;

optionally, any R may be substituted with a group forming a bond to a second persistent carbene;

$\overline{\overline{a}}$ is a single or double bond, provided when $\overline{\overline{a}}$ is a double bond each R' is absent; and $M^1$ and $M^2$ are independently a metal or metalloid comprised in the substrate. In some embodiments, at least one R comprises a functionalizable group. In some embodiments, $M^1$ and/or $M^2$ may be a metalloid (e.g., Si), wherein the substrate comprises the metalloid. In some instances, $M^1$ and/or $M^2$ may be a metal, wherein the substrate comprises the metal. In some embodiments, the method is used to form an article, as described herein.

Those of ordinary skill in the art will be aware of methods for synthesizing the persistent carbenes and precursors thereof described herein. See, for example, the methods described in the examples sections and the literature (e.g., see, for example, (1) Hirano, K.; Urban, S.; Wang, C.; Glorius, F. Org. Lett. 2009, 11, 1019, (2) Kuhn, K. M.; Grubbs, R. H. Org. Lett. 2008, 10, 2075, and (3) Alcarazo, M.; Roseblade, S. J.; Alonso, E.; Fernández, R.; Alvarez, E.; Lahoz, F. J.; Lassaletta, J. M. J. Am. Chem. Soc. 2004, 126, 13242). In some embodiments, a persistent carbene may be synthesized by conversion of a persistent carbene precursor, for example, by exposing a persistent carbene precursor to a base.

It should be understood that though certain resonance structures have been provided for persistent carbenes and persistent carbene precursors, the present invention is not limited to particular resonance structures. Those of ordinary skill in the art would know other possible resonance structures for the persistent carbenes and persistent carbene precursors, described herein.

For convenience, certain terms employed in the specification, examples, and appended claims are listed here.

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched, and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched, or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6, or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclohexyl.

The term "alkylene" as used herein refers to a bivalent alkyl group. An "alkylene" group is a polymethylene group, i.e., —$(CH_2)_z$—, wherein z is a positive integer, e.g., from 1 to 20, from 1 to 10, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described herein for a substituted aliphatic group.

Generally, the suffix "-ene" is used to describe a bivalent group. Thus, any of the terms defined herein can be modified with the suffix "-ene" to describe a bivalent version of that moiety. For example, a bivalent carbocycle is "carbocyclylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", a bivalent heteroalkyl chain is "heteroalkylene", a bivalent heteroalkenyl chain is "heteroalkenylene", a bivalent heteroalkynyl chain is "heteroalkynylene", and so forth.

The terms "alkenyl" and "alkynyl" are given their ordinary meaning in the art and refer to unsaturated aliphatic groups analogous in length and possible substitution to the alkyls described above, but that contain at least one double or triple bond respectively.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "cycloalkyl," as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or hetercyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched, or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl" is given its ordinary meaning in the art and refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, alkoxyalkyl, amino, thioester, poly(ethylene glycol), and alkyl-substituted amino.

The terms "heteroalkenyl" and "heteroalkynyl" are given their ordinary meaning in the art and refer to unsaturated aliphatic groups analogous in length and possible substitution to the heteroalkyls described above, but that contain at least one double or triple bond respectively.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CHF$_2$; —CH$_2$F; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls, and/or heterocyclyls. The aryl group may be optionally substituted, as described herein. Substituents include, but are not limited to, any of the previously mentioned substituents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substituents, i.e., the substitutes recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl)heteroaryl moieties. Thus, as used herein, the phrases "aryl or heteroaryl moieties" and "aryl, heteroaryl, -(alkyl)aryl, -(heteroalkyl)aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The term "heterocycle" is given its ordinary meaning in the art and refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms.

The term "heterocycle" may include heteroaryl groups, saturated heterocycles (e.g., cycloheteroalkyl) groups, or combinations thereof. The heterocycle may be a saturated molecule, or may comprise one or more double bonds. In some cases, the heterocycle is a nitrogen heterocycle, wherein at least one ring comprises at least one nitrogen ring atom. The heterocycles may be fused to other rings to form a polycylic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "halo" and "halogen" as used herein refer to an atom selected from the group consisting of fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino," as used herein, refers to a primary (—NH$_2$), secondary (—NHR$_x$), tertiary (—NR$_x$R$_y$), or quaternary (—N$^+$R$_x$R$_y$R$_z$) amine, where R$_x$, R$_y$, and R$_z$ are independently an aliphatic, alicyclic, heteroaliphatic, heterocyclic, aryl, or heteroaryl moiety, as defined herein. Examples of amino groups include, but are not limited to, methylamino, dimethylamino, ethylamino, diethylamino, methylethylamino, iso-propylamino, piperidino, trimethylamino, and propylamino.

The term "alkyne" is given its ordinary meaning in the art and refers to branched or unbranched unsaturated hydrocarbon groups containing at least one triple bond. Non-limiting examples of alkynes include acetylene, propyne, 1-butyne, 2-butyne, and the like. The alkyne group may be substituted and/or have one or more hydrogen atoms replaced with a functional group, such as a hydroxyl, halogen, alkoxy, and/or aryl group.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, t-butoxy, neopentoxy, and n-hexoxy. Examples of thioalkyl include, but are not limited to, methylthio, ethylthio, propylthio, isopropylthio, n-butylthio, and the like.

The term "aryloxy" refers to the group, —O-aryl.

The term "acyloxy" refers to the group, —O-acyl.

The term "alkoxyalkyl" refers to an alkyl group substituted with at least one alkoxy group (e.g., one, two, three, or more, alkoxy groups). For example, an alkoxyalkyl group may be —(C$_{1-6}$-alkyl)-O—(C$_{1-6}$-alkyl), optionally substituted. In some cases, the alkoxyalkyl group may be optionally substituted with another alkyoxyalkyl group (e.g., —(C$_{1-6}$-alkyl)-O—(C$_{1-6}$-alkyl)-O—(C$_{1-6}$-alkyl), optionally substituted.

As used herein, the term "phosphine" is given its ordinary meaning in the art and refers to a group comprising at least one phosphorus atom. The phosphorus atom may bear one, two, or three aliphatic or aromatic groups, optionally substituted and optionally comprising at least one heteroatom.

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether proceeded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful for the formation of an imaging agent or an imaging agent precursor. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

The following examples are intended to illustrate certain embodiments of the present invention, but do not exemplify the full scope of the invention.

EXAMPLES

Example 1

Abstract:

New strategies to access functional monolayers can augment current surface modification methods. Here, addressable N-heterocyclic carbene (ANHC) anchors for gold surfaces are presented. Several experimental and theoretical methods were used to characterize ANHC monolayers. Grafting of highly fluorinated polymers from surface-bound ANHCs was demonstrated. This Example illustrates ANHCs as viable anchors for gold surfaces.

Introduction:

Since its discovery in 1983, the chemisorption of thiols on gold surfaces has enabled countless technological advances in the fields of electronics, sensing, microfabrication, and nanotechnology. Despite the broad utility, thiol monolayer formation has limitations. For example, the relatively weak S—Au bond (~45 kcal/mol) can lead to monolayer desorption at moderate temperatures (~100-150° C.). Furthermore, S—Au based monolayers often have ill-defined binding geometries; their precise structure is still a topic of debate. Finally, S—Au bonds are typically have low conductive, which could limit their use in molecular electronics applications.

Other anchor groups (e.g., thioether, selenol, amine, pyridine, dithio-ate/-carbamate/-phosphinate, isocyanide, alkynyl, aryl, phosphine, and alkyl groups) have also been explored for binding to gold surfaces. Though some of these moieties display promising features such as increased conductivity or improved binding strength, there is still a need for a general, synthetically versatile complement to Au—S monolayer formation.

N-heterocyclic carbenes (NHCs) were hypothesized to be a potentially useful class of reagents for binding to inorganic (e.g., gold) surfaces (FIG. 2). NHCs offer a combination of exceptional σ-donating and moderate π-backbonding ability, which has made them ligands of choice for late transition metals like Ru(II) and Au(I). It was envisioned that these same characteristics could lead to strong, partially conjugated, NHC—Au surface bonds. Furthermore, the synthetic flexibility of NHCs could facilitate their general use for surface modification.

Figure 3A:
FIG. 3A-FIG. 3E show the functionalization of persistent carbenes and secondary compounds, which are associated with a substrate, according to certain embodiments.
Figure 3B:
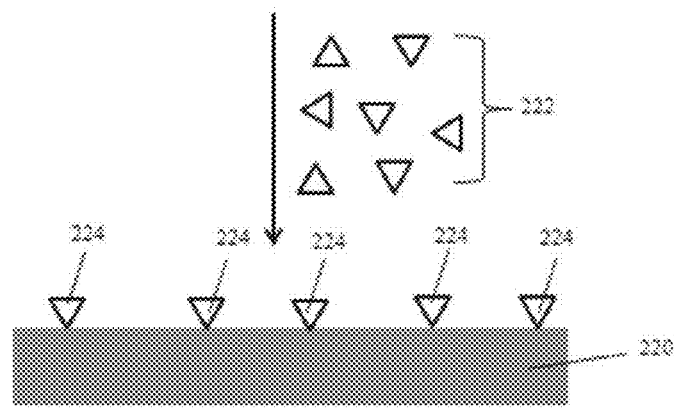
Figure 3C:
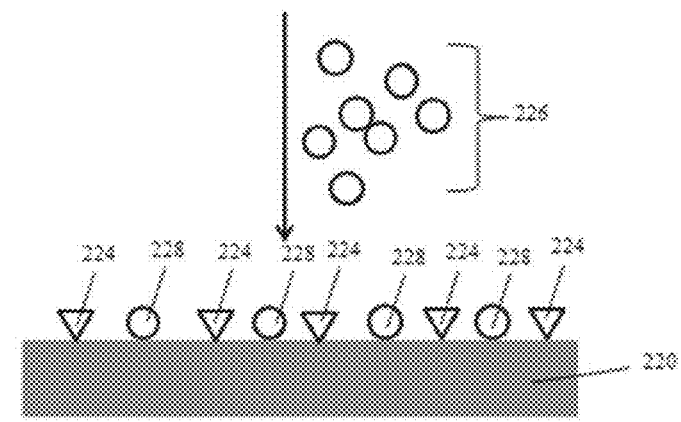
Figure 3D:
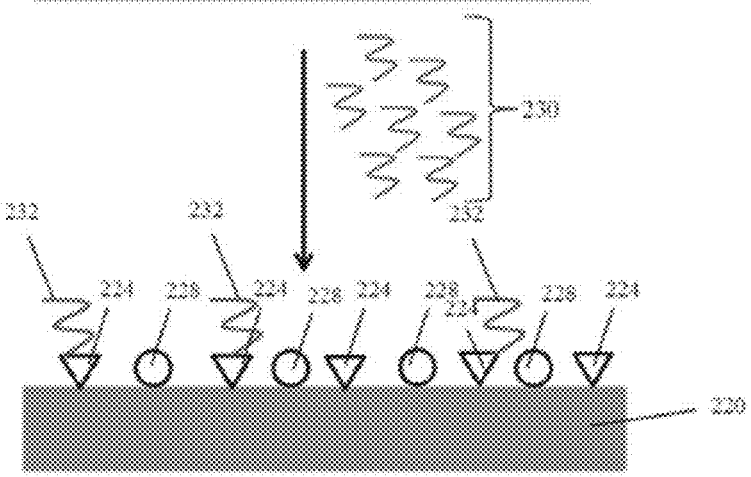
Figure 3E:
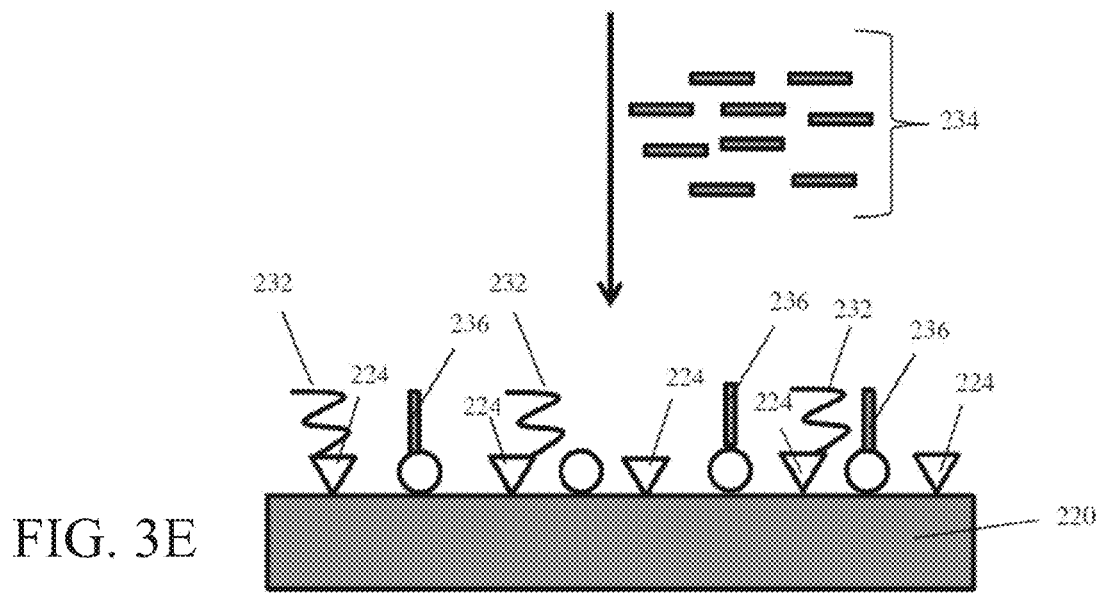

Results and Discussion:

In order to study NHC-gold surface binding and NHC monolayer functionalization, two addressable NHCs (ANHCs) that possess aryl-bromide (1) and β-methylstyrene (2) functionalizable groups were synthesized as shown in FIG. 3A and FIG. 3B. The bond characteristics and surface interactions of 1 and 2 with gold (Au) were then characterized using crystallography, quartz crystal microbalance dissipation (QCM-D), X-ray photoelectron spectroscopy, and simulations.

Synthesis:

The imidazolium salt precursor to ANHC 1 (IS1) was synthesized in multi-gram scale via a modified two-step procedure as shown in Scheme 1 in Example 2. The precursor to ANHC 2 (IS2) was prepared from IS1 by a modified Stille cross-coupling with allyltributyltin as shown in Scheme 1. The unexpected formation of the bis-β-methylstyrene derivative, rather than the bis-allyl, likely arose from [NHC—Pd—H]$^+$-catalyzed allyl isomerization.

Scheme 1. Synthesis of novel imidazolium salts IS1 and IS2.

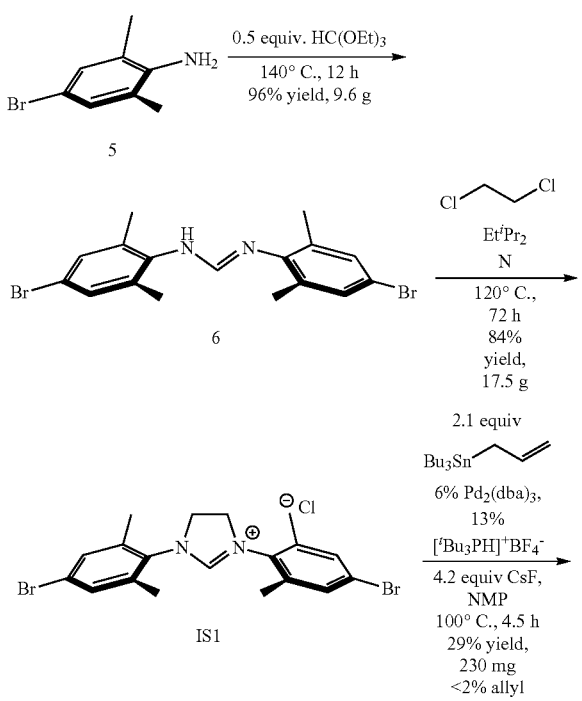

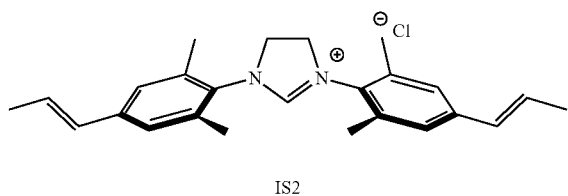

IS2

Bond Characterization:

Both ANHCs 1 and 2 formed Au(I) complexes (e.g., 3, FIG. 7B) upon exposure to potassium hexamethyldisilazide (KHMDS) and (Ph3P)AuCl in tetrahydrofuran (THF) as shown in Scheme 2. Careful control of the reaction conditions enabled access to both mono- and bis-NHC complexes (Scheme 2). The crystal structure of 3 featured a C—Au bond length of 1.98 Å, which was consistent with reported values for IMes- and SIMes-Au(I) complexes (2.00 and 1.98 Å, respectively). Of note, the C—Au bond length was much shorter than the Au—S bond length (2.2-2.6 Å) observed in crystal structures of thiolate-stabilized gold nanoparticles.

Scheme 2.
Synthesis of NHC—Au(I) complexes 3, 7, and 8.

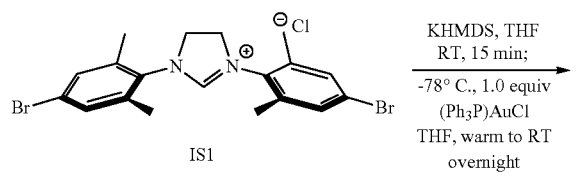

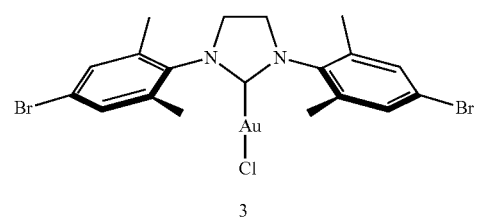

3

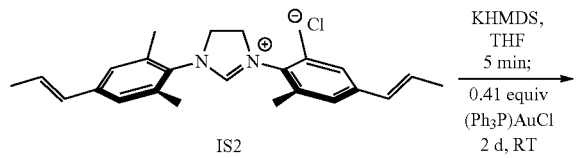

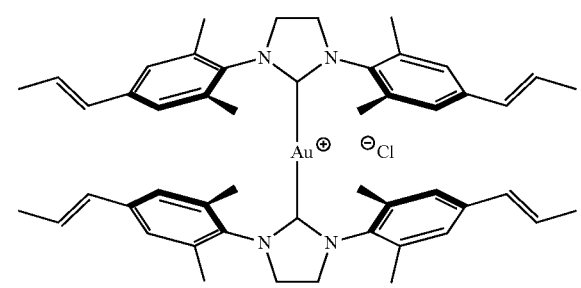

7

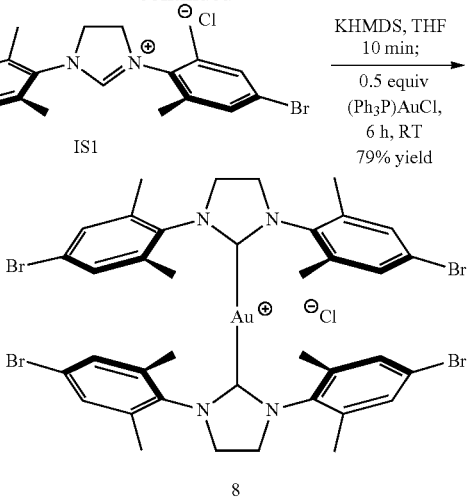

8

In order to gain insight into the nature of the NHC—Au surface binding, density functional theory (DFT) was used to model the binding of 1 to a charge neutral gold adatom above a fixed gold lattice. The calculated structure (FIG. 8A) possessed a C—Au bond length of 2.03 Å, which agreed with the C—Au bond length in the crystal structure for 3. Furthermore, the calculated homolytic Au—C bond dissociation energy (BDE) was found to be 67 kcal/mol, which was more than 20 kcal/mol larger than a typical Au—S bond. Calculations performed using either a single gold atom or larger gold clusters produced similar 1-Au sigma-bonding orbitals, which suggests that the bonding of 1 is highly localized.

Next electronic coupling between 1 and a single neutral gold atom via DFT using the B3LYP functional was studied; the basis set was LANL2DZ+effective core potential for gold, and 6-31 g* for all other atoms. The relevant orbitals (HOMO-1, HOMO, LUMO) are depicted in FIG. 4B-FIG. 4D. The electron density in the HOMO-1 was delocalized over the gold atom and the carbene carbon; this delocalization extended to the nitrogen atoms in the HOMO. These results suggested that ANHCs could form conductive surface linkages. The energy of the HOMO was calculated to be −3.46 eV, which was more than 1.6 eV higher than the Fermi level of Au (i.e., −5.1 eV). In the LUMO, the electron density was primarily delocalized over the imidazolidin-2-ylidene fragment and the aryl substituents.

Surface Interactions:

Quartz crystal microbalance with dissipation (QCM-D) was used to study binding of 1 and commercially available IMes to gold surfaces. For all QCM-D experiments, a THF solution of free carbene was flown over a gold-coated sensor; binding was characterized via changes in frequency (F) and dissipation (D) of the sensor. The carbene solutions were prepared as follows:

(a) For 1 and 2: A THF suspension of imidazolium chloride ANHC precursor (IS1 or IS2, Scheme 1) was exposed to potassium hexamethyldisilazide (KHMDS, 1.0 equiv) under $N_2$. The resulting solution was filtered through a 0.25 μm syringe filter.

(b) For IMes: IMes was dissolved in THF under $N_2$. The solution was filtered through a 0.25 μm filter.

Both carbene solutions showed a rapid frequency change upon introduction to the QCM-D sensor; saturation was approached within 15 min. As expected for rigid monolayers, the surfaces were characterized by small ratios of ΔD:ΔF (<<4 e-7 Hz-1). The areal mass density (AMD) of bound species was estimated using the Sauerbrey method. Average AMD values for 1 and IMes taken from three measurements were 210±80 ng/cm² and 56±6 ng/cm², respectively.

Control experiments with HMDS amine or amide in the absence of carbene showed little binding of the former, but significant binding of the latter. Thus, it was hypothesized that binding of residual HMDS amide led to the larger AMD, and increased deviation, for 1 compared to IMes.

To test this hypothesis, a solution of pure 1 in THF was prepared via thermal decarboxylation of an independently synthesized $CO_2$-1 adduct shown in Scheme 3.

Scheme 3. Synthesis of $CO_2$-1 adduct

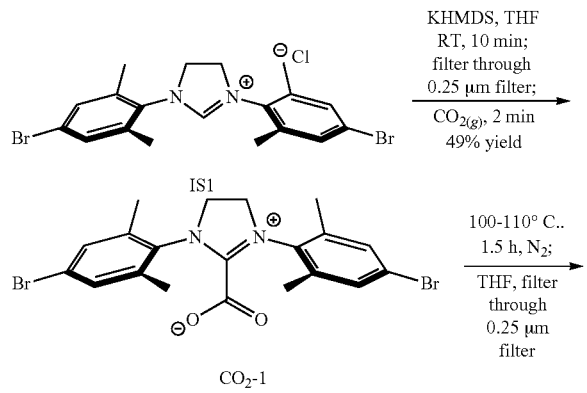

The average AMD value for this solution of 1 without HMDS was 63±14, which agrees well with the value for IMes.

For ANHC 1, a 7±2 Hz frequency change was observed during the first 3 min of NHC exposure, which was followed by a slow decrease in frequency. Saturation was approached within 15 min. As expected for rigid monolayers, these surfaces were characterized by small ratios of Δdissipation: Δfrequency ($\Delta D:\Delta f << 4\times 10^{-7}$ Hz$^{-1}$).

The areal mass density (AMD) of NHC was estimated using the Sauerbrey equation. The AMD values for 1 and IMes treated surfaces were 210±80 ng/cm² and 50 ng/cm², respectively. This disparity suggested that either the more nucleophilic carbene 1 binds more efficiently to the gold surface, or residual HMDS, which is absent in the pure IMes solution, binds along with 1 to form a mixed amine/NHC monolayer. Control experiments wherein gold surfaces were treated with HMDS or KHMDS showed minimal binding of the former, but significant binding of the latter.

Since it was assumed that 1 and IMes had equivalent surface affinities and that 1 was not blocked or displaced from the surface by HMDS, the AMD for 1 was estimated to be ~70 ng/cm². From the dimensions of 1 obtained via crystallography (FIG. 7B), an upper limit of 85 ng/cm² was calculated for a monolayer of 1 on a perfectly flat surface. This limit would be significantly higher for a real surface with non-zero roughness. Given the steric bulk of 1 and IMes these measured AMDs (~63 and ~56 ng/cm², respectively) were quite reasonable.

Monolayers of 1 and IMes prepared via immersion of gold-coated silicon wafers in solutions (a) or (b), respectively, were characterized by narrow-scan X-ray photoelectron spectroscopy (XPS). XPS spectra were normalized to the transmission-corrected area of the carbon peaks (FIG. 7C). As expected, the surface exposed to 1 showed a significant Br signal (FIG. 7D). The measured Br/N ratio was 0.16:1 (as shown in Table 1) corresponds to a mixed monolayer with 21% 1 and 79% HMDS by mass and agreed well with the ratio calculated from AMD values (~0.27:1). Furthermore, surfaces treated with IMes showed no detectable Br. These XPS spectra, along with the QCM-D data, collectively demonstrated the formation of relatively dense layers of 1 and IMes on gold surfaces.

TABLE 1

XPS analysis of NHC binding and brush polymer growth.

| Sample | C1s normalized peak area[a] (e−3) | N1s normalized peak area[a] (e−3) | Br3p normalized peak area[a] (e−3) | F1s normalized peak area[a] (e−3) | Br/F:N ratio |
|---|---|---|---|---|---|
| 1 | 27.4 | 1.04 | 0.17 | | 0.16 (Br) |
| IMes | 27.4 | 1.15 | | | |
| Brush-polymer (QCM-D)[b] | 27.4 | 1.75 | | 4.05 | 2.32 (F) |
| Polymerization control (no Ru, QCM-D) | 27.4 | 2.65 | | 0.61 | 0.23 (F) |
| Polymerization control (1 instead of 2, QCM-D) | 27.4 | 0.94 | Not detected | 1.94 | 2.06 (F) |

[a]Area was normalized by the raw area of the C1s peak and also by the elements' corresponding RSF values.
[b]Ru 3p3 region was analyzed by XPS as described in Example 2(linear baseline from 465.885 to 458.92 eV; corrected RSF = 185.820), revealing a normalized peak area of 0.0455e−3. DP = [Area(F)/5]Area(Ru) = 18.

Functionalization:

Chemical modification of an ANHC on a gold surface was demonstrated. The olefinic groups of ANHC 2 (FIG. 7A) were modified. In particular, it was envisioned that treatment of 2-Au surfaces with 3$^{rd}$ generation Grubbs catalyst (Ru, Scheme 5) would generate surface-bound ruthenium benzylidenes that could initiate the polymerization of a strained norbornene derivative via ring-opening metathesis polymerization (ROMP).

A series of model experiments using an isolated bis-2-Au (7) complex demonstrated that the initial cross metathesis step was efficient in solution as shown in Scheme 4.

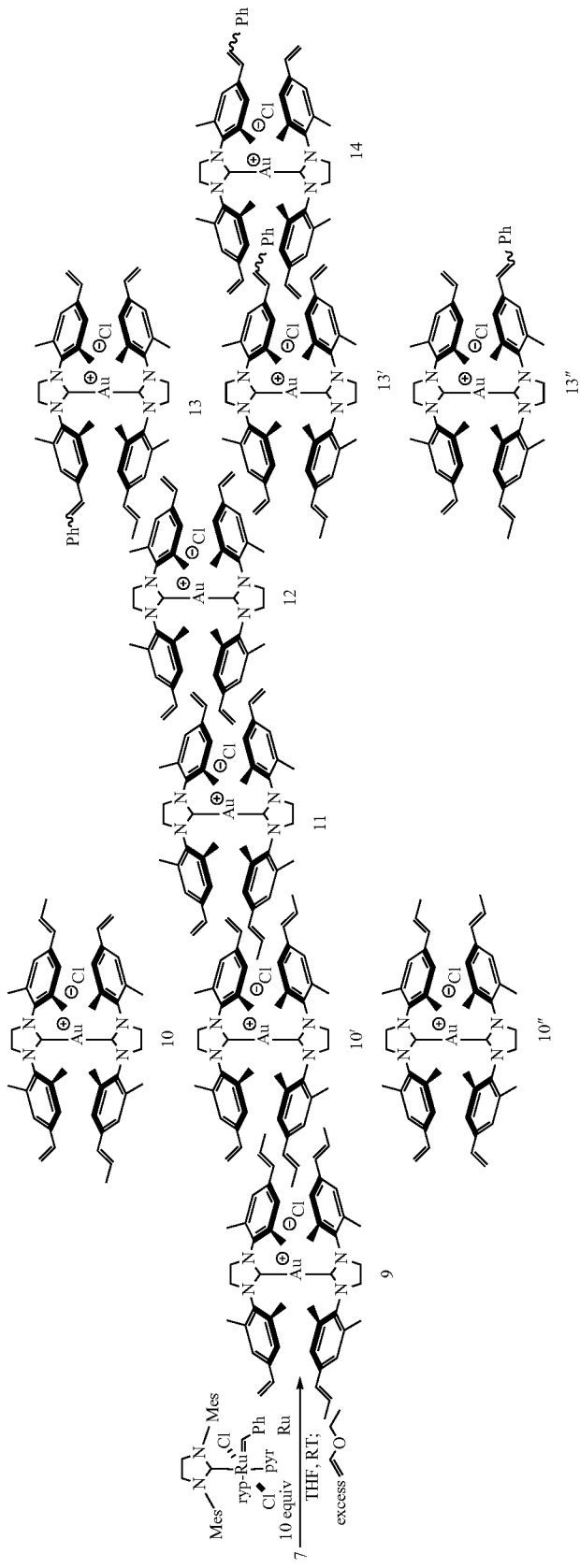
Scheme 4: Formation of Ru alkylidenes from bis-NHC complex 7 and 3rd generation Grubbs catalyst Ru.

Figures 9A, 9B, 9C:
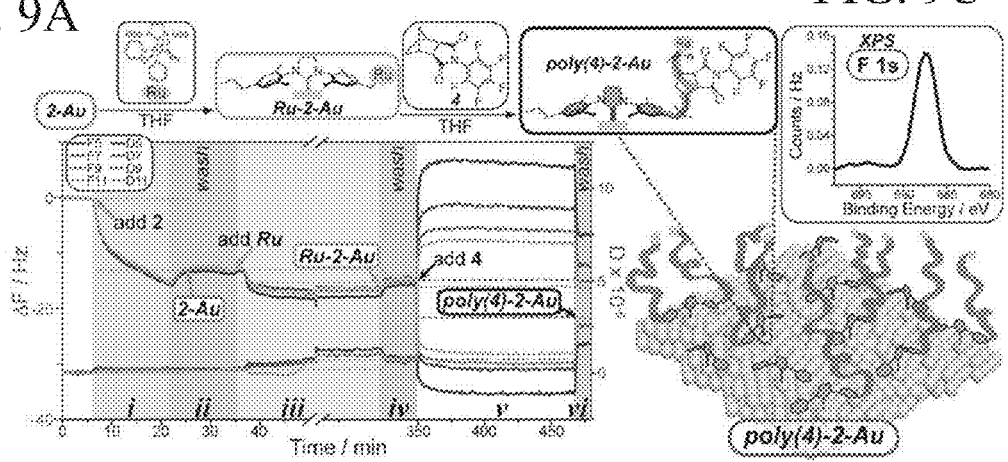
FIG. 9A shows a diagram of polymerization reaction starting from a persistent carbene bound to a gold substrate overlaid with quartz crystal microbalance-dissipation data for the functionalization process, according to certain embodiments.
FIG. 9B shows a schematic of the functionalized surface in connection with Figure A, according to certain embodiments.
FIG. 9C shows the F 1s region of the X-ray photoelectron spectrum of functionalized surface in connection with FIG. 9A, according to certain embodiments.

Encouraged by these results, the sequence of reactions depicted in FIG. 9A was performed in flow over a gold-coated QCM-D sensor. The entire process was monitored by QCM-D; relevant steps are labeled i-vi in FIG. 9A. First, exposure of a gold surface of the sensor to a 0.21 mM solution of 2 (prepared via method (a)) in THF for 15 min at 23.6° C. (region i) resulted in a 2+HMDS AMD of ~230 ng/cm². The surface was washed with THF followed by a wash with fresh THF (region ii and resulted in an AMD of 230 ng/cm². If it is assumed that 2 binds to the surface with equal affinity to IMes and 1, then ~61 ng/cm² of this AMD value corresponds to 2). The surface was then exposed to a 5.80 mM solution of Ru in THF for 5 h (region iii). Another THF wash was then performed (region iv). At this stage, the surface consisted of putative Ru-benzylidene complexes bound via the 2-Au linkage (FIG. 9A, Ru-2-Au surface). The 2-Au to Ru-2-Au process coincided with a ~2.6 Hz frequency change, and a significant change in dissipation (from ~0.2 e-6 to ~0.7 e-6). Because ΔD:Δf was relatively large, the Voigt model, which takes dissipation into account, was used to calculate a AMD of 60 ng/cm² (see SI for details of the calculation). If we assume 61 ng/cm² adsorption of 2 (based on IMes binding), then ~39% of olefins from 2 were converted to ruthenium benzylidenes. This result was consistent with the model study using complex 5.

Figures 8A, 8B, 8C, 8D:
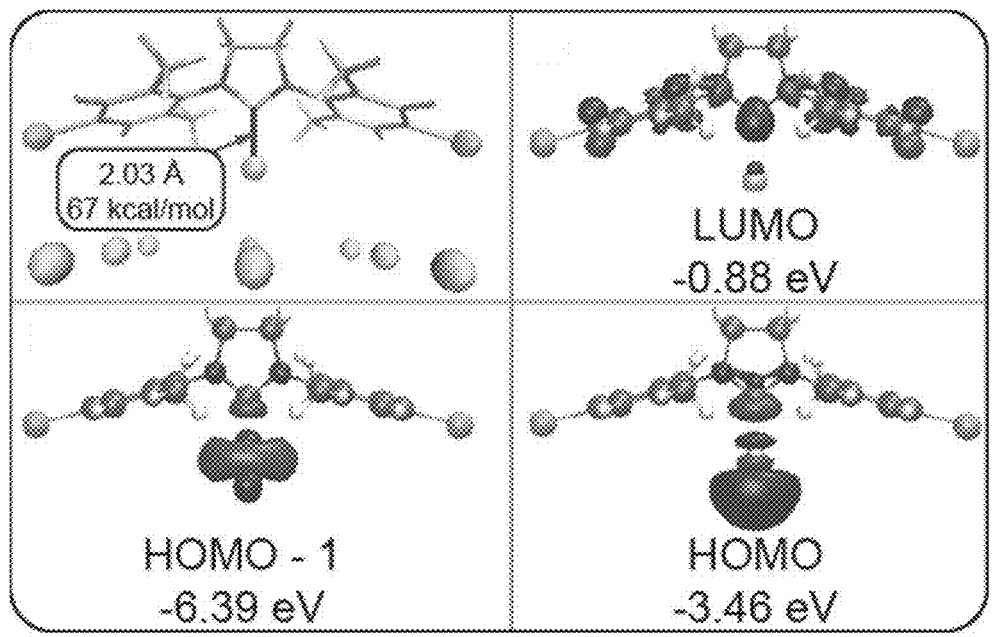
FIG. 8A shows a density functional theory model of a persistent carbene bound to a gold surface, according to certain embodiments.
FIG. 8B-FIG. 8D show frontier orbitals, HOMO-1, and orbital energies of the persistent carbene-Au(0) complex in connection with FIG. 8A, respectively, according to certain embodiments.

Subsequent exposure of the surface to pentafluorophenyl exo-norbornene derivative 4 (Scheme 5; 0.121 M in THF) for 2 hours (region v) resulted in drastically altered frequency and dissipation values along with an observed dispersion in 1/n Δf for different values of n (FIG. 8A). These results were consistent with growth of flexible polymer chains from the surface to generate a surface brush (poly (4)-2-Au, FIG. 8A and FIG. 8B). The AMD from polymerization was 1520 ng/cm², which, if polymer solvation is neglected, translated to an average degree of polymerization (DP) of 35.

No polymerization was observed when the same sequence of events was carried out using 1 rather than 2, which confirms the role of the olefinic groups of 2. Finally, exposure of a 2-Au surface to monomer 4 in the absence of catalyst Ru gave no change in dissipation and a small AMD of ~53 ng/cm² due to non-specific adsorption; no polymerization occurred.

XPS analysis was performed on the same surfaces used for QCM-D experiments (FIG. 8C). As expected, the poly (4)-2-Au surface exhibited high fluorine content (FIG. 9C). Both control samples showed much lower fluorine signal from adsorbed 4. The Ru/F ratio for poly(4)-2-Au suggested an average brush DP of 18 (e.g., assuming 1 Ru per polymer chain and 5 F atoms per polymer repeat unit) as shown in Table 1. The difference in DP compared to QCM-D was likely due to polymer solvation.

Figure 10A:
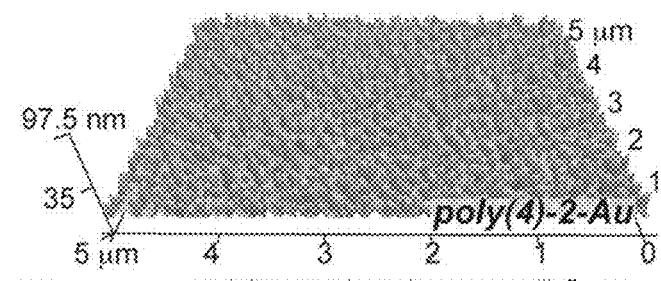
FIG. 10A shows atomic force microscopy characterization of a functionalized surface, according to one set of embodiments.
Figure 10B:
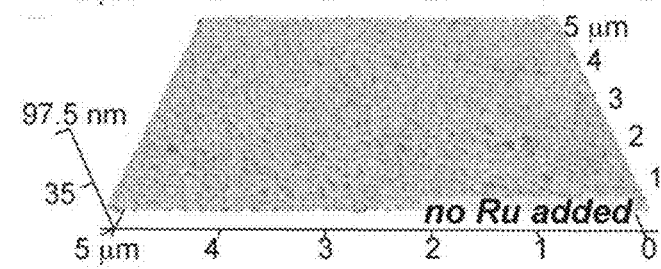
FIG. 10B shows atomic force microscopy characterization of a control surface, according to one set of embodiments.

Tapping mode atomic force microscopy (AFM) analysis of these surfaces revealed a marked difference in roughness. Poly(4)-2-Au had a roughness of 5.6 nm (FIG. 9A). In contrast, the control sensors had RMS surface roughness values of 1.4 nm (no Ru, FIG. 9B) and 2.0 nm (1 instead of 2), which matched that reported values for the bare sensors (≤3 nm). Moreover, the elongated cone-like features present only in the AFM image of poly(4)-2-Au (FIG. 10A) resembled those reported for other poly-norbornene grafted surfaces.

Conclusion:

In this Example, gold surface functionalization with addressable NHCs (ANHCs) was described. We expect that these results will spark interest in the use of ANHCs and other stable carbenes as general surface anchors.

Example 2

This example describes the experimental materials and methods used in Example 1.

All reagents and solvents were purchased from Sigma-Aldrich® or VWR and used as supplied unless otherwise noted. Ruthenium catalyst Ru as shown in Scheme 5 and N-(pentafluorophenyl)-cis-5-norbornene-exo-dicarboximide² (4, as shown in Scheme 5) were prepared according to literature procedures. Degassed tetrahydrofuran (THF) was passed through a solvent purification column prior to use in air-sensitive experiments.

Scheme 5. Structures of ruthenium catalyst Ru and N-(pentafluorophenyl)-cis-5-norbornene-exo-dicarboximide 4.

Ru =

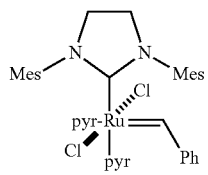

4 =

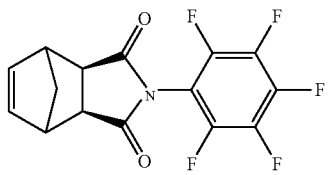

Liquid chromatography-mass spectrometry (LC/MS) and preparative HPLC were performed on an Agilent 1260 LC system equipped with a Zorbax SB-C18 rapid resolution HT column and an Advanced Materials Technology HALO® C18 high performance column. Solvent gradients consisted of mixtures of nano-pure water with 0.1% acetic acid (AcOH) and HPLC-grade acetonitrile. Mass spectra were obtained using an Agilent 6130 single quadrupole mass spectrometer.

$^1$H nuclear magnetic resonance ($^1$H-NMR) and $^{13}$C nuclear magnetic resonance ($^{13}$C-NMR) spectra were recorded on two Bruker AVANCE-400 NMR spectrometers. Chemical shifts are expressed in parts per million (ppm), and splitting patterns are designated as s (singlet), d (doublet), t (triplet), q (quartet), m (multiplet), and br (broad); AB designates a system of protons whose coupling constant is comparable to their chemical shift difference. Coupling constants J are reported in Hertz (Hz). MestReNova LITE v5.2.5-4119 software (Mestrelab Research S.L.) was used to analyze the NMR spectra. Spectra were referenced to solvent peaks as reported in literature.

High-resolution mass spectrometry (HRMS) was obtained using a Bruker Daltonics APEXIV 4.7 Tesla Fourier Transform Ion Cyclotron Resonance Mass Spectrometer (FT-ICR-MS).

X-ray photoelectron spectroscopy (XPS) was carried out at the MIT Center for Materials Science and Engineering on a Physical Electronics Versaprobe II X-ray Photoelectron Spectrometer. For non-conductive samples (e.g. quartz crystals), argon ion charge neutralization was employed. The step size used in all narrow-scan experiments was 0.50 eV, and a pass energy of 117.4 was chosen. XPS data processing was carried out using CasaXPS software written by Neal Fairley. All spectra were calibrated by setting the carbon peak at 285.0 eV. All narrow-scan spectra were smoothed using the 5-point quadratic Savitzky-Golay algorithm[5] and baseline-corrected using a linear baseline shape. The spectra were then normalized by the area of the corresponding carbon peak and by the elements' corrected relative sensitivity factors specific to the XPS instrument for the chosen pass energy (C1s=36.557; N1s=58.185; Br3p=186.857; F1s=116.964). The following boundaries were used for baseline correction: C1s: 298-278 eV; N1s: 410.906-392.997 eV; Br3p: 195-178 eV; F1s: 698-680 eV. The calculated areas were automatically corrected for instrumental influences in CasaXPS by dividing by the product of the transmission coefficient and the mean free path (116.4 in all collected spectra).

Quartz crystal microbalance with dissipation monitoring (QCM-D) gravimetry was performed in a four-hand Atmos-Bag polyethylene glovebag purchased from Sigma-Aldrich® using the Q-Sense E1 instrument, Q-Sense flow module 401, and optically polished (RMS roughness ≤3 nm) gold-coated AT-cut quartz crystal sensors with the fundamental frequency of 4.95 MHz (Q-Sense, Gothenburg, Sweden); the corresponding constant $C=17.5$ $ng/(Hz\ cm^2)$ (rounded to the nearest 0.5). Liquid was drawn through the system using a peristaltic pump (REGLO Digital/Ismatec® SA, IDEX Health & Science, Glattbrugg, Switzerland). Highly chemical-resistant Kalrez® sealing gasket and O-ring were used in all experiments, and non-teflon tubing was replaced with GORE® Style 100CR highly resistant pump tubing together with a Perifit-PEEK fitting for this tubing. An actual temperature of 23.6° C. (set temperature of 23.7° C.) and true flow rate of 0.332 mL/min (nominal pump rate of 0.0144 mL/min) were used in all experiments; flow was paused only to switch solutions and to allow for 2-5 h exposure of sensors to solution of monomer 6 or catalyst 4. At the start of each measurement, stable baselines for both F and D were achieved; at the end of each measurement, the system was rinsed with THF (40 mL) and methanol (40 mL) (with the exception of IMes, HMDS, and KHMDS which were not washed with methanol) at a nominal pump flow rate of ~0.62-0.66 mL/min (true rate ~14-15 mL/min). After rinsing with pure solvent, the sensors were dried under a flow of nitrogen gas and stored in ambient. Before each experiment, the sensors were cleaned by 10 min UV/ozone treatment, followed by immersion into a 5:1:1 mixture of nano-pure water, 25% $NH_4OH_{(aq)}$, and 30% $H_2O_{2\ (aq)}$ at 75° C. for 5 min and 10 min UV/ozone treatment. Frequency shift and dissipation were measured and recorded at multiple harmonics (fundamental frequency, 3rd, 5th, 7th, 9th, 11th, and 13th overtone) with the QSoft 401 software (Q-sense, Gothenburg, Sweden) in real-time throughout the adhesion process; the software automatically normalized each curve by the overtone number and plotted them as such. For non-dissipative samples, the areal mass density change was determined using the Sauerbrey model: $\Delta m=-C\cdot j^{-1}\cdot \Delta F$, where j is the overtone number, m is areal mass density, F is sensor frequency, and C is the constant defined above ($17.5\ ng/(Hz\cdot cm^2)$). Data analyses for cases where Sauerbrey model was not applicable were done with QTools (Q-sense, Gothenburg, Sweden) using Voigt viscoelastic modeling. The constraints applied in the modeling were as follows: only overtones 3, 5, 7, 9, and 11 were used in the analysis; the Voigt viscoelastic model was applied to the entire duration of the experiment, with the output being areal mass density for layer 1 (L1); fluid density=1016 $kg/m^3$, fluid viscosity=0.00046 kg/m·s, and L1 density=1000 $kg/m^3$; 0.0001<L1 viscosity (kg/m·s)<0.01, 0.0001<L1 shear (Pa)<1 e9, and 0.0001<L1 mass $(ng/cm^2)$<1 e5. The following calculation was used to determine the conversion of olefins to ruthenium alkylidenes in QCM-D experiments: % Conversion of olefins to Ru alkylidenes=100%*(nmol catalyst bound)/(2*nmol 2 bound to surface)=100%*[mass density of catalyst bound/(MW catalyst-MW methylstyrene-2*MW pyridine)]/[2*mass density of NHC bound/MW 2]=100%*[60 $ng/cm^2$/(726.74-118.177-2*79.1 g/mol)]/[2*59 ng/cm2/358.45 g/mol]=40%.

Atomic force microscopy (AFM) was carried out in tapping mode on an MFP-3D AFM instrument (Asylum Research, Santa Barbara, Calif.) using a silicon probe with a resonant frequency of 300 kHz (Fo) and a nominal spring constant of 40 N/m, designed for tapping mode (AppNano; MikroMasch). The following parameters were used in the measurements: scan rate: 0.75 Hz; resolution: 512 points/line, 512 lines/raster; scan angle: 0°; the measurements were carried out in ambient conditions. The data was analyzed using the Igor Pro 6.22AI MFP3D 101010-1403 combined software.

All density functional theory computations were done using the Q-Chem software package. The bond dissociation enthalpy (BDE) was calculated for a variety of NHC-gold complexes. In each case, a gas-phase geometry optimization was performed using the B3LYP exchange-correlation functional and the LANL2DZ basis set and effective core potential for gold and the 6-31 g* basis set for every other atom (implemented in Q-Chem as "LACVP"). Following the geometry optimization, three single-point energy calculations were performed at the relaxed geometry: One of the entire NHC-gold complex, one of just the NHC molecule, and one of just the gold atoms. The BDE was calculated as: $BDE=E_{complex}-(E_{NHC}+E_{AU})$.

For the model gold system presented in FIG. 8, all gold-gold bond distances were set to 4.08 Å, the lattice parameter for bulk gold, and all gold atoms were subsequently fixed in place for the duration of the calculation. The geometry optimization was then performed allowing the NHC molecule to relax in the field of the fixed gold atoms. Since not all atoms were allowed to relax in this simulation, several other calculations were performed on model gold systems to confirm the calculated BDE. A four-atom gold cluster was chosen as the primary model as it is the smallest cluster of gold atoms that can model binding to the each the atop, bridge, and hollow sites realized on a gold surface. According to the Blyholder model, the energetics of the binding of substrates to surfaces should quantitatively captured by studying the binding of substrates to small clusters.

The globally-optimized geometry of a four-atom gold cluster was obtained from the Cambridge Cluster Database. The geometry of the four gold atoms was allowed to relax; then, all gold atoms were fixed while the geometry of the NHC was allowed to relax. For this system, the NHC-gold bond length was determined to be 2.01 Å, and the BDE 66 kcal/mol. Next, the gold atom in contact with the NHC molecule was allowed to relax while the other three gold atoms remained fixed. For this system, the NHC-gold bond length was determined to be 2.01 Å, and the BDE 66 kcal/mol. Next, all constraints were removed and the geometry of the NHC-gold system was allowed to relax to a global minimum. The gold cluster reorganized to a planar geometry, and the NHC-gold bond length stretched slightly to 2.04 Å. The BDE also increased slightly to 68 kcal/mol. Bond length and BDE values reported in the main text represent a compromise among all of the structures studied computationally.

For crystollagraphic information, low-temperature diffraction data (φ- and ω-scans) were collected on a Bruker-AXS X8 Kappa Duo diffractometer coupled to a Smart Apex2 CCD detector with Cu K$_\alpha$ radiation (λ=1.54178 Å) from an IµS micro-source. The diffractometer was purchased with the help of funding from the National Science Foundation (NSF) under Grant Number CHE-0946721. The structure was solved by direct methods using SHELXS[14] and refined against F$^2$ on all data by full-matrix least squares with SHELXL-97[15] following established refinement strategies.

The compounds in Example 1 were synthesized as follows.

N,N'-bis(4-bromo-2,6-dimethylphenyl)formimidamide 6 was prepared according to the general procedure of Kuhn, K. M.; Grubbs, R. H. Org. Lett. 2008, 10, 2075-2077 in 96% yield (9.6 g) as a light-brown solid; in CDCl$_3$ at 25° C., 6 exists as two isomers in ~1:1 ratio (peaks listed together). $^1$H NMR (400 MHz, CDCl$_3$): δ 7.39-7.20 (br, 2H), 7.22 (s, 2H), 7.21 (s, 1H), 7.17 (br, 4H), 7.14 (s, 1H), 5.47 (d, J=12 Hz, 1H), 2.22 (s, 12H), 2.21 ppm (s, 12H). $^{13}$C NMR (100 MHz, CDCl$_3$): δ 146.55, 144.12, 136.16, 135.27, 131.65, 131.16, 130.98 (br), 130.80, 119.95, 115.95, 18.68, 18.61, 17.86 ppm. LCMS: calculated for C$_{17}$H$_{18}$Br$_2$N$_2$[M+H]$^+$, 411.0; found, 411.0.

1,3-bis(4-bromo-2,6-dimethylphenyl)-4,5-dihydro-1H-imidazol-3-ium chloride IS1 was prepared according to the general procedure of Kuhn et al.[17] (72 h) in 84% yield (17.5 g) as a beige powdery solid. $^1$H NMR (400 MHz, DMSO-d$^6$): δ 9.27 (s, 1H), 7.55 (s, 4H), 4.50 (s, 4H), 2.40 ppm (s, 12H). $^{13}$C NMR (100 MHz, DMSO-d$^6$): δ 169.40, 138.58, 131.39, 122.89, 50.79, 17.13 ppm. TOF HRMS: calculated for C$_{19}$H$_{21}$Br$_2$N$_2$Cl [M-Cl]$^+$, 437.0046; found, 437.0031.

1,3-bis(2,6-dimethyl-4-(E)-prop-1-en-1-yl)phenyl)-4,5-dihydro-1H-imidazol-3-ium chloride IS2 was prepared as follows. To a dry 7-mL vial with stir bar were added IS1 (946 mg, 2.00 mmol), Pd$_2$(dba)$_3$ (110 mg, 0.12 mmol) and $^t$Bu$_3$PH$^+$BF$_4$$^-$ (76 mg, 0.13 mmol), and the mixture was brought into the glove box with a nitrogen atmosphere. To the vial were added first CsF (1.28 g, 8.40 mmol), then allyltri-n-butylstannane (1.30 mL, 4.20 mmol; freeze-pump-thawed), and then N-methyl-2-pyrrolidone (2.0 mL). The vial was capped, the contents of the vial were briefly mixed and the vial was heated in a sand bath to 100° C. with stirring outside the glove box for 4.5 h. The contents of the vial were transferred to a 10-mL syringe and filtered through a PTFE, syringe filter (0.25 µm pore size) into stirring diethyl ether (125 mL, -20° C.). The vial was rinsed with dichloromethane (DCM, 2×1 mL), and the washings were filtered into diethyl ether, as well. Precipitate was collected by filtration in vacuo over a nylon membrane filter, washing with diethyl ether (2×25 mL, -20° C.). Collected white solid was re-dissolved in DCM (2 mL) and precipitated by adding diethyl ether (2 mL); the product was filtered in vacuo, and this precipitation/filtration protocol was repeated twice. The product was further purified by column chromatography on the Biotage® Isolera Prime™ Flash Purification System using a 50 g SNAP Ultra Flash Cartridge (3% methanol (MeOH) in DCM for 12 column volumes (CV), 3→5% MeOH over 4 CV, 5→10% MeOH over 4 CV, and maintained at 10% methanol for 4 CV; TLC R$_f$ in 5% methanol in DCM=0.17), affording IS2 as a beige solid (230 mg, 29% yield, mixture of E/Z isomers (9% Z)). $^1$H NMR (400 MHz, CDCl$_3$): δ 9.01 (s, 1H), 7.04 (s, 4H), 6.28 (AB d, J=16.0 Hz, 2H), 6.25 (AB dq, J$_1$=15.6 Hz, J$_2$=4.8, 2H), 4.59 (s, 4H), 2.38 (s, 12H), 1.87 ppm (d, J=4.8 Hz, 6H). $^{13}$C NMR (100 MHz, CDCl$_3$): δ 159.17, 140.05, 135.49, 131.08, 129.71, 128.50, 126.71 ppm. TOF HRMS: calculated for C$_{25}$H$_{31}$N$_2$Cl [M-Cl]$^+$, 515.2293; found, 515.2300.

(1,3-bis(4-bromo-2,6-dimethylphenyl)-4,5-dihydro-1H-imidazol-3-ium-2-yl)chloroaurate(I) 3. To a 25-mL 3-necked flask containing IS1 (95.5 mg, 0.202 mmol) and a stir bar under nitrogen were added THF (5 mL, anhydrous) and then 1.0 M KHMDS in THF (0.202 mL) via syringe. The mixture (IS1 is insoluble in THF) was stirred for 15 min, during which the dispersion became clearer and formation of tiny colorless microcrystalline solid was noted. The resulting mixture was added dropwise via syringe to a 50-mL 2-necked flask with a stirring solution of (Ph$_3$P)AuCl (100 mg, 0.202 mmol) in THF (5.0 mL, anhydrous) under nitrogen at -78° C. The reaction mixture was stirred for 1 hr at -78° C. and was then allowed to warm up to room temperature overnight. The reaction mixture was then filtered first in vacuo over a nylon membrane filter, washing with THF (3×5 mL); the filtrate was concentrated by rotary evaporation, re-dissolved in DCM (2 mL), filtered through a cotton plug, and mixed with hexanes (10 mL). After 3 hrs, the precipitate was filtered in vacuo over a nylon membrane filter and dried in vacuo, affording 3 (73 mg, 54% yield) as a gray solid. For X-ray crystallography, an 11 mg sample was dissolved in DCM (2 mL) and crystallized over 2 days by slow diffusion of hexane at room temperature. $^1$H NMR (400 MHz, CDCl$_3$): □: MR (400 MHz, CDCl as a gray solid. For X-r $^{13}$C NMR (100 MHz, CDCl$_3$): δ 138.06, 136.16, 132.24, 50.67, 18.05 ppm (carbene carbon signal not detected). LCMS: calculated for C$_{19}$H$_{20}$AuBr$_2$N$_2$Cl [M-Cl+MeCN]$^+$, 674.0; found, 674.0.

Bis(1,3-bis(2,6-dimethyl-4-(prop-1-en-1-yl)phenyl)-4,5-dihydro-1H-imidazol-3-ium-2-yl)aurate(I) chloride 7 was prepared as follows. A 7-mL vial containing IS2 (79.0 mg, 0.200 mmol) and a stir bar, as well as a 3-mL vial with (Ph$_3$P)AuCl (49.5 mg, 0.100 mmol) were taken inside the glove box with nitrogen atmosphere. To both vials was added anhydrous THF (1.5 mL to the former and 1.0 mL to the latter). To the vial with a stirring mixture of IS2 in THF was added 1.0 M KHMDS in THF (0.20 mL), and after 5 min, to the resulting solution was added the solution of (Ph$_3$P)AuCl dropwise. The vial was washed with 0.1 mL THF and this was also added to the reaction mixture. After 1d, added an additional portion of NHC 2 (formed from 16.2 mg of IS2, 0.3 mL THF, and 0.041 mL of 1.0 M KHMDS in THF in the glove box). After one more day, the reaction was filtered through a PTFE syringe filter (0.25 µm pore size) into hexanes (15 mL). The precipitate was collected by filtration in vacuo over a nylon membrane, washing with hexanes (3×5 mL), and then dried in vacuo, affording 7 as a beige powdery solid (45.6 mg, 48% yield, mixture of E/Z isomers (27% Z)). $^1$H NMR (400 MHz, CDCl$_3$): δ 6.90 (s, 8H), 6.39 (AB d, J=16.4 Hz, 2H), 6.32 (AB dq, J=16.0 Hz, 2H), 3.92 (s, 8H), 1.97 (d, J=5.2 Hz, 12H), and 1.84 (s, 24H). $^{13}$C NMR (100 MHz, CDCl$_3$): δ 206.27, 138.22, 135.81, 135.01, 130.24, 127.28, 126.13, 51.45, 18.76, 17.57 ppm. TOF HRMS: calculated for C$_{50}$H$_{60}$AuN$_4$Cl [M-Cl]$^+$, 913.4478; found, 913.4470.

Bis(1,3-bis(4-bromo-2,6-dimethylphenyl)-4,5-dihydro-1H-imidazol-3-ium-2-yl)aurate(I) chloride 8 was prepared as follows. Under positive pressure of nitrogen, to a 50-mL 2-neck flask vial equipped with a stir bar was added IS1 (0.9447 g, 2.00 mmol), and a Merlic-type solid addition adapter containing (Ph$_3$P)AuCl (0.495 g, 1.00 mmol) was attached; the set up was evacuated and re-filled with nitrogen three times. To the flask was added anhydrous THF (25 mL) and then, while stirring, 1.0 M KHMDS in THF (2.0 mL); after 10 min, the solid-addition adapter was inverted, adding (Ph₃P)AuCl to the reaction mixture. Immediate formation of white precipitate was observed. After 6 hrs, the reaction mixture was opened to air, filtered in vacuo over a nylon membrane, washing with THF (3×8 mL), and then re-dissolved in minimal dichloromethane and filtered again. The filtrate was concentrated by rotary evaporation and dried in vacuo, affording 8 as an off-white solid (0.875 g, 79% yield). ¹H NMR (400 MHz, DMSO-d⁶): δ 7.35 (s, 8H), 3.98 (s, 8H), and 1.93 ppm (s, 24H). ¹³C NMR (100 MHz, DMSO-d⁶): δ 204.61, 138.42, 135.80, 131.00, 121.74, 50.68, 16.69 ppm. TOF HRMS: calcd. for $C_{38}H_{40}AuBr_4N_4Cl$ [M-Cl]⁺, 1068.9622; found, 1068.9640.

1,3-Bis(4-bromo-2,6-dimethylphenyl)-4,5-dihydro-1H-imidazol-3-ium-2-carboxylate $CO_2$-1. A 7-mL vial containing IS1 (236 mg, 0.500 mmol) and a stir bar was taken inside the glove box with nitrogen atmosphere. To the vial was added anhydrous THF (3.5 mL) and to the stirring suspension was added 1.0 M KHMDS in THF (0.50 mL). After 10 min, the reaction mixture was filtered through a 0.25 μm PTFE syringe filter into a 2-5 mL Biotage® microwave vial, and the vial was capped and removed from the glove box. Through the solution was then bubbled $CO_2$ gas, with white precipitate forming instantly. After 2 min, the reaction mixture was filtered over a medium-porosity frit, washing with THF (5 mL). Drying in vacuo afforded $CO_2$-1 adduct as a powdery white solid (117 mg, 49% yield). 1H NMR (400 MHz, DMSO-d⁶): δ 7.45 (s, 4H), 4.31 (s, 4H), and 2.40 ppm (s, 12H). ¹³C NMR (100 MHz, DMSO-d⁶): δ 164.06, 153.56, 139.37, 133.03, 131.09, 122.63, 49.23, 16.83 ppm. LCMS: calculated for $C_{20}H_{20}Br_2N_2O_2$ [M-$CO_2$+H]⁺, 437.0; found, 437.0.

Example 3

This example is a prophetic example.
Introduction:
Relatively little attention has been given to incorporation of NHCs into platforms for in vivo metal ion detection and gold nanoparticle stabilization. This example demonstrates the design and synthesize of a series of NHC-based polymers, that could act as ligands for gold nanoparticles and sensors for various biologically-relevant metal ions. The design employed NHC moieties embedded between water-soluble, oligo(ethylene glycol) (OEG) chains. The latter species imparted water-solubility, biocompatibility, and recyclability while the NHC species was used for nanoparticle binding and ion sensing.

A library of these materials, which could be screened for function, was prepared. Construction of a library required an efficient, modular polymerization process. Copper (I)-catalyzed azide-alkyne cycloaddition (CuAAC), the prototypical "click" reaction, was chosen for this purpose. In addition, novel aryl dialkyneimidazolium NFIC precursors were readily prepared on a large scale. CuAAC reactions between the precursors and PEG diazide derivatives yielded PEG-NHC "click-o-mers," which could be used as novel biomaterials.

Results and Discussion: Synthesis of Click-O-Mers:

Two unprecedented but potentially highly useful bis-aryl-imidazolium fragments (4 and 4', Scheme 6) were chosen as NHC precursors to explore the effect of junction placement on the metal ion or nanoparticle binding capability. The carbene moiety of the precursors was revealed on treatment with base. Installing the junctions ortho to the NHC (4', Scheme 6) was expected to reduce the accessibility of the carbene, which could lead to diminished binding ability compared to click-o-mers with para-substituted junctions (4, Scheme 6). The synthesis of the imidazolium fragments was achieved in 9-13% yield over 3 steps from commercially available starting materials 1 and 1' (Scheme 6). Thanks to the ease of synthesis and potential for elaboration via CuAAC, these dialkyne NHC precursors may find broad use as NHC modules for incorporation into to a wide range of materials.

Scheme 6.

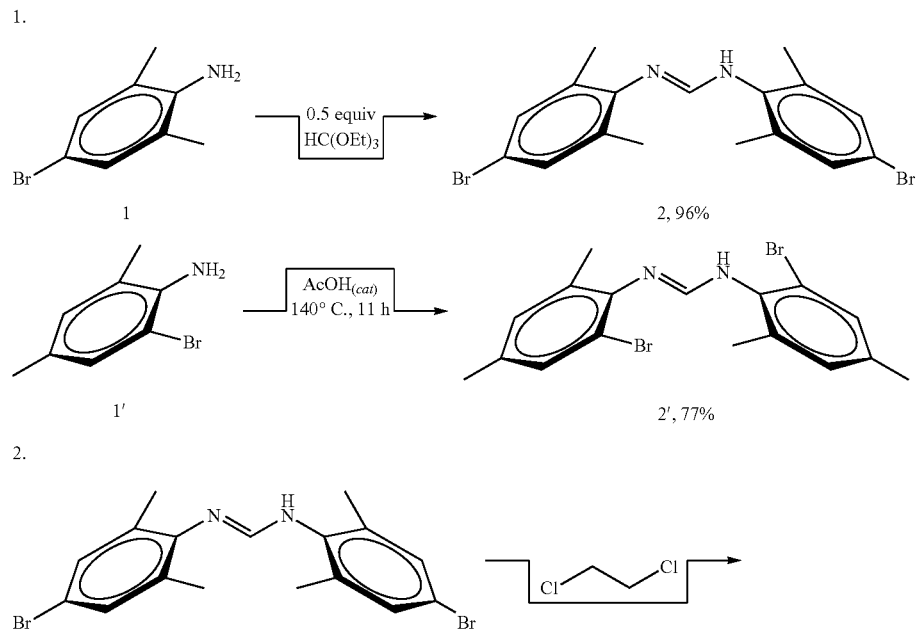

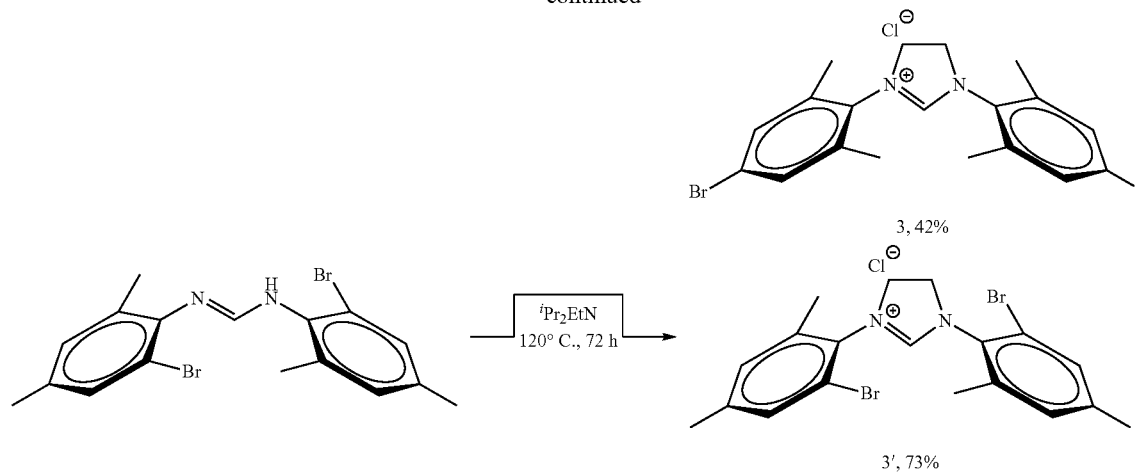

3.

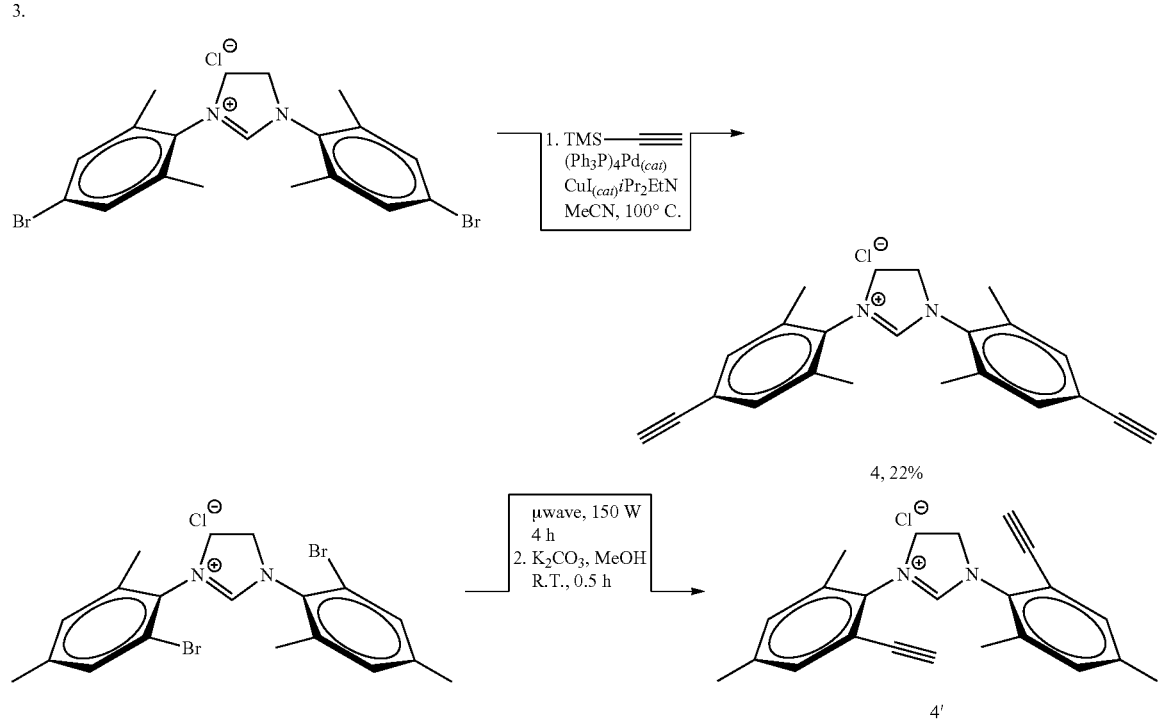

In order to fine tune the binding properties of the click-o-mers and enhance their water solubility, the bis-azide click partners for bis-alkynes 4 and 4' were synthesized in two steps from oligo(ethylene glycol)s (OEGs) of varying lengths (Scheme 7).

Scheme 7.

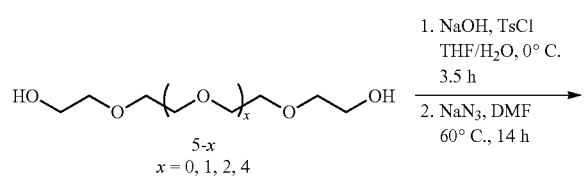

-continued

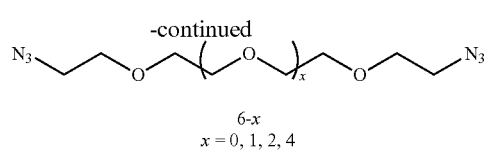

6-x
x = 0, 1, 2, 4

Decreasing the length of the OEG fragments was expected to allow the chelation of metal ions by increasing metal ion affinity and possibly the selectivity of the click-o-mers. Additionally, CuAAC gives rise to triazole rings, which are known ligands for metal ions. Thus, the differential binding of the triazoles and NHCs was expected to allow simultaneous sensing of different metal ions. Click-o-mers A-x and A'-x (x=0, 1, 2, 4) were assembled via CuAAC of the bis-azide and the bis-alkyne fragments described above and shown in Scheme 8.

Scheme 8.

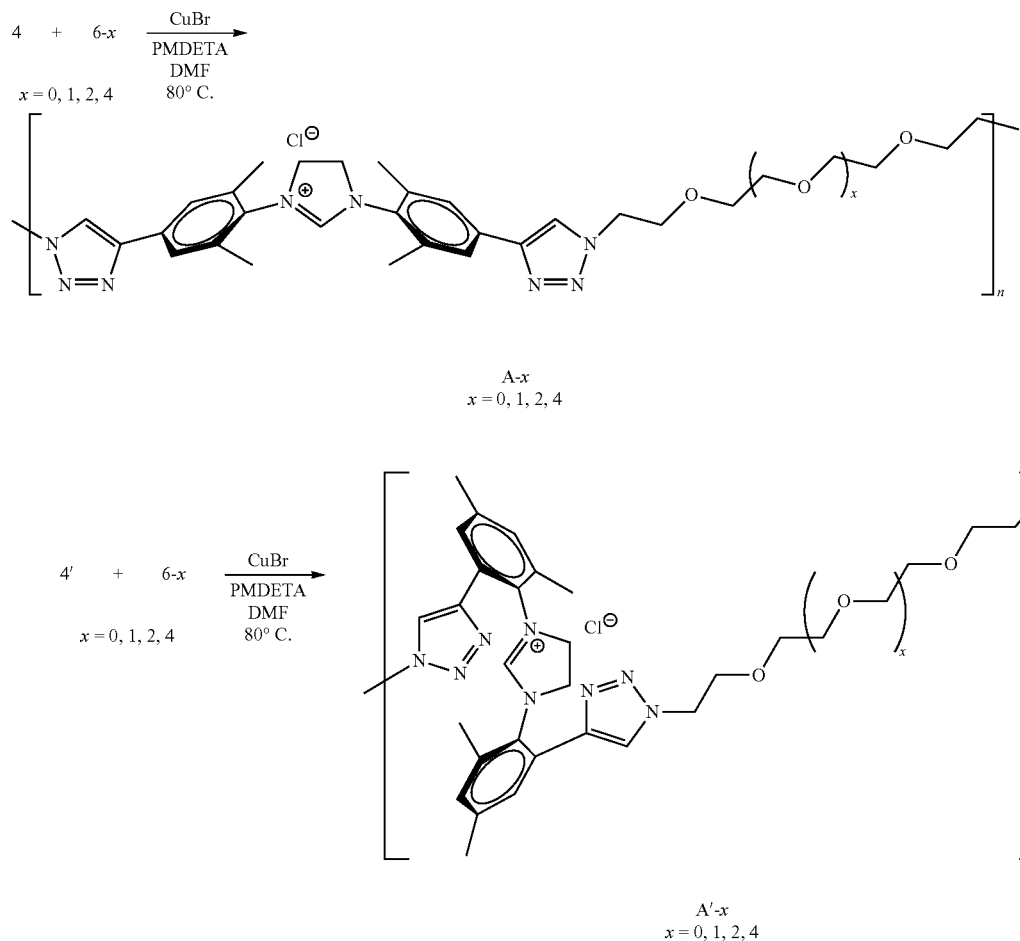

Metallation of Click-O-Mers:

The imidazolium fragments embedded in the click-o-mers served as the NHC precursors. To determine the metal ion-binding capacity of the click-o-mers, the NHC functionalizable groups were unveiled by treatment of the click-o-mers with potassium hydroxide (KOH) in the presence of several different metal ions (i.e., Cu(I), Cu(II), Ni(II), Fe(II), and Fe(III), and Au(III)) in water. UV-Vis spectroscopy was used to characterize absorption changes upon metal binding and metal ion uptake was quantified via inductively coupled plasma atomic emission spectroscopy. To assess the metal ion uptake capacity and selectivity of the triazole moieties, the same experiments were carried out without adding KOH. Treatment of the metallated click-o-mers with ethylenediaminetetraaceticacidin water was explored to recycle the click-o-mers.

Synthesis of Gold Nanoparticles:

Due to the ability of the click-o-mers to bind Au(III) ions, the synthesis of gold nanoparticles in the presence of the click-o-mers under basic conditions was performed. The conditions for nanoparticle synthesis are summarized in Scheme 9.

Scheme 9.

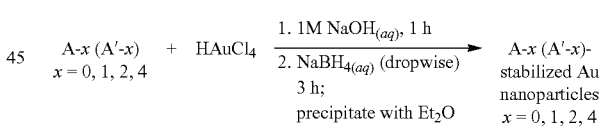

The size distribution of the gold nanoparticles was quantified through transmission electron microscopy. Elemental analysis was used to determine the average number of stabilizing groups per gold nanoparticle.

Conclusions:

This work described the synthesis of a series of novel NHC and triazole containing water soluble "click-o-mers." Each click-o-mer was tested for its ability to bind several different metal ions and stabilize nanoparticles in an aqueous setting. This example demonstrates the first instance of water-soluble NHC-stabilized gold nanoparticles and polymer-supported prototypes of NHC-based in vivo metal-ion sensors, which opens the door to the development of novel nanoparticle based disease treatments and biomedical probes.

Experimental:

Compounds 3 and 3', as well as 6-x, were prepared following known protocols. General procedure for conversion of 3' to 4'. To a capped 10-mL microwave vial equipped with a stir bar and containing 3' (0.200 g, 0.423 mmol), CuI (0.032 g, 0.17 mmol), and (Ph3P)4Pd (0.0813 g, 0.0704) were added, sequentially, anhydrous, deoxygenated acetonitrile (3.8 mL), deoxygenated trimetylsilylacetylene (0.60 mL, 4.2 mmol), and anhydrous, deoxygenated diisopropylethylamine (DIPEA; 0.53 mL, 3.0 mmol). The reagents were mixed and subjected to microwave irradiation (150 W) at 100° C. over 4 h; the progress of the reaction was monitored by LCMS. After the reaction was complete, the reaction mixture was allowed to cool to room temperature, and was then filtered through Celite® 545. The filtrate was concentrated in vacuo, and the residue was redissolved in dichloromethane (2 1mL), Addition of diethyl ether (25 mL) resulted in precipitation of DIPEA¬ hydrochloride which was then removed by vacuum filtration over a frit with medium porosity. The filtrate was concentrated in vacuo and then subjected to column chromatography on $SiO_2$, eluting with a gradient of 100% dichloromethane to 9:1 dichloromethane/methanol, to afford the pure bis(silylated) intermediate. The trimethylsilyl protective groups were removed by stirring the bis(silylated) intermediate (0.0943 g, 0.186 mmol) with potassium carbonate (0.165 g, 1.19 mmol) in methanol (5 mL) for 30 min, followed by neutralizing the solution with 1M HCl (sq) (2.4 mL). After removal of solvent in vacuum, water (30 mL) was added to the crude product, and the insoluble product was collected by vacuum filtration over a frit of medium porosity and dried in vacuo to afford 4(') (23%) as a beige-brown solid.

General procedure for the CuAAC polymerization. To a flask equipped with a stir bar and containing a 0.5 M solution of 40 (1.0 equiv) was added 6-x (1.0 equiv), CuBr (0.10 equiv), and PMDETA (0.20 equiv), The reaction mixture was deoxygenated by the freeze-pump-thaw technique, placed under an atmosphere of nitrogen, and stirred at room temperature for 24 h, Polymer was precipitated by addition of diethyl ether.

Example 4

Figure 14A:
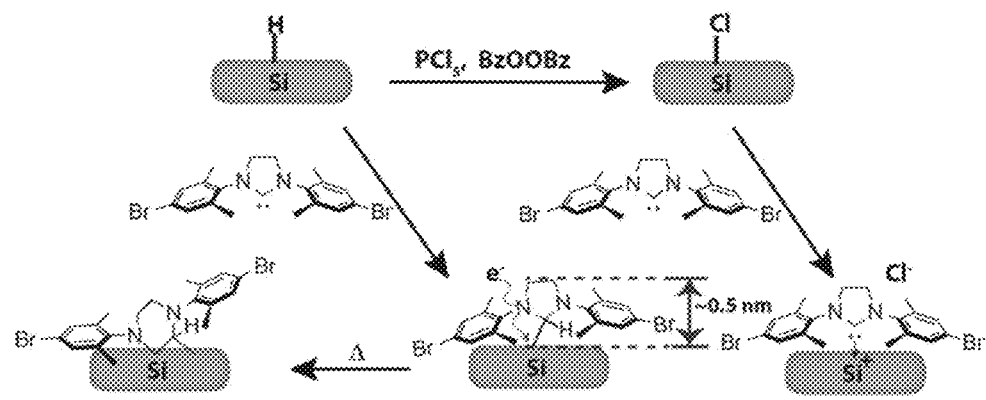
FIG. 14A and FIG. 14B show schemes of a non-limiting treatment of rearranged NHC—Si surface with a secondary compound, according to certain embodiments.

This example describes the formation of N-heterocyclic carbene (NHC) monolayers on hydrogen- and chlorine-terminated silicon surfaces (Si—H and Si—Cl, respectively). Formation of NHC-derived monolayers in both cases was demonstrated via X-ray photoelectron spectroscopy (XPS) combined with solution NMR studies of model species. Without being bound by theory, it is believed that the formation of the monolayers on Si—H took place via effective insertion of the carbene into Si—H bonds, while in the case of Si—Cl—via displacement of Cl⁻. Notably, this example describes the ring expansion of the surface-bound NHC species to afford a 2-D alternating array of strong Si—C and labile Si—N bonds as shown in FIG. 14A. This silicon modification route allowed for the controlled bottom-up fabrication of nanoscale patterns on silicon surfaces.

Scheme 10. NHCs used in this example.

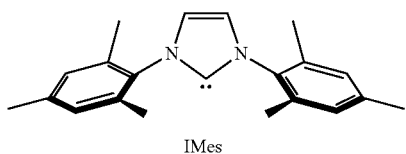

IMes

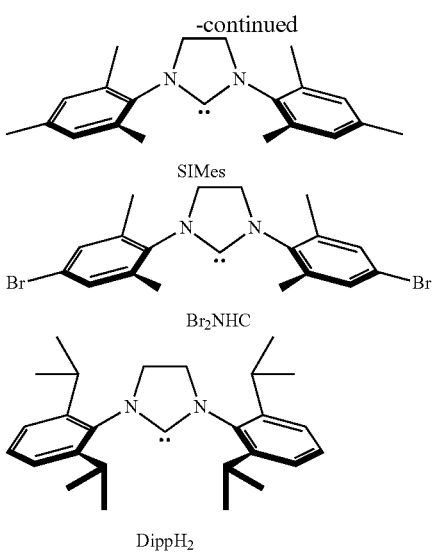

SIMes

Br2NHC

DippH2

Silicon surface chemistry has been foundational to silicon-based electronics and photovoltaics. Traditionally, a thermal oxide layer has served to passivate the silicon surface to minimize charge trapping at surface defects. However, many applications call for non-oxide-based surface derivatization. For example, a singlet fission-at-silicon surface has been proposed to dramatically increase the efficiency of solar cells. For this process to take place, the substance capable of singlet fission must be sufficiently proximate to the silicon surface to allow for efficient charge transport between them. Therefore, any layer separating them should ideally offer a low electron-tunneling barrier, yet passivate the silicon surface and provide a barrier from such species as dioxygen and water in the ambient environment. NHCs were used to functionalize silicon surfaces. It was anticipated that NHC would form a monolayer architecture on silicon surfaces, with the steric bulk of the N-substituent offering control over the density of surface functionalization. Furthermore, the thickness of the resulting monolayer was expected to be ~0.5 nm, which would enable efficient electron tunneling. Lastly, thermally activated transformations secondary to NHC binding, known to take place in small molecule systems, would afford alteration of Si surface functionality. The NHCs shown in Scheme 11 were used for monolayer formation. Introduction of bromine substituents on the aryl rings served to facilitate the monolayer characterization by XPS, as well as provide sites for further functionalization.

Figure 11A:
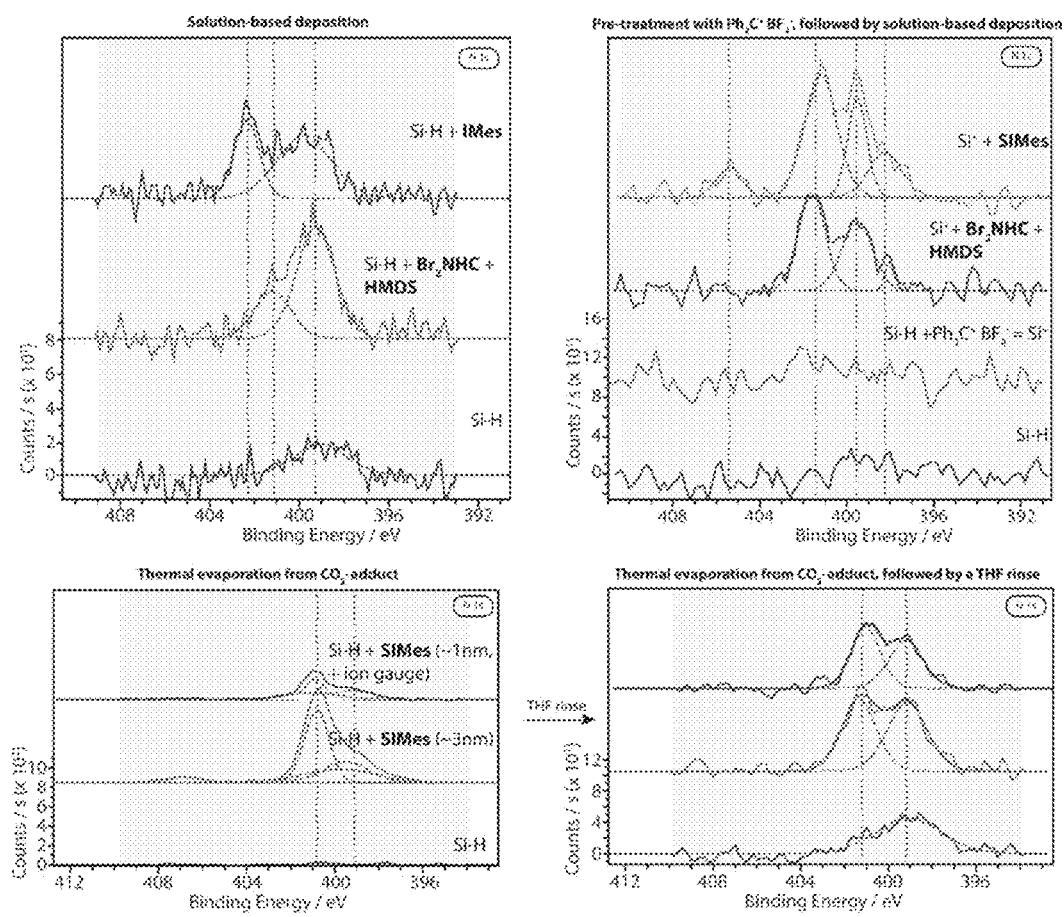
FIG. 11A and FIG. 11B show XPS spectra of bis-persistent carbenes associated with two substrates, according to certain embodiments.
Figure 11A:
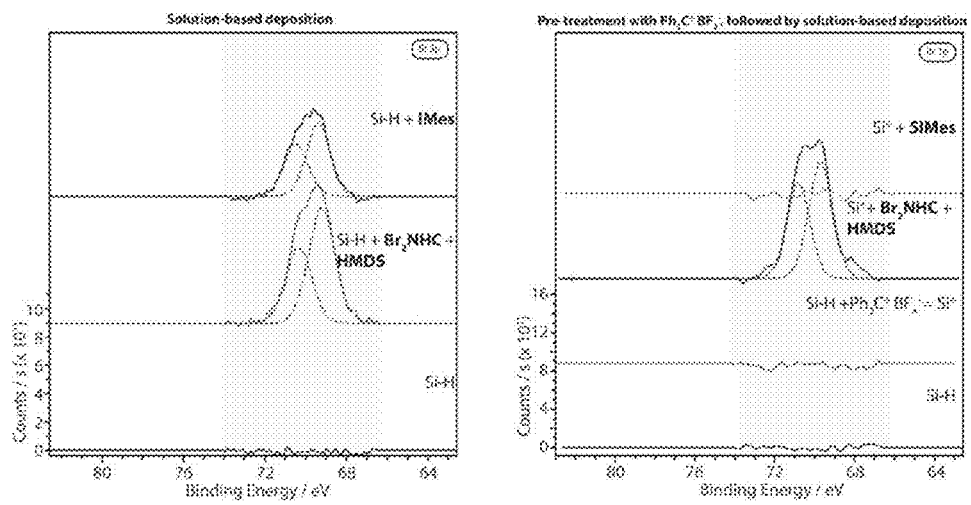
Figure 11B:
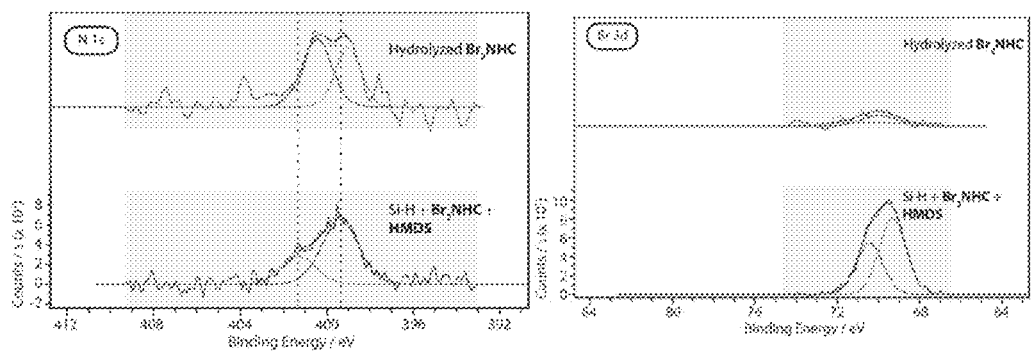
Figure 14B:
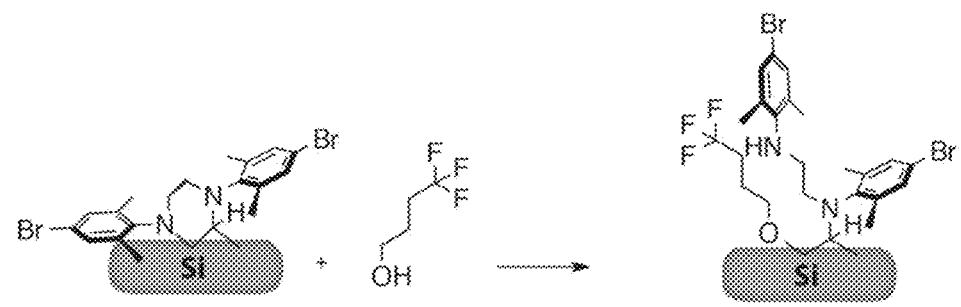

Deposition of NHC monolayers from solution was accomplished by either using pure NHC or by first treating a corresponding imidazolium salt with KHMDS. Gas-phase deposition was carried out by thermolysis of NHC—$CO_2$ in a thermal evaporator. Regardless of the method used, the surfaces were rinsed with THF to remove weakly adsorbed species, and then subjected to XPS analysis, limiting exposure to ambient atmosphere to ~10 min. As expected, the surfaces treated with Br-containing NHCs exhibited a single set of Br 3d peaks as shown in FIG. 11A, while the Si—H surface and the surface treated with SIMes showed none. FIG. 11A shows Br 3d and N 1s XPS of NHC—SiH monolayers from solution or from evaporation. Comparison of the N 1s region in FIG. 11A revealed that all surfaces treated with NHCs, regardless of whether or not HMDS was present, had two N 1s peak components (~401.2 eV and 399.3 eV for NHCs with saturated backbones and ~402.3 eV and ~399.9 eV for IMes) in different proportions, indicating either two modes of NHC binding, binding of different NHC-derived species, or both. Treatment of the surface with a solution of the product of $Br_2NHC$ hydrolysis resulted in 10% of the amount of binding (based on the Br 3d region comparison) observed with $Br_2NHC$ as shown in FIG. 11B. FIG. 11B shows N 1s and Br 3d XPS regions of negative controls compared with Br2NHC+HMDS treatment. Furthermore, the binding energies of the N1s components (which in the spectrum of the hydrolyzed product are present in a ~1:1 ratio) did not match those observed for $Br_2NHC$ as shown in FIG. 11B. Hence, NHC hydrolysis could not account for the observed peaks. This indicated that a secondary ring-expansion rearrangement processes observed for NHC-silane adducts was taking place at room temperature in NHC-treated silicon surfaces. The Si surface associated with the rearranged persistent carbene was used to further functionalize the Si as shown in FIG. 14B.

Functionalization of Si—Cl with NHCs was expected to provide an alternate surface chemistry to the one on Si—H, because the mechanism of surface binding was expected to be different (i.e., chloride displacement versus Si—H bond insertion). The resulting silicon surface was expected to consist of $[NHC—Si]^+Cl^-$ species, as well as potentially unreacted Si—Cl sites (due to steric bulk of the NHCs). The Si—Cl surface, as well as surfaces treated with $Br_2NHC$/HMDS, IMes, and HMDS alone were analyzed by XPS. The Cl 2p region of the XPS spectra revealed that treatment with NHCs reduced the overall chlorine quantity and afforded an additional chlorine chemistry with a much lower binding energy, corresponding to the displaced chloride anion. In contrast, while a small amount of chloride was displaced by HMDS, the overall chlorine count remained virtually unchanged. These observations were consistent with the proposed displacement of chloride by the NHC concomitant with binding to the silicon surface. However, overall loss of chlorine and presence of two N 1s peak components for NHC-treated surfaces again suggested that a secondary transformation of NHC—Si surfaces was operative, resulting in chloride loss not present in HMDS-treated surface. This may arise through Si-migration to form the product of formal NHC insertion into Si—Si bonds. This migration could result in hole migration into the silicon bulk and detachment of the chloride anion. Charge neutrality could be conserved by loss of silicon-based cations.

Example 5

This example describes associating a first and second persistent carbene with a first and second substrate, respectively.

Controlling the interface between two different for many applications including physical separation of co-diffusive metals such as copper and gold with the nickel barrier in electronics components like phone chargers. Without the presence of the nickel/gold interface, the diffusion of copper into the gold and eventual formation of copper oxides on the gold contact's surface would render the electronic device unusable. However, beyond sputtering and thermal evaporation, few methods exist for forming a controlled, thermally stable, and electronically conductive interface between nickel derivatives and gold. This example describes solution-based method for seeding a nickel(II) layer on the surface of gold (111) coated with a monolayer of strongly-binding ligands. Given that NHCs form strongly bound monolayers on gold, rigid bis-NHC structures capable of binding to the gold surface were selected as the seeding layer and then presented another NHC for seeding the next layer. The ability of bis(NHC)s to seed nanometer-thin layers allowed for the integration of dissimilar materials into new forms of nanotechnology.

Self-assembled monolayers, as a form of nanotechnology, have allowed for the controlled modification of interface properties. These monolayers have even allowed for the assembly of nanoscopic objects on surfaces through seeding crystallization. However, the limitations of the existing methodology include low monolayer stability on metals such as gold (as these are usually based on thiols), poor scope of the materials to be seeded and/or poor scope of the materials on which the seeding takes place.

Figure 12:
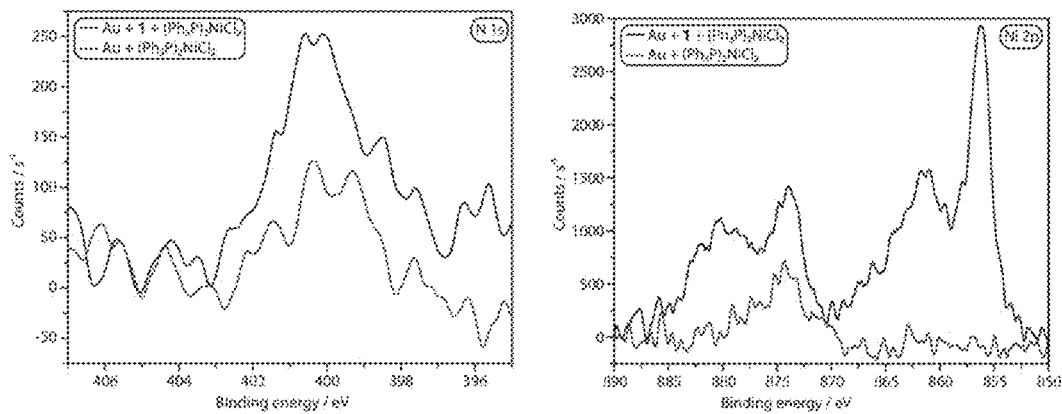
FIG. 12 shows XPS spectra of persistent carbenes on a metal oxide surface, according to certain embodiments.
Figure 15:
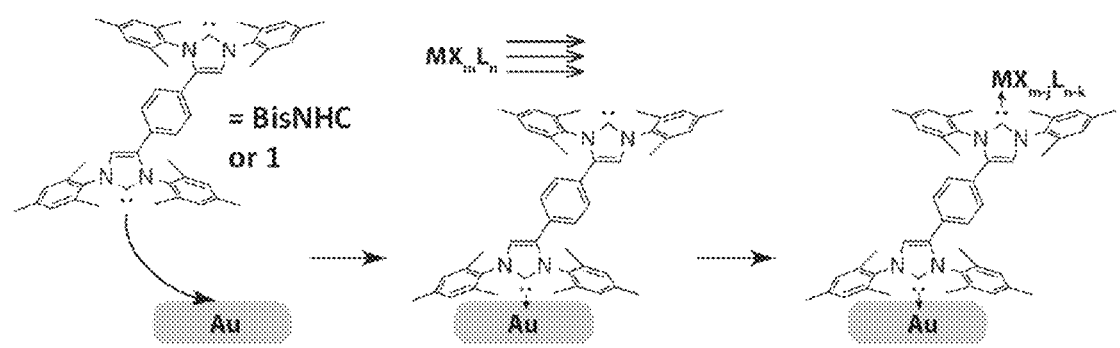
FIG. 15 shows a scheme of a non-limiting approach to seeding a layer of species on gold using a monolayer of BisNHC, according to certain embodiments.

In this example, rigid bis-NHC structures were used to form monolayers on gold and still have an available NHC to bind other species using the remaining carbene as shown in FIG. 15. $(Ph_3P)_2NiCl_2$ was selected as the other species because it showed the least nonspecific binding to bare gold, and abundant binding after BisNHC treatment. FIG. 12 shows the XPS of the Ni seeded layer on a BisNHC layer on Au. BisNHC binding was substantially the same as single carbene species. When the Ni(II) solution was passed over the BisNHC-treated gold surface, initial binding was followed by mass loss from the surface, suggestive of phosphine and chloride dissociation from Ni(II). After rinsing the resulting surface with THF and again adding more of the BisNHC solution, extensive binding was again observed.

Example 6

This example describes the association of a persistent carbene with a metal oxide substrate.

Oxide surfaces are some of the most abundant in the oxidizing atmosphere on Earth. Hence, oxide surface functionalization is required for many applications, ranging from magnetic iron oxide nanoparticles for MRI to indium tin oxide-based solar cells. However, few methods exist for functionalizing oxide surfaces. This example describes the use of a carbene, as described herein, to functionalize oxide surfaces. Diamidocarbene HCl (DAC.HCl) adducts were used to bind to oxide surfaces via effective chloride substitution with oxide. XPS, FTIR-ATR and, UPS were employed to characterize the DAC.HCl-treated surfaces.

Figure 13A:
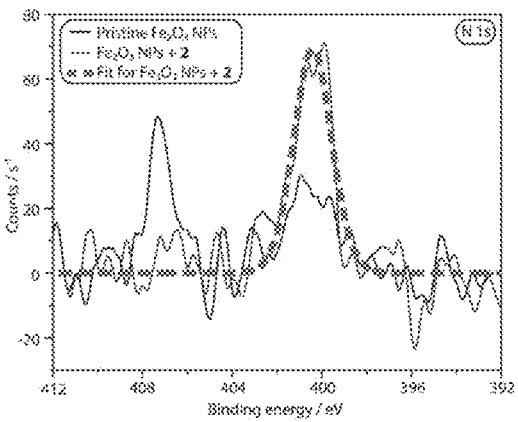
FIG. 13A and FIG. 13B show XPS spectra of persistent carbenes associated with a metal oxide surface, according to certain embodiments.
Figure 13B:
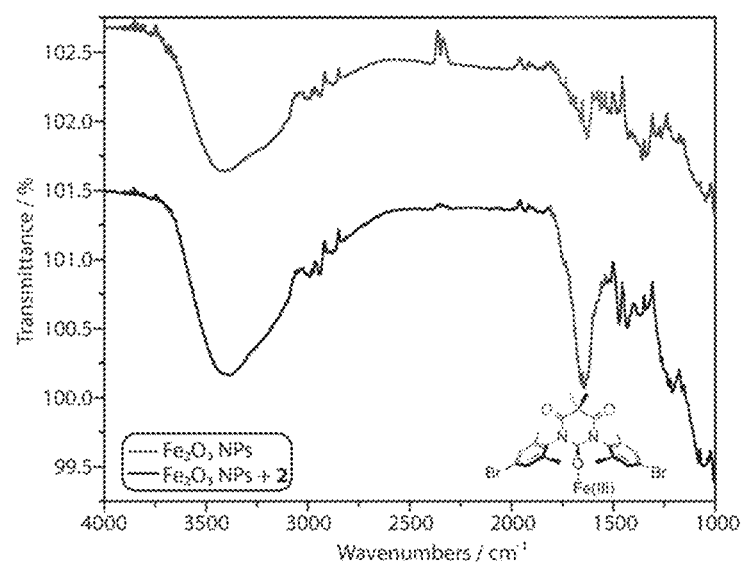
Figure 16:
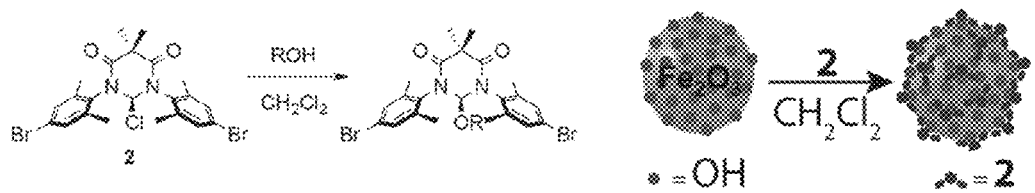
FIG. 16 shows a scheme for DAC.HCl reactivity and a non-limiting method for functionalizing metal oxide substrates, according to certain embodiments.

DAC.HCl was used as a general method for functionalization of oxide surfaces, like that of $Fe_2O_3$ nanoparticles as shown in FIG. 16. The oxides were treated by soaking the surface in the saturated solution of the DAC.HCl in dichloromethane (DCM) for one day followed by a thorough rinse with DCM and then pentanes. XPS studies, as shown in FIG. 13A, indicated a greater "N" content in the DAC.HCl treated $Fe_2O_3$ nanoparticles; the energy of N1s was, furthermore, characteristic of amide nitrogen. FIG. 13A shows of pristine $Fe_2O_3$ nanoparticles and nanoparticles treated with $Br_2DAC.HCl$. While bromide anions were present in the nanoparticles, upon treatment with DAC.HCl, the observed bromide peak was shifted to higher binding energy, corresponding to the carbon-bound Br in the DAC. The observed Br:N ratio of 1 matched the expected ratio for DAC.HCl. FTIR-ATR interrogation of the same $Fe_2O_3$ nanoparticles revealed a large amide peak for the DAC.HCl treated ones, virtually absent in the pristine nanoparticles, as shown in FIG. 13B. FIG. 13B shows FTIR-ATR spectrum of pristine $Fe_2O_3$ nanoparticles and nanoparticles treated with $Br_2DAC.HCl$.

Figure 13C:
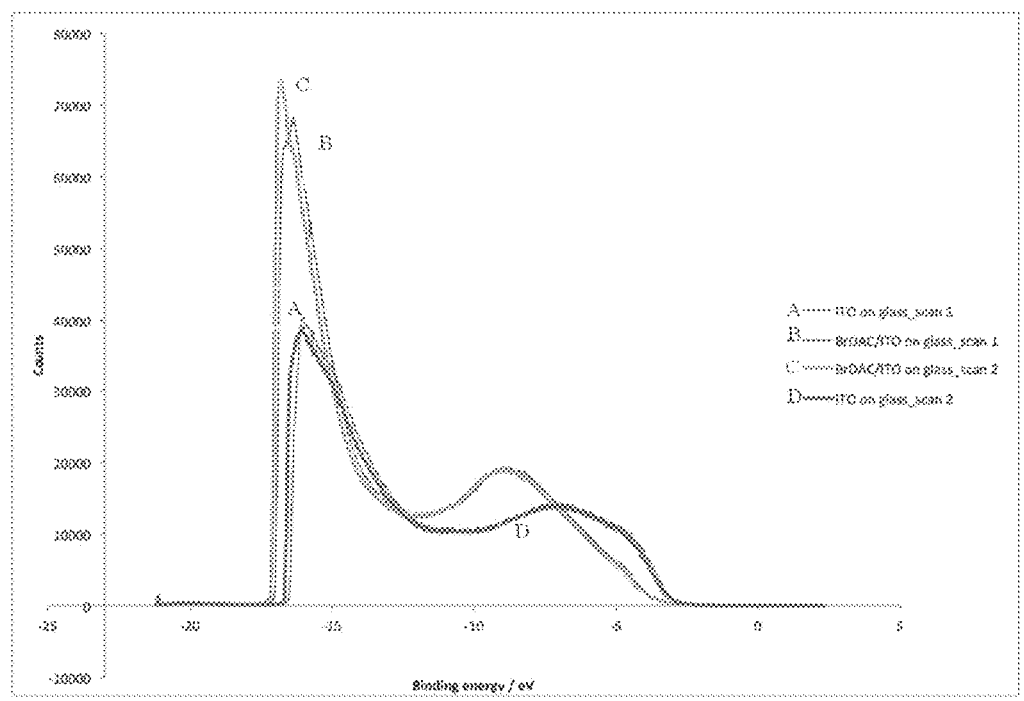
FIG. 13C shows FTIR spectra of persistent carbenes associated with ITO in connection with FIG. 13A and FIG. 13B, according to certain embodiments.

ITO nanoparticles were subjected to the same treatment, except both the $Br_2DAC$ and $Me_2DAC.HCl$ adducts were employed to compare the Br count. By XPS, there was no detectable Br on the surface of pristine ITO nanoparticles and the ITO surface treated with Me$_2$DAC.HCl. FIG. 13C shows XPS spectrum of pristine ITO nanoparticles and the ITO surface treated with Br$_2$DAC.HCl. A significant Br peak was observed for the Br$_2$DAC.HCl treated ITO surfaces. This indicated that the observed bromine was derived from the DAC. The nitrogen region in the XPS showed a slight increase in nitrogen count in DAC.HCl-treated surfaces; however, nitrogen presence in pristine ITO nanoparticles was evident. The In region was considerably different for the DAC.HCl-treated surfaces compared to the pristine ones. There was a slight reduction in intensity as well as a significant shift toward lower binding energies. This observation leads us to believe that the indium oxide sites have prevalent reactivity with the DAC.HCl. UPS comparison of ITO film treated with DAC.HCl and untreated shows a marked shift in the high-lying ITO energy levels.

The following references are incorporated herein by reference in their entirety: U.S. Provisional Patent Application Ser. No. 61/779,251, filed Mar. 13, 2013, entitled "Articles and Methods Comprising Persistent Carbenes and Related Compositions," by Johnson, et al. and U.S. Provisional Patent Application Ser. No. 61/817,529, filed Apr. 30, 2013, entitled "Articles and Methods Comprising Persistent Carbenes and Related Compositions," by Johnson, et al.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article, comprising:
a substrate having a surface, wherein at least a portion of the surface is associated with a plurality of persistent carbenes and a plurality of secondary compounds, wherein each of the plurality of the persistent carbenes and each of the plurality of the secondary compounds comprise at least one functionalizable group.

2. The article of claim 1, wherein the secondary compound comprises a thiol, thioether, selenol, dithiocarbamate, dithioate, dithiophosphinate, phosphonate, carboxylic acid, carboxylate group, amino, aminoacyl, pyridine, phosphine, alcohol, alkoxy, nitrile, isocyanide, alkyl, alkenyl, aryl, or alkynyl group.

3. The article of claim 1, wherein the secondary compound is associated with the surface via a thiol, thioether, selenol, dithiocarbamate, dithioate, dithiophosphinate, phosphonate, carboxylic acid, carboxylate group, amino, aminoacyl, pyridine, phosphine, alcohol, alkoxy, nitrile, isocyanide, alkyl, alkenyl, aryl, or alkynyl.

4. The article of claim 1, wherein the substrate comprises a metal, a metalloid, an organic material, a non-metal, or combinations thereof.

5. The article of claim 1, wherein a portion of the substrate comprises gold.

6. The article of claim 1, wherein the substrate comprises a plurality of particles.

7. The article of claim 1, wherein the plurality of persistent carbenes and/or plurality of secondary compounds form a monolayer on at least one surface of the substrate.

8. A sensor comprising the article of claim 1.

* * * * *